(12) United States Patent
He et al.

(10) Patent No.: US 9,132,152 B2
(45) Date of Patent: Sep. 15, 2015

(54) COMPOSITIONS AND METHODS FOR GENERATING INDUCED PLURIPOTENT STEM CELLS

(75) Inventors: Lin He, Berkeley, CA (US); Yong Jin Choi, Oakland, CA (US); Chao-Po Lin, El Sobrante, CA (US); Gregory J. Hannon, Cold Spring Harbor, NY (US); Xingyue He, Cambridge, MA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 13/369,997

(22) Filed: Feb. 9, 2012

(65) Prior Publication Data

US 2012/0207723 A1 Aug. 16, 2012

Related U.S. Application Data

(60) Provisional application No. 61/441,367, filed on Feb. 10, 2011.

(51) Int. Cl.
*A61K 35/12* (2015.01)
*C12N 5/10* (2006.01)
*C12N 5/071* (2010.01)
*C12N 5/074* (2010.01)

(52) U.S. Cl.
CPC .............. *A61K 35/12* (2013.01); *C12N 5/0696* (2013.01); *C12N 2501/602* (2013.01); *C12N 2501/603* (2013.01); *C12N 2501/604* (2013.01); *C12N 2501/606* (2013.01); *C12N 2501/65* (2013.01); *C12N 2506/13* (2013.01); *C12N 2510/00* (2013.01)

(58) Field of Classification Search
CPC ............. C12N 2501/65; C12N 5/0696; C12N 2510/00; C12Q 2600/178
See application file for complete search history.

(56) References Cited

U.S. PATENT DOCUMENTS

2009/0047263 A1* 2/2009 Yamanaka et al. ............ 435/377
2009/0311788 A1* 12/2009 Pachuk et al. ................. 435/455
2009/0317907 A1* 12/2009 Esau et al. ..................... 435/375

OTHER PUBLICATIONS

Judson, R. L., Babia, J. E., Venere, M. & Blelloch, R. Embryonic stem cell-specific microRNAs promote induced pluripotency. Nature Biotechnol. advance online publication, doi:doi:10.1038/nbt.1535 (Apr. 12, 2009).*
Dario Antonini et al., Transcriptional Repression of miR-34 Family Contributes to p63-Mediated Cell Cycle Progression in Epidermal Cells. Journal of Investigative Dermatology (2010) 130, 1249-1257.*
Zhao et al., Two Supporting Factors Greatly Improve the Efficiency of Human iPSC Generation. Cell Stem Cell 3, Nov. 6, 2008. p. 475-479.*
He et al., The Guardian's Little Helper: MicroRNAs in the p53 Tumor Suppressor Network. Cancer Res 2007;67:11099-11101.*
Raver-Shapira et al., Transcriptional Activation of miR-34a Contributes to p53-Mediated Apoptosis. Molecular Cell. vol. 26, Issue 5, Jun. 8, 2007, pp. 731-743.*
Tarasov et al., Differential Regulation of microRNAs by p53 Revealed by Massively Parallel Sequencing: miR-34a is a p53 Target That Induces Apoptosis and G1-arrest., 2007, Cell Cyle, 6:13,1586-1593.*
Blelloch, et al., "Generation of Induced Pluripotent Stem Cells in the Absence of Drug Selection", 2007, Cell Stem Cell 1, pp. 245-247.
Choi, et al., "miR-34 miRNAs Provide a Barrier for Somatic Cell Reprogramming", 2011, Nature Cell Biology, vol. 13, No. 11, 17 pages.
Dimos, et al., "Induced Pluripotent Stem Cells Generated from Patients with ALS Can Be Differentiated into Motor Neurons", Science, 2008, vol. 321, pp. 1218-1221.
Maherali, et al., "Directly Reprogrammed Fibroblasts Show Global Epigenetic Remodeling and Widespread Tissue Contribution", 2007, Cell Stem Cell 1, pp. 55-70.
Maherali, et al., "Guidelines and Techniques for the Generation of Induced Pluripotent Stem Cells", 2008, Cell Stem Cell 3, pp. 595-605.
Okita, et al., "Generation of Mouse Induced Pluripotent Stem Cells Without Viral Vectors", 2008, Science, vol. 322, pp. 949-953.
Okita, et al., "Generation of Germline-Competent Induced Pluripotent Stem Cells", 2007, Nature, vol. 448, pp. 313-318.
Park, et al., "Disease-Specific Induced Pluripotent Stem Cells", 2008, Cell 134, pp. 877-886.
Stadtfeld, et al., "Defining Molecular Cornerstones During Fibroblast to iPS Cell Reprogramming in Mouse", 2008, Cell Stem Cell 2, pp. 230-240.
Takahashi, et al., "Induction of Pluripotent Stem Cells from Mouse Embryonic and Adult Fibroblast Cultures by Defined Factors", 2006, Cell 126, pp. 663-676.
Stadtfeld, et al., "Induced Pluripotent Stem Cells Generated Without Viral Integration", 2008, Science, vol. 322, pp. 945-949.
Wernig, et al., "In vitro Reprogramming of Fibroblasts into a Pluripotent ES-cell-like state", 2007, Nature, vol. 448, pp. 318-325.
Cheng, et al., "miR-34 Cooperates with p53 in Suppression of Prostate Cancer by Joint Regulation of Stem Cell Compartment", 2014, Cell Reports, vol. 6, pp. 1000-1007.
Riley, et al., "Transcriptional Control of Human p53-regulated Genes", 2008, Nature, vol. 9, pp. 402-412.
Zhao, et al., "Analysis of p53-regulated Gene Expression Patterns Using Oligonucleotide Arrays", 2000, Genes & Development, vol. 14, pp. 981-993.

* cited by examiner

*Primary Examiner* — Scott Long
*Assistant Examiner* — Arthur S Leonard
(74) *Attorney, Agent, or Firm* — Bozicevic, Field & Francis LLP; Paula A. Borden; Kyle A. Gurley

(57) ABSTRACT

The present disclosure provides a method of generating an induced pluripotent stem cell; as well as nucleic acids and genetically modified host cells useful in generating iPSCs. The present disclosure provides iPSCs, and methods of use of same.

28 Claims, 23 Drawing Sheets

Contributions of miR-34a -/- iPSCs to chimeric animals

| iPS cell line | # of injected blastocysts | # of live pups | No. of live Chimeras | Genetic background for blastocysts | Percentage of Chimerism | Germline transmission |
|---|---|---|---|---|---|---|
| miR-34a -/- iPS #1 | 20 | 9 | 3 (33%) | C57BL/6J | 50% (2/3)<br>60% (1/3) | N.D. |
| miR-34a -/- iPS #2 | 34 | 10 | 2 (20%) | C57BL/6J and C57BL/6-cBrd/cBrd/Cr | 40% (1/2)<br>35% (1/2) | N.D. |
| miR-34a -/- iPS #3 | 50 | 23 | 8 (35%) | C57BL/6-cBrd/cBrd/Cr | 10% (1/8)<br>20% (2/8)<br>40% (1/8)<br>50% (2/8)<br>60% (1/8)<br>70% (1/8) | N.D. |

FIG. 5

A
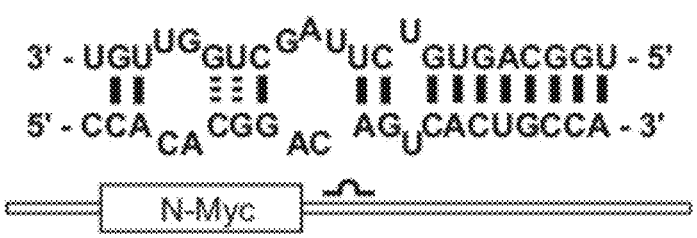
B
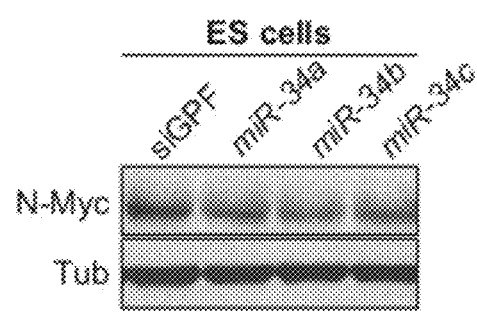
C
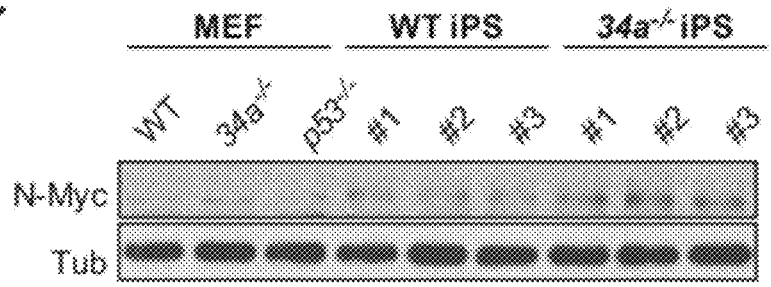
FIG. 8

Primer sequences for real time PCR analyses.

| Gene | Forward primer | SEQ ID NO: | Reverse primer | SEQ ID NO: | Reference |
|---|---|---|---|---|---|
| Nanog | AGGGTCTGCTACTGAGATGCTCTG | 59 | CAACCACTGGTTTTTCTGCCACCG | 60 | 1 |
| endogenous Sox2 | TAGAGATAGACTCCGGGCGATGA | 61 | TTGCCTTAAACAAGACCACGAAA | 62 | 36 |
| exogenous Sox2 | CTGCCCCTGTGGCACATGTG | 63 | CTTTATTTATCGTCGACC | 64 | 36 |
| endogenous Oct4 | TCTTTCCACCAGGCCCCGGCTC | 65 | TGCGGGCGGACATGGGAGATCC | 66 | 36 |
| exogenous Oct4 | TCTCCCATGCATTCAAACTG | 67 | CTTTTATTTATCGTCGACC | 68 | 36 |
| total Oct4 | CTGAGGGCCAGGCAGGAGCACGAG | 69 | CTGTAGGGAGGGCTTCGGGCACTT | 70 | 1 |
| endogenous c-myc | TAACTCGAGGAGGAGCTGGA | 71 | GCCAAGGTTGTGAGGTTAGG | 72 | 13 |
| total c-myc | CAGAGGAGGAACGAGCTGAAGCGC | 73 | TTATCCACCAGAGTTTGAAGCTTC | 74 | 1 |
| endogenous klf4 | GAATTGTGTTTCGATGATGC | 75 | TCGCTTCCTCTTCCTCCGACACA | 76 | 36 |
| exogenous klf4 | CCTTACACATGAAGAGGCAC | 77 | CTTTTATTTATCGTCGACC | 78 | 36 |
| pri-mir-34a | CTGTGCCCTCTTGCAAAACG | 79 | GGACATTCAGGTGAGGTCTTG | 80 | 14 |
| pri-mir-34b/c | GGCAGGAAGGCTCCAGATG | 81 | CCTCCACTGTTCATATGCCATTC | 82 | 14 |
| p21 | ACCGTGGAACTTTGACTTCG | 83 | CAGGGCCAGAGGAAGTACTGG | 84 | 14 |
| actin | GATCTTGGCACCACCTTCT | 85 | GGGGTGTTGAAGGTCTCAAA | 86 | 14 |

FIG. 11

GenBank NP_002692
*Homo sapiens* Oct4

```
  1 maghlasdfa fspppggggd gpggpepgwv dprtwlsfqg prggpgigpg vgrgsevwgi
 61 ppcpppyefc ggmaycgpqv gvglvpqggl etsqpegeag vgvesnsdga spepctvtpg
121 avlkekle qppeesqdik algkeleqfa klikqkritl gvtqadvglt lgvlfgkvfs
181 qttlcrfeal qlsfknmckl rplqkwvee admnenlgei ckaetlvqar krkrtslenr
241 vrgnlenlfl qqpkptlqqi shiaqqlglek khvrvrwfcn rrqkykrsss dyaqredfea
301 agspfsggpv sfplapgpph f gtpgygsphf talysvpfp egeafppvsv ttlgsgpmhsn
```

(SEQ ID NO:7)

FIG. 12A

GenBank NM_002701
*Homo sapiens* Oct4

```
   1 atggcggac acctggcttc ggatttcgcc ttctcgcccc ctccagtgtg gtgaagtgt
  61 gggccagggg ggccggagcc gggcgggtt ttgctctcgga gatcctggga ttccaaggc
 121 cctcctggag ggccaggaat cggaccggg gttggcgagg gtctgagt gtggggatt
 181 ccccgcatgc cccgcccgta tagtgtccca aggcggcttg gagacctctc agcctgaggg
 241 cgaagtgggg tcggtgggc agagcaactg agagagga cgatgggcag cctcccgag acccctggt
 301 gtcgggtgg agagcaagga ctgagaagaa tggagaagga gaagctggag cctcccgag cacccctggt
 361 gccgtgaagc tggagaagcc aagaactga gcaattgcc ctggagaag agcagaaga ggagtccca ggacatcccg
 421 gctctgcaga aggccgatgt gggccgattc cccggagaa ggacgaacgt gatgggaaga
 481 ggatacacaac cctaggacg gggggttc ctggttggaa tattggaa aaccagtgat cgagaaccga
 541 caaaacgcca tcaagcagct cggccttgga gttacagact tgaagacat gtgtaagtg
 601 cggccttgc tctgcgcgtc tgaggtctg gtggaggaa ccttcacca tgaaaatct tcaggagata
 661 tgcaaagcag aaaccctcg tgcaggccca gctgacaaca aagagaaagc cagcagccga
 721 gtgagagca accctggaga cccagcagt cagtgttcctg caggcccgca aaccacact gcagcggatc
 781 agccacatcg cccagcagccc cccagcagc ggatatgcac tcctttcctc ttccttcctc ggtctgtaac
 841 cgggccaga agggcaagga gcactcaagg gactatgcac gactatgcac ttcctccgg ggccatttt
 901 gctggtctc cttctcagg atcaagcagc tcctttcctc ttccttcctc ccctttcctc
 961 ggtaccccag gctatgggag ggaccactg cctcaactc actgaccgt actcctggt ccctttcctc
1021 gaggggggaag cctttccccc tgtctccgtc accactctgg gctctccca gcattcaaac
1081 tga
```

(SEQ ID NO:8)

FIG. 12B

GenBank NP_003097
Homo sapiens Sox2

```
  1 mynsmetelk pgepqgtsgg gggnstaaaa gggknspdr vkrpmnafmv wsrgqrrkma
 61 qenpkmhnse iskrlgaewk lletekrpf ideakrlral hmkehpdyky rprrktktlm
121 kkdkytlpgg llapggnsma sgygvgaglg agvngrndsy ahmngwsngs ysmmqdqlgy
181 pqhpglnahg aaqmqpmhry dvsalqynsm tssqtymngs ptysmsysqq gtpgmalgsm
241 gsvvksaass sppvvtssh srapcqagdl rdmismylpg aevpepaape slhmsqhyqs
301 gpvpgtaing tlplshm
```

(SEQ ID NO:9)

FIG. 13A

GenBank NM_003106
*Homo sapiens* Sox2

```
  1 atgtacaaca tgatggagac ggagctgaag ccgccgggcc cggcagcaaa ctcgggggc
 61 ggcggcggca actccaccgc ggcggcggcc ggccgcggcc agaaaacag cccgacgc
121 gtcaagcggc ccatgaatgc cttcatggtg tggtcccgcg gccagcggcg caagatggcc
181 caggagaacc ccaagatgca caactcggag atcagcaagc gcctgggcgc cgagtggaaa
241 ctttgtcgg agcggagaa gcggccgttc atcgacgagg ctaagcggct gcgagcgctg
301 cacatgaagg agcacccgga ttataaatac cggccccggc ggaaaaccaa gacgctcatg
361 aagaaggata agtacacgct gcccggcgg ctgctggcc ggcgcgtga ccagcgcat
421 agcgggggtc gggtggtga acggctggc tacagtga tgcaggacca tgcagccat
481 cgcacatga cggcagcacc cgggcctcaa tcgcacgc gcagccagc accatccctg
541 ccgcagcacc accgtgagcg cgggacctca caactcctg cacctgcagt agactgcgc agactacaca gaacggctcg
601 gacctgagcg ccctgcagta ctgtccctga gcatgcctta gccacccctg ggcatggctct tggtccatg
661 ccccacctaca cggggcgggg tcaagtccga ggcagccctc agccccagc cgggacctta tttaccca tctccccgga
721 ggttcggtgg tccaggycgg tcaagtccga cgggacctc agccccagc cgggacata tgttacctc tctccccgga
781 tccaggygcc cctgcagcg cggaaccgc ggggacctct agcccagca cggacccc tcaagcatga tctcccccgc
841 gccgaggtgc acgtgttca cggacccagc agactccag agactacaca tgtcccagca ctaccagagc
901 ggccggtgc ccggcacgc cattaacggc acactaacgga acactgccc tctcacacat gtga
```

(SEQ ID NO:10)

FIG. 13B

GenBank NP_004226
*Homo sapiens* KIN

```
  1 mrqppgesdm avsdalipsf stfasgpagr ektlrgagap nnrweelshmkrlppvlpg
 61 rpydlaaatv atdlesggag aacggsnlap ipreteefn dildldflls nslthppesv
121 aatvsssasa ssssspsssg pasapatcsf typlragndp gvapgytggp llygresapp
181 ptapfnladi ndvspsggfv sellrpelqp vylppqgpqp pgggimgkfv lkaslsapgs
241 eygspsvlsv skgspdgshp vvvapyngqp prtcpklkqs avsscthlga gpplsnghrp
301 aahdfplgcq lpsrttptlg leevlssrdc hpalplppgf hphpgpmyps flpdqmqpqv
361 pplhygelmp pgscmpeepk pkrgrrswpr krtathtchy agcgktytks shlkahlrth
421 tgekpyhcdw dgcgwkfars deltrhyrkh tgrpfqcgk cdrafsredh lalhmkrhf
```

(SEQ ID NO:11)

FIG. 14A

GenBank NM_004235
*Homo sapiens* Klf4

```
   1 atgaggcagc cacctggcga gtctgacatg gctgtcagcg acgcgctgct cccatctttc
  61 tccacgttcg cgtctggctc ggcgggaagg gctctcccac tgcgtcaagc aggtgcccg
 121 aataacccgt ggcgggagga gctctcccac atgaagcgac ttccccagt gcttccggc
 181 cgcccctatg acctggcggc ggcgacagcc gccacagaca ctgagagcgg cggagcccgt
 241 gcggcttgcg gcgtagcaa cctggcgccc ctacctcgga gagagaccga gtagttcaac
 301 gatctcccga acctggactt tattctccca aatcgctga ccatcctcg ggagtcagtg
 361 gcgcaaccg tgcctctgtc agtcagcg tccttttgt cgtgcgtc gagcagcggc
 421 cctgccaccg cgtgccccca ctgcagctc acttatccga tcgggccggg gaagaccg
 481 ggcgtgcgc cggaccgcac gggcgggagc ctctctatg gcaggagtc cgctccct
 541 ccgacggtc ccttcaacct gccacaatc aacgacgtga gccacgcga cgcttcgtg
 601 gccagctcc attgaccgg gtgtacattc cgccgagca gccgcagcg ccctgcagc
 661 ccaggtgcg ggctgatgg caagttgtgt ctgaaggcgt cgctgagcgc ccctgcacgc
 721 gagtacggca catccacgg catcacgcga agcagaggca gcctgacac caaggaggag
 781 gtgttgtgtg cgggcccgga cggggcgcat ccttggcpa ccgccaagat ccaagaagag
 841 gcgttctctt cgtgcaccca ctttggcgct cttggcgt gaccccct tcacgaatgg gacctggg
 901 gctgcacacg acttcccct ggcaccgag ctcccccagc agactaccc tgccgcttc
 961 cttgaggaag tgctgagcag caggacttgt ttctcacctc caccctgccc atggatgcag
1021 catcccccac ccggccgctc ttaaccaaga gctcatgca cccggttcct gcatgccaga
1081 ccgccgctcc attaccaaga gaaagcatca gtggcccgga cccgttcct ggagcccaag
1141 ccaaagaggg gaagacgatc gtgcccggg aaaaggaccg tccatctca gcgaaccac
1201 gcgggctgca caaaacctca cacaaagagt cacaaagct aggcactcaa gcgacccac
1261 acaggtgaga aaccttacca ctgtgactgg gacgctgtg gatggaatt cgcccgctca
1321 gatgaactga cgggcccaga cgtaaacaca acggggcac gccgttcca gtgccaaaaa
1381 tgcggaccgag catttccag cgtcggccac ctcgccttac acatgaagag gcattttaa
```

(SEQ ID NO:12)

FIG. 14B

GenBank NP_002458
*Homo sapiens* cMyc

```
  1  mdffrveng qppatmpinv sftnrnydld ydsvqpyfyc deeenfyqqq qqselqppap
 61  sediwkkfel lptppispsr rsglcspsyv avtpfslrgd ndgggsfst  adqlemvtel
121  lggdmvngsf icdpddetfi knilgdcmw  sgfsaaaklv seklasygaa rkdsgpnpa
181  rghsvcstss lylqdlsaaa secidpsvvf pyplndsssp kscasqdssa fspssdsll  
241  stesspqgsp eplvlheetp pttssdseee qedaeeeidvv qedaeeidvv rkdyppakrv  
301  qnskpphspl vlkrchvsth qhnyaappst rkdyppaakrv klasvrvlrq isnnrkctsp
361  rssdteenvk rrthnvleeq rrnelkrsff alrdqlpele nnekapkvvl lkkatayils
421  vqaaeqklis eedllrkrre qlkhkleqlr nsca
```

(SEQ ID NO: 13)

FIG. 15A

GenBank NM_002467
*Homo sapiens* cMYC

```
   1 ctggatttt ttcggtagt ggaaaaccag cagcctcccg cgacgatgcc cctcaacgtt
  61 agcttcacca acaggaacta tgacctcgac tacgactcgg tgcagccgta ttctactgc
 121 gacgaggagg agaacttcta ccagcagcag cagcagagcg agctgcagcc cgcagcgcag
 181 agggagagata tctggagagc atcgagctgc ctggccacc ctgcccctgt cgcctagcgc
 241 cgtccgggc tctgtcgccg gagggaagg ctcctcgtt gcggtcacac cttctcccct
 301 aacgacggcg gtggcggga gtgcggagg gcttccaacg tggagaggtt gaccgagctg
 361 ctgggagag acatgtgaa ccaggagttc cgccagtcc atctgcagc gaccgagctc
 421 aaaaacatca tcatccagga ctgtatgtgg agcggcttct cggcaagca ccgcaagctc
 481 tcagagagc tggccctgc cccagctgc cgcaaagaca ggcaggaccc cgaaccgccc
 541 cgcggcacc ggcgtcctgc caccctcctc cacgtcacc gcgccgccgc tgcgccgcgc
 601 tcagagtgca gctggtgtc gtgttgctc gtgtgttcc cctcccgt cagctcccc
 661 aagtccctgc cctccccgca gggcagaga gggcccttc ttctctccgt tgctgctcct
 721 tcgacggagt ccctccccga ggcgagactc tgaggagaa caagaagatg cctgtcctga
 781 cccccaccca gcagcagctca tggaggcaaa caaagaagt ctggaatcac ctgatcaccg
 841 tctgtggaa agagcagagt cctggcaaag agcgaactt acaacgtctt ggagcgccag
 901 ggcacagca aacctcctca cagcccacaa gccctgcgtc accagatcc gacagtgtt
 961 cagcacaact acgcagcgcc tcctcaact cggaaggact ccgaaggtcc catcctgtcc
1021 aagttggaca gtgtcagagt cctgagacag atcagcaaca accgaaaatg caagaggtc
1081 aggtcctcgg acaccgagga aatgtcaag aggcgaacac acaacgtctt ggagcgccag
1141 aggaggaaacg agctaaaacg gagctttttt gccctgcgtg accagatccc ggagttggaa
1201 aacaatgaaa aggcccaactc ctagcaagct ggagttatc cttagttatc catcctgtcc
1261 gtccaagcag aggagcaaa gctaaaatct gaagaggact tgttgcggaa tgttggggaa
1321 cagttgaaac acaaacttga acagctacgg aacttgtgt cgtaa
```

FIG. 15B (SEQ ID NO:14)

miR-34a stem-loop
5'-GGCCAGCUGUGAGUGUUUCUUUGGCAGUGUCUUAGCUGGUUGUUGUGAGCAAUAGUAAGGAAGCAAUCAGCAAGU
AUACUGCCCUAGAAGUGCUGCACGUUGUGGGGCCC-3' (SEQ ID NO:2)

FIG. 16A miR-34a mature
5'- UGGCAGUGUCUUAGCUGGUUGU-3' (SEQ ID NO:1)

FIG. 16B miR-34b stem loop
5'- GUGCUCGGUUUGUAGGCAGUGUCAUUAGCUGAUUGUACUGUGGUGGUUACAAUCACUAACUCCACUGCCAUCAAAACAAGGCAC-3' (SEQ ID NO:4)

FIG. 17A miR-34b mature
5'- CAAUCACUAACUCCACUGCCAU-3' (SEQ ID NO:3)

FIG. 17B miR-34c stem-loop
5'- AGGCAGUGUAGUUAGCUGAUUGCUAAUAGUACCAAUCACUAACCACACGGCCAGGUAAAAAGAUU-3' (SEQ ID NO:6)

FIG. 18A miR-34c mature
5'- AGGCAGUGUAGUUAGCUGAUUGC-3' (SEQ ID NO:5)

FIG. 18B

SEQUENCE LISTING

<160> NUMBER OF SEQ ID NOS: 86

<210> SEQ ID NO 1
<211> LENGTH: 22
<212> TYPE: RNA
<213> ORGANISM: Homo sapiens

<400> SEQUENCE: 1
uggcaguguc uuagcugguu gu                                              22

<210> SEQ ID NO 2
<211> LENGTH: 110
<212> TYPE: RNA
<213> ORGANISM: Homo sapiens

<400> SEQUENCE: 2
ggccagcugu gaguguuucu uuggcagugu cuuagcuggu uguugugagc aauaguaagg     60
aagcaaucag caaguauacu gcccuagaag ugcugcacgu ugugggccc                110

<210> SEQ ID NO 3
<211> LENGTH: 22
<212> TYPE: RNA
<213> ORGANISM: Homo sapiens

<400> SEQUENCE: 3
caaucacuaa cuccacugcc au                                              22

<210> SEQ ID NO 4
<211> LENGTH: 84
<212> TYPE: RNA
<213> ORGANISM: Homo sapiens

<400> SEQUENCE: 4
gugcucgguu uguaggcagu gucauuagcu gauuguacug gguggguuac aaucacuaac     60
uccacugcca ucaaaacaag gcac                                            84

<210> SEQ ID NO 5
<211> LENGTH: 23
<212> TYPE: RNA
<213> ORGANISM: Homo sapiens

<400> SEQUENCE: 5
aggcagugua guuagcugau ugc                                             23

<210> SEQ ID NO 6
<211> LENGTH: 77
<212> TYPE: RNA
<213> ORGANISM: Homo sapiens

<400> SEQUENCE: 6
agucuaguua cuaggcagug uaguuagcug auugcuaaua guaccaauca cuaaccacac     60
ggccagguaa aaagauu                                                    77

<210> SEQ ID NO 7
<211> LENGTH: 360
<212> TYPE: PRT
<213> ORGANISM: Homo sapiens

<400> SEQUENCE: 7

Met Ala Gly His Leu Ala Ser Asp Phe Ala Phe Ser Pro Pro Pro Gly
1               5                   10                  15

```
Gly Gly Gly Asp Gly Pro Gly Pro Glu Pro Gly Trp Val Asp Pro
            20              25              30
Arg Thr Trp Leu Ser Phe Gln Gly Pro Gly Gly Pro Gly Ile Gly
        35              40              45
Pro Gly Val Gly Pro Gly Ser Glu Val Trp Gly Ile Pro Pro Cys Pro
50              55              60
Pro Pro Tyr Glu Phe Cys Gly Gly Met Ala Tyr Cys Gly Pro Gln Val
65              70              75              80
Gly Val Gly Leu Val Pro Gln Gly Gly Leu Thr Ser Gln Pro Glu
            85              90              95
Gly Glu Ala Gly Val Gly Val Ser Asn Ser Asp Gly Ala Ser Pro
        100             105             110
Glu Pro Cys Thr Val Thr Pro Gly Ala Val Lys Leu Glu Lys Glu Lys
        115             120             125
Leu Glu Gln Asn Pro Glu Glu Ser Gln Asp Ile Lys Ala Leu Gln Lys
130             135             140
Glu Leu Glu Gln Phe Ala Lys Leu Leu Lys Gln Lys Arg Ile Thr Leu
145             150             155             160
Gly Tyr Thr Gln Ala Asp Val Gly Leu Thr Leu Gly Val Leu Phe Gly
            165             170             175
Lys Val Phe Ser Gln Thr Thr Ile Cys Arg Phe Glu Ala Leu Gln Leu
            180             185             190
Ser Phe Lys Asn Met Cys Lys Leu Arg Pro Leu Leu Gln Lys Trp Val
        195             200             205
Glu Glu Ala Asp Asn Asn Glu Asn Leu Gln Glu Ile Cys Lys Ala Glu
210             215             220
Thr Leu Val Gln Ala Arg Lys Arg Lys Arg Thr Ser Ile Glu Asn Arg
225             230             235             240
Val Arg Gly Asn Leu Glu Asn Leu Phe Leu Gln Cys Pro Lys Pro Thr
            245             250             255
Leu Gln Gln Ile Ser His Ile Ala Gln Gln Leu Gly Leu Glu Lys Asp
        260             265             270
Val Val Arg Val Trp Phe Cys Asn Arg Arg Gln Lys Gly Lys Arg Ser
        275             280             285
Ser Ser Asp Tyr Ala Gln Arg Glu Asp Phe Glu Ala Ala Gly Ser Pro
290             295             300
Phe Ser Gly Gly Pro Val Ser Phe Pro Leu Ala Pro Gly Pro His Phe
305             310             315             320
Gly Thr Pro Gly Tyr Gly Ser Pro His Phe Thr Ala Leu Tyr Ser Ser
            325             330             335
Val Pro Phe Pro Glu Gly Glu Ala Phe Pro Pro Val Ser Val Thr Thr
        340             345             350
Leu Gly Ser Pro Met His Ser Asn
        355             360

<210> SEQ ID NO 8
<211> LENGTH: 1083
<212> TYPE: DNA
<213> ORGANISM: Homo sapiens

<400> SEQUENCE: 8
atggcgggac acctggcttc ggatttcgcc ttctcgcccc ctccaggtgg tggaggtgat      60
gggccagggg ggccggagcc gggctgggtt gatcctcgga cctggctaag cttccaaggc     120
cctcctggag ggccaggaat cgggccgggg gttgggccag ctctgaggt gtggggatt      180
```

```
cccccatgcc cccgccgta tgagttctgt gggggatgg cgtactgtgg gccccaggtt    240 ggagtgggc tagtgcccca aggcggcttg agacctctc agcctgaggg cgaagcagga    300 gtcgggtgg agagcaactc cgatgggcc tccccggagc cctgcaccgt caccctggt    360 gccgtgaagc tggagaagga gaagctggag caaaacccgg aggagtccca ggacatcaaa    420
gctctgcaga agaactcga gcaatttgcc aagctcctga agcagaagag gatcaccctg    480
ggatatacac aggccgatgt ggggctcacc ctgggggttc tatttgggaa ggtattcagc    540
caaacgacca tctgccgctt tgaggctctg cagcttagct tcaagaacat gtgtaagctg    600
cggcccttgc tgcagaagtg ggtggaggaa gctgacaaca atgaaaatct tcaggagata    660
tgcaaagcag aaaccctcgt gcaggcccga agagaaagc gaaccagtat cgagaaccga    720
gtgagaggca acctggagaa tttgttcctg cagtgcccga aacccacact gcagcagatc    780
agccacatcg cccagcagct tgggctcgag aaggatgtgg tccgagtgtg gttctgtaac    840
cggcgccaga agggcaagcg atcaagcagc gactatgcac aacgagagga ttttgaggct    900
gctgggtctc ctttctcagg gggaccagtg tcctttcctc tggccccagg gccccatttt    960
ggtaccccag gctatgggag ccctcacttc actgcactgt actcctcggt ccctttccct    1020 gaggggaag ccttctcccc tgtctccgtc accactctgg gctctcccat gcattcaaac    1080
tga                                                                 1083
```

<210> SEQ ID NO 9
<211> LENGTH: 317
<212> TYPE: PRT
<213> ORGANISM: Homo sapiens

<400> SEQUENCE: 9

```
Met Tyr Asn Met Met Glu Thr Glu Leu Lys Pro Pro Gly Pro Gln Gln
1               5                   10                  15

Thr Ser Gly Gly Gly Gly Gly Asn Ser Thr Ala Ala Ala Ala Gly Gly
            20                  25                  30

Asn Gln Lys Asn Ser Pro Asp Arg Val Lys Arg Pro Met Asn Ala Phe
        35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
    130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
        195                 200                 205
```

```
Ser Met Thr Ser Ser Gln Thr Tyr Met Asn Gly Ser Pro Thr Tyr Ser
    210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Pro Pro Val Val Thr
                245                 250                 255

Ser Ser Ser His Ser Arg Ala Pro Cys Gln Ala Gly Asp Leu Arg Asp
                260                 265                 270

Met Ile Ser Met Tyr Leu Pro Gly Ala Glu Val Pro Glu Pro Ala Ala
            275                 280                 285

Pro Ser Arg Leu His Met Ser Gln His Tyr Gln Ser Gly Pro Val Pro
    290                 295                 300

Gly Thr Ala Ile Asn Gly Thr Leu Pro Leu Ser His Met
305                 310                 315
```

<210> SEQ ID NO 10
<211> LENGTH: 954
<212> TYPE: DNA
<213> ORGANISM: Homo sapiens

<400> SEQUENCE: 10

```
atgtacaaca tgatggagac ggagctgaag ccgccgggcc cgcagcaaac ttcgggggc      60
ggcggcggca actccaccgc ggcggcggcc ggcggcaacc agaaaaacag cccggaccgc    120
gtcaagcggc ccatgaatgc cttcatggtg tggtcccgcg gcagcggcg caagatggcc     180
caggagaacc ccaagatgca caactcggag atcagcaagc gcctgggcgc cgagtggaaa    240
cttttgtcgg agacggagaa gcggccgttc atcgacgagg ctaagcggct gcgagcgctg    300
cacatgaagg agcaccccgga ttataaatac cggccccggc ggaaaaccaa gacgctcatg    360
aagaaggata gtacacgct gcccggcggg ctgctggccc ccggcggcaa tagcatggcg    420
agcggggtcg ggtgggcgc cggcctgggc gcgggcgtga accagcgcat ggacagttac    480
gcgcacatga acggctggag caacggcagc tacagcatga tgcaggacca gctgggctac    540
ccgcagcacc cgggcctcaa tgcgcacggc gcagcgcaga tgcagcccat gcaccgctac    600
gacgtgagcg ccctgcagta caactccatg accagctcgc agacctacat gaacggctcg    660
cccacctaca gcatgtccta ctcgcagcag ggcaccctg gcatggctct tggctccatg    720
ggttcggtgg tcaagtccga ggccagctcc agcccccctg tggttacctc ttcctccac    780
tccagggcgc cctgccaggc cggggacctc cgggacatga tcagcatgta tctccccggc    840
gccgaggtgc cggaacccgc cgcccccagc agacttcaca tgtcccagca ctaccagagc    900
ggcccggtgc ccggcacggc cattaacggc acactgcccc tctcacacat gtga          954
```

<210> SEQ ID NO 11
<211> LENGTH: 479
<212> TYPE: PRT
<213> ORGANISM: Homo sapiens

<400> SEQUENCE: 11

```
Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
                20                  25                  30

Thr Leu Arg Gln Ala Gly Ala Pro Asn Asn Arg Trp Arg Glu Glu Leu
            35                  40                  45
```

```
Ser His Met Lys Arg Leu Pro Pro Val Leu Pro Gly Arg Pro Tyr Asp
    50              55                  60
Leu Ala Ala Ala Thr Val Ala Thr Asp Leu Glu Ser Gly Gly Ala Gly
65              70                  75                  80
Ala Ala Cys Gly Gly Ser Asn Leu Ala Pro Leu Pro Arg Arg Glu Thr
                85                  90                  95
Glu Glu Phe Asn Asp Leu Leu Asp Leu Asp Phe Ile Leu Ser Asn Ser
                100                 105                 110
Leu Thr His Pro Pro Glu Ser Val Ala Ala Thr Val Ser Ser Ser Ala
            115                 120                 125
Ser Ala Ser Ser Ser Ser Pro Ser Ser Gly Pro Ala Ser Ala
130                 135                 140
Pro Ser Thr Cys Ser Phe Thr Tyr Pro Ile Arg Ala Gly Asn Asp Pro
145                 150                 155                 160
Gly Val Ala Pro Gly Gly Thr Gly Gly Gly Leu Leu Tyr Gly Arg Glu
                165                 170                 175
Ser Ala Pro Pro Thr Ala Pro Phe Asn Leu Ala Asp Ile Asn Asp
                180                 185                 190
Val Ser Pro Ser Gly Gly Phe Val Ala Glu Leu Leu Arg Pro Glu Leu
            195                 200                 205
Asp Pro Val Tyr Ile Pro Pro Gln Gln Pro Gln Pro Gly Gly Gly
210                 215                 220
Leu Met Gly Lys Phe Val Leu Lys Ala Ser Leu Ser Ala Pro Gly Ser
225                 230                 235                 240
Glu Tyr Gly Ser Pro Ser Val Ile Ser Val Ser Lys Gly Ser Pro Asp
                245                 250                 255
Gly Ser His Pro Val Val Val Ala Pro Tyr Asn Gly Gly Pro Pro Arg
            260                 265                 270
Thr Cys Pro Lys Ile Lys Gln Glu Ala Val Ser Ser Cys Thr His Leu
            275                 280                 285
Gly Ala Gly Pro Pro Leu Ser Asn Gly His Arg Pro Ala Ala His Asp
290                 295                 300
Phe Pro Leu Gly Arg Gln Leu Pro Ser Arg Thr Thr Pro Thr Leu Gly
305                 310                 315                 320
Leu Glu Glu Val Leu Ser Ser Arg Asp Cys His Pro Ala Leu Pro Leu
                325                 330                 335
Pro Pro Gly Phe His Pro His Pro Gly Pro Asn Tyr Pro Ser Phe Leu
                340                 345                 350
Pro Asp Gln Met Gln Pro Gln Val Pro Pro Leu His Tyr Gln Glu Leu
            355                 360                 365
Met Pro Pro Gly Ser Cys Met Pro Glu Glu Pro Lys Pro Lys Arg Gly
370                 375                 380
Arg Arg Ser Trp Pro Arg Lys Arg Thr Ala Thr His Thr Cys Asp Tyr
385                 390                 395                 400
Ala Gly Cys Gly Lys Thr Tyr Thr Lys Ser Ser His Leu Lys Ala His
                405                 410                 415
Leu Arg Thr His Thr Gly Glu Lys Pro Tyr His Cys Asp Trp Asp Gly
            420                 425                 430
Cys Gly Trp Lys Phe Ala Arg Ser Asp Glu Leu Thr Arg His Tyr Arg
                435                 440                 445
Lys His Thr Gly His Arg Pro Phe Gln Cys Gln Lys Cys Asp Arg Ala
450                 455                 460
Phe Ser Arg Ser Asp His Leu Ala Leu His Met Lys Arg His Phe
```

<210> SEQ ID NO 12
<211> LENGTH: 1440
<212> TYPE: DNA
<213> ORGANISM: Homo sapiens

<400> SEQUENCE: 12

```
atgaggcagc cacctggcga gtctgacatg gctgtcagcg acgcgctgct cccatctttc    60
tccacgttcg cgtctggccc ggcgggaagg gagaagacac tgcgtcaagc aggtgccccg   120
aataaccgct ggcgggagga gctctcccac atgaagcgac ttccccccagt gcttcccggc   180
cgccccctatg acctggcggc ggcgaccgtg gccacagacc tggagagcgg cggagccggt   240
gcggcttgcg cgcgtagcaa cctggcgccc ctacctcgga gagagaccga ggagttcaac   300
gatctcctgg acctggactt tattctctcc aattcgctga cccatcctcc ggagtcagtg   360
gccgccaccg tgtcctcgtc agcgtcagcc tcctcttcgt cgtcgccgtc gagcagcggc   420
cctgccagcg cgccctccac ctgcagcttc acctatccga tccgggccgg aacgaccccg   480
ggcgtggcgc cgggcggcac gggcggaggc ctcctctatg cagggagtc cgctcccct    540
ccgacggctc ccttcaacct ggcggacatc aacgacgtga cccctcgggg cggcttcgtg   600
gccgagctcc tgcggccaga attggacccg gtgtacattc cgccgcagca gccgcagccg   660
ccaggtggcg gctgatgggg caagttcgtg ctgaaggcgt cgctgagcgc ccctggcagc   720
gagtacggca gcccgtcggt catcagcgtc agcaaaggca gccctgacgg cagccacccg   780
gtggtggtgg cgccctacaa cggcgggccg ccgcgcacgt gccccaagat caagcaggag   840
gcggtctctt cgtgcaccca cttgggcgct ggaccccctc tcagcaatgg ccaccggccg   900
gctgcacacg acttccccct ggggcggcag ctccccagca ggactacccc gaccctgggt   960
cttgaggaag tgctgagcag cagggactgt caccctgccc tgccgcttcc tcccggcttc  1020
catccccacc cggggcccaa ttacccatcc ttcctgcccg atcagatgca gccgcaagtc  1080
ccgccgctcc attaccaaga gctcatgcca cccggttcct gcatgccaga ggagcccaag  1140
ccaaagaggg gaagacgatc gtggcccggg aaaaggaccg ccacccacac ttgtgattac  1200
gcgggctgcg gcaaaaccta cacaaagagt tccatctca aggcacacct gcgaacccac  1260
acaggtgaga aaccttacca ctgtgactgg gacggctgtg gatggaaatt cgcccgctca  1320
gatgaactga ccaggcacta ccgtaaacac acggggcacc gcccgttcca gtgccaaaaa  1380
tgcgaccgag cattttccag gtcggaccac ctcgccttac acatgaagag catttttaa  1440
```

<210> SEQ ID NO 13
<211> LENGTH: 454
<212> TYPE: PRT
<213> ORGANISM: Homo sapiens

<400> SEQUENCE: 13

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
                20                  25                  30

Ser Val Gln Pro Tyr Phe Tyr Cys Asp Glu Glu Asn Phe Tyr Gln
            35                  40                  45

Gln Gln Gln Gln Ser Glu Leu Gln Pro Pro Ala Pro Ser Glu Asp Ile
        50                  55                  60

Trp Lys Lys Phe Glu Leu Leu Pro Thr Pro Pro Leu Ser Pro Ser Arg

```
            65                  70                  75                  80
        Arg Ser Gly Leu Cys Ser Pro Ser Tyr Val Ala Val Thr Pro Phe Ser
                        85                  90                  95

Leu Arg Gly Asp Asn Asp Gly Gly Gly Ser Phe Ser Thr Ala Asp
                        100                 105             110

Gln Leu Glu Met Val Thr Glu Leu Gly Gly Asp Met Val Asn Gln
                        115                 120             125

Ser Phe Ile Cys Asp Pro Asp Glu Thr Phe Ile Lys Asn Ile Ile
                130                 135                 140

Ile Gln Asp Cys Met Trp Ser Gly Phe Ser Ala Ala Lys Leu Val
        145                 150                 155                 160

Ser Glu Lys Leu Ala Ser Tyr Gln Ala Ala Arg Lys Asp Ser Gly Ser
                        165                 170                 175

Pro Asn Pro Ala Arg Gly His Ser Val Cys Ser Thr Ser Leu Tyr
                        180                 185                 190

Leu Gln Asp Leu Ser Ala Ala Ser Glu Cys Ile Asp Pro Ser Val
                        195                 200                 205

Val Phe Pro Tyr Pro Leu Asn Asp Ser Ser Pro Lys Ser Cys Ala
                210                 215                 220

Ser Gln Asp Ser Ser Ala Phe Ser Pro Ser Ser Asp Ser Leu Leu Ser
        225                 230                 235                 240

Ser Thr Glu Ser Ser Pro Gln Gly Ser Pro Glu Pro Leu Val Leu His
                        245                 250                 255

Glu Glu Thr Pro Pro Thr Thr Ser Ser Asp Ser Glu Glu Gln Glu
                        260                 265                 270

Asp Glu Glu Glu Ile Asp Val Val Ser Val Glu Lys Arg Gln Ala Pro
                275                 280                 285

Gly Lys Arg Ser Glu Ser Gly Ser Pro Ser Ala Gly Gly His Ser Lys
                290                 295                 300

Pro Pro His Ser Pro Leu Val Leu Lys Arg Cys His Val Ser Thr His
        305                 310                 315                 320

Gln His Asn Tyr Ala Ala Pro Pro Ser Thr Arg Lys Asp Tyr Pro Ala
                        325                 330                 335

Ala Lys Arg Val Lys Leu Asp Ser Val Arg Val Leu Arg Gln Ile Ser
                        340                 345                 350

Asn Asn Arg Lys Cys Thr Ser Pro Arg Ser Ser Asp Thr Glu Glu Asn
                        355                 360                 365

Val Lys Arg Arg Thr His Asn Val Leu Glu Arg Gln Arg Arg Asn Glu
                370                 375                 380

Leu Lys Arg Ser Phe Phe Ala Leu Arg Asp Gln Ile Pro Glu Leu Glu
        385                 390                 395                 400

Asn Asn Glu Lys Ala Pro Lys Val Val Ile Leu Lys Lys Ala Thr Ala
                        405                 410                 415

Tyr Ile Leu Ser Val Gln Ala Glu Glu Gln Lys Leu Ile Ser Glu Glu
                        420                 425                 430

Asp Leu Leu Arg Lys Arg Arg Glu Gln Leu Lys His Lys Leu Glu Gln
                        435                 440                 445

Leu Arg Asn Ser Cys Ala
                450

<210> SEQ ID NO 14
<211> LENGTH: 1365
<212> TYPE: DNA
<213> ORGANISM: Homo sapiens
```

-continued

```
<400> SEQUENCE: 14
ctggattttt ttcgggtagt ggaaaaccag cagcctcccg cgacgatgcc cctcaacgtt      60
agcttcacca acaggaacta tgacctcgac tacgactcgg tgcagccgta tttctactgc     120
gacgaggagg agaacttcta ccagcagcag cagcagagcg agctgcagcc cccggcgccc     180
agcgaggata tctggaagaa attcgagctg ctgcccaccc cgccctgtc ccctagccgc      240 cgctccgggc tctgctcgcc ctcctacgtt gcggtcacac ccttctccct tcggggagac     300
aacgacggcg gtggcgggag cttctccacg gccgaccagc tggagatggt gaccgagctg     360
ctgggaggag acatggtgaa ccagagtttc atctgcgacc cggacgacga gaccttcatc     420
aaaaacatca tcatccagga ctgtatgtgg agcggcttct cggccgccgc caagctcgtc     480
tcagagaagc tggcctccta ccaggctgcg cgcaaagaca gcggcagccc gaaccccgcc     540
cgcggccaca gcgtctgctc cacctccagc ttgtacctgc aggatctgag cgccgccgcc     600
tcagagtgca tcgaccctc ggtggtcttc ccctaccctc tcaacgacag cagctcgccc     660
aagtcctgcg cctcgcaaga ctccagcgcc ttctctccgt cctcggattc tctgctctcc     720
tcgacggagt cctccccgca gggcagcccc gagcccctgg tgctccatga ggagacaccg     780
cccaccacca gcagcgactc tgaggaggaa caagaagatg aggaagaaat cgatgttgtt     840
tctgtggaaa agaggcaggc tcctggcaaa aggtcagagt ctggatcacc ttctgctgga     900
ggccacagca aacctcctca gcccactg gtcctcaaga ggtgccacgt ctccacacat      960
cagcacaact acgcagcgcc tcccccact cggaaggact atcctgctgc aagagggtc     1020 aagttggaca gtgtcagagt cctgagacag atcagcaaca accgaaaatg caccagcccc    1080
aggtcctcgg acaccgagga gaatgtcaag aggcgaacac acaacgtctt ggagcgccag    1140
aggaggaacg agctaaaacg gagctttttt gccctgcgtg accagatccc ggagttggaa    1200
aacaatgaaa aggcccccaa ggtagttatc cttaaaaaag ccacagcata catcctgtcc    1260
gtccaagcag aggagcaaaa gctcatttct gaagaggact tgttgcggaa acgacgagaa    1320 cagttgaaaac acaaacttga acagctacgg aactcttgtg cgtaa                   1365
```

<210> SEQ ID NO 15
<211> LENGTH: 11
<212> TYPE: PRT
<213> ORGANISM: Artificial sequence
<220> FEATURE:
<223> OTHER INFORMATION: Synthetic peptide

<400> SEQUENCE: 15

Tyr Gly Arg Lys Lys Arg Arg Gln Arg Arg Arg
1               5                   10

<210> SEQ ID NO 16
<211> LENGTH: 12
<212> TYPE: PRT
<213> ORGANISM: Artificial sequence
<220> FEATURE:
<223> OTHER INFORMATION: Synthetic peptide

<400> SEQUENCE: 16

Arg Arg Gln Arg Arg Thr Ser Lys Leu Met Lys Arg
1               5                   10

<210> SEQ ID NO 17
<211> LENGTH: 27
<212> TYPE: PRT

```
<213> ORGANISM: Artificial sequence
<220> FEATURE:
<223> OTHER INFORMATION: Synthetic peptide

<400> SEQUENCE: 17

Gly Trp Thr Leu Asn Ser Ala Gly Tyr Leu Leu Gly Lys Ile Asn Leu
1               5                   10                  15
Lys Ala Leu Ala Ala Leu Ala Lys Lys Ile Leu
            20                  25

<210> SEQ ID NO 18
<211> LENGTH: 33
<212> TYPE: PRT
<213> ORGANISM: Artificial sequence
<220> FEATURE:
<223> OTHER INFORMATION: Synthetic peptide

<400> SEQUENCE: 18

Lys Ala Leu Ala Trp Glu Ala Lys Leu Ala Lys Ala Leu Ala Lys Ala
1               5                   10                  15
Leu Ala Lys His Leu Ala Lys Ala Leu Ala Lys Ala Leu Lys Cys Glu
            20                  25                  30
Ala

<210> SEQ ID NO 19
<211> LENGTH: 16
<212> TYPE: PRT
<213> ORGANISM: Artificial sequence
<220> FEATURE:
<223> OTHER INFORMATION: Synthetic peptide

<400> SEQUENCE: 19

Arg Gln Ile Lys Ile Trp Phe Gln Asn Arg Arg Met Lys Trp Lys Lys
1               5                   10                  15

<210> SEQ ID NO 20
<211> LENGTH: 9
<212> TYPE: PRT
<213> ORGANISM: Artificial sequence
<220> FEATURE:
<223> OTHER INFORMATION: Synthetic peptide

<400> SEQUENCE: 20

Arg Lys Lys Arg Arg Gln Arg Arg Arg
1               5

<210> SEQ ID NO 21
<211> LENGTH: 11
<212> TYPE: PRT
<213> ORGANISM: Artificial sequence
<220> FEATURE:
<223> OTHER INFORMATION: Synthetic peptide

<400> SEQUENCE: 21

Tyr Ala Arg Ala Ala Ala Arg Gln Ala Arg Ala
1               5                   10

<210> SEQ ID NO 22
<211> LENGTH: 11
<212> TYPE: PRT
<213> ORGANISM: Artificial sequence
<220> FEATURE:
<223> OTHER INFORMATION: Synthetic peptide

<400> SEQUENCE: 22
```

Thr His Arg Leu Pro Arg Arg Arg Arg Arg
1               5                   10

<210> SEQ ID NO 23
<211> LENGTH: 11
<212> TYPE: PRT
<213> ORGANISM: Artificial sequence
<220> FEATURE:
<223> OTHER INFORMATION: Synthetic peptide

<400> SEQUENCE: 23

Gly Gly Arg Arg Ala Arg Arg Arg Arg Arg
1               5                   10

<210> SEQ ID NO 24
<211> LENGTH: 22
<212> TYPE: DNA
<213> ORGANISM: Artificial sequence
<220> FEATURE:
<223> OTHER INFORMATION: Synthetic DNA

<400> SEQUENCE: 24
acaaccagct aagacactgc ca                                              22

<210> SEQ ID NO 25
<211> LENGTH: 21
<212> TYPE: DNA
<213> ORGANISM: Artificial sequence
<220> FEATURE:
<223> OTHER INFORMATION: Synthetic DNA

<400> SEQUENCE: 25
caaccagcta agacactgcc a                                               21

<210> SEQ ID NO 26
<211> LENGTH: 21
<212> TYPE: DNA
<213> ORGANISM: Artificial sequence
<220> FEATURE:
<223> OTHER INFORMATION: Synthetic DNA

<400> SEQUENCE: 26
acaaccagct aagacactgc c                                               21

<210> SEQ ID NO 27
<211> LENGTH: 20
<212> TYPE: DNA
<213> ORGANISM: Artificial sequence
<220> FEATURE:
<223> OTHER INFORMATION: Synthetic DNA

<400> SEQUENCE: 27
aaccagctaa gacactgcca                                                 20

<210> SEQ ID NO 28
<211> LENGTH: 20
<212> TYPE: DNA
<213> ORGANISM: Artificial sequence
<220> FEATURE:
<223> OTHER INFORMATION: Synthetic DNA

<400> SEQUENCE: 28
acaaccagct aagacactgc                                                 20

<210> SEQ ID NO 29
<211> LENGTH: 22

```
<212> TYPE: DNA
<213> ORGANISM: Artificial sequence
<220> FEATURE:
<223> OTHER INFORMATION: Synthetic DNA

<400> SEQUENCE: 29
atggcagtgg agttagtgat tg                                              22

<210> SEQ ID NO 30
<211> LENGTH: 21
<212> TYPE: DNA
<213> ORGANISM: Artificial sequence
<220> FEATURE:
<223> OTHER INFORMATION: Synthetic DNA

<400> SEQUENCE: 30
tggcagtgga gttagtgatt g                                               21

<210> SEQ ID NO 31
<211> LENGTH: 21
<212> TYPE: DNA
<213> ORGANISM: Artificial sequence
<220> FEATURE:
<223> OTHER INFORMATION: Synthetic DNA

<400> SEQUENCE: 31
atggcagtgg agttagtgat t                                               21

<210> SEQ ID NO 32
<211> LENGTH: 20
<212> TYPE: DNA
<213> ORGANISM: Artificial sequence
<220> FEATURE:
<223> OTHER INFORMATION: Synthetic DNA

<400> SEQUENCE: 32
ggcagtggag ttagtgattg                                                 20

<210> SEQ ID NO 33
<211> LENGTH: 20
<212> TYPE: DNA
<213> ORGANISM: Artificial sequence
<220> FEATURE:
<223> OTHER INFORMATION: Synthetic DNA

<400> SEQUENCE: 33
atggcagtgg agttagtgat                                                 20

<210> SEQ ID NO 34
<211> LENGTH: 23
<212> TYPE: DNA
<213> ORGANISM: Artificial sequence
<220> FEATURE:
<223> OTHER INFORMATION: Synthetic DNA

<400> SEQUENCE: 34
gcaatcagct aactacactg cct                                             23

<210> SEQ ID NO 35
<211> LENGTH: 22
<212> TYPE: DNA
<213> ORGANISM: Artificial sequence
<220> FEATURE:
<223> OTHER INFORMATION: Synthetic DNA

<400> SEQUENCE: 35
```
caatcagcta actacactgc ct                    22

<210> SEQ ID NO 36
<211> LENGTH: 22
<212> TYPE: DNA
<213> ORGANISM: Artificial sequence
<220> FEATURE:
<223> OTHER INFORMATION: Synthetic DNA

<400> SEQUENCE: 36
gcaatcagct aactacactg cc                    22

<210> SEQ ID NO 37
<211> LENGTH: 21
<212> TYPE: DNA
<213> ORGANISM: Artificial sequence
<220> FEATURE:
<223> OTHER INFORMATION: Synthetic DNA

<400> SEQUENCE: 37
aatcagctaa ctacactgcc t                     21

<210> SEQ ID NO 38
<211> LENGTH: 21
<212> TYPE: DNA
<213> ORGANISM: Artificial sequence
<220> FEATURE:
<223> OTHER INFORMATION: Synthetic DNA

<400> SEQUENCE: 38
gcaatcagct aactacactg c                     21

<210> SEQ ID NO 39
<211> LENGTH: 34
<212> TYPE: PRT
<213> ORGANISM: Artificial sequence
<220> FEATURE:
<223> OTHER INFORMATION: Synthetic peptide

<400> SEQUENCE: 39

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 40
<211> LENGTH: 16
<212> TYPE: PRT
<213> ORGANISM: Artificial sequence
<220> FEATURE:
<223> OTHER INFORMATION: Synthetic peptide

<400> SEQUENCE: 40

Arg Arg Trp Arg Arg Trp Trp Arg Arg Trp Arg Arg Trp Arg Arg
1               5                   10                  15

<210> SEQ ID NO 41
<211> LENGTH: 7
<212> TYPE: PRT
<213> ORGANISM: Artificial sequence
<220> FEATURE:
<223> OTHER INFORMATION: Synthetic peptide

<400> SEQUENCE: 41

Arg Arg Arg Arg Arg Arg Arg
1               5

<210> SEQ ID NO 42
<211> LENGTH: 10
<212> TYPE: PRT
<213> ORGANISM: Artificial sequence
<220> FEATURE:
<223> OTHER INFORMATION: Synthetic peptide

<400> SEQUENCE: 42

Arg Pro Lys Lys Arg Lys Val Arg Arg Arg
1               5                   10

<210> SEQ ID NO 43
<211> LENGTH: 28
<212> TYPE: PRT
<213> ORGANISM: Artificial sequence
<220> FEATURE:
<223> OTHER INFORMATION: Synthetic peptide

<400> SEQUENCE: 43

Gly Ala Leu Phe Leu Gly Phe Leu Gly Gly Ala Ala Gly Ser Thr Met
1               5                   10                  15

Gly Ala Trp Ser Gln Pro Lys Ser Lys Arg Lys Val
            20                  25

<210> SEQ ID NO 44
<211> LENGTH: 26
<212> TYPE: PRT
<213> ORGANISM: Artificial sequence
<220> FEATURE:
<223> OTHER INFORMATION: Synthetic peptide

<400> SEQUENCE: 44

Asp Pro Lys Gly Asp Pro Lys Gly Val Thr Val Thr Val Thr Val Thr
1               5                   10                  15

Val Thr Gly Lys Gly Asp Pro Lys Pro Asp
            20                  25

<210> SEQ ID NO 45
<211> LENGTH: 18
<212> TYPE: PRT
<213> ORGANISM: Artificial sequence
<220> FEATURE:
<223> OTHER INFORMATION: Synthetic peptide

<400> SEQUENCE: 45

Lys Leu Ala Leu Lys Leu Ala Leu Lys Ala Leu Lys Ala Ala Leu Lys
1               5                   10                  15

Leu Ala

<210> SEQ ID NO 46
<211> LENGTH: 18
<212> TYPE: PRT
<213> ORGANISM: Artificial sequence
<220> FEATURE:
<223> OTHER INFORMATION: Synthetic peptide

<400> SEQUENCE: 46

Leu Leu Ile Ile Leu Arg Arg Arg Ile Arg Lys Gln Ala His Ala His
1               5                   10                  15

Ser Lys

<210> SEQ ID NO 47
<211> LENGTH: 16
<212> TYPE: PRT
<213> ORGANISM: Artificial sequence
<220> FEATURE:
<223> OTHER INFORMATION: Synthetic peptide

<400> SEQUENCE: 47

Arg Val Ile Arg Val Trp Phe Gln Asn Lys Arg Cys Lys Asp Lys Lys
1               5                   10                  15

<210> SEQ ID NO 48
<211> LENGTH: 21
<212> TYPE: PRT
<213> ORGANISM: Artificial sequence
<220> FEATURE:
<223> OTHER INFORMATION: Synthetic peptide

<400> SEQUENCE: 48

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 49
<211> LENGTH: 28
<212> TYPE: PRT
<213> ORGANISM: Artificial sequence
<220> FEATURE:
<223> OTHER INFORMATION: Synthetic peptide

<400> SEQUENCE: 49

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 50
<211> LENGTH: 28
<212> TYPE: DNA
<213> ORGANISM: Artificial sequence
<220> FEATURE:
<223> OTHER INFORMATION: Synthetic primer

<400> SEQUENCE: 50
caccggagaa ggggagagat tttcaaag                                          28

<210> SEQ ID NO 51
<211> LENGTH: 24
<212> TYPE: DNA
<213> ORGANISM: Artificial sequence
<220> FEATURE:
<223> OTHER INFORMATION: Synthetic primer

<400> SEQUENCE: 51
tacatggatt ctcggcagcc tgat                                              24

<210> SEQ ID NO 52
<211> LENGTH: 28
<212> TYPE: DNA
<213> ORGANISM: Artificial sequence
<220> FEATURE:
<223> OTHER INFORMATION: Synthetic primer

<400> SEQUENCE: 52
caccaaccaa aggatgaagt gcaagcgg                                          28

<210> SEQ ID NO 53
<211> LENGTH: 24
<212> TYPE: DNA
<213> ORGANISM: Artificial sequence
<220> FEATURE:
<223> OTHER INFORMATION: Synthetic primer

<400> SEQUENCE: 53
tcaggaggca agataagtg ggca                                           24

<210> SEQ ID NO 54
<211> LENGTH: 40
<212> TYPE: DNA
<213> ORGANISM: Artificial sequence
<220> FEATURE:
<223> OTHER INFORMATION: Synthetic primer

<400> SEQUENCE: 54
actgtagctg tcttcgaaga gggcgtcaga tcttgttacg                         40

<210> SEQ ID NO 55
<211> LENGTH: 40
<212> TYPE: DNA
<213> ORGANISM: Artificial sequence
<220> FEATURE:
<223> OTHER INFORMATION: Synthetic primer

<400> SEQUENCE: 55
tctgacgccc tcttcgaaga cagctacagt gtacttacat                         40

<210> SEQ ID NO 56
<211> LENGTH: 51
<212> TYPE: DNA
<213> ORGANISM: Artificial sequence
<220> FEATURE:
<223> OTHER INFORMATION: Synthetic primer

<400> SEQUENCE: 56
atgtccattg tttatggcgc gccaatatat ttttcgagga aagggttctt g            51

<210> SEQ ID NO 57
<211> LENGTH: 51
<212> TYPE: DNA
<213> ORGANISM: Artificial sequence
<220> FEATURE:
<223> OTHER INFORMATION: Synthetic primer

<400> SEQUENCE: 57
ttcctcgaaa aatatattgg cgcgccataa acaatggaca tttgattgcc a            51

<210> SEQ ID NO 58
<211> LENGTH: 20
<212> TYPE: RNA
<213> ORGANISM: Mus musculus

<400> SEQUENCE: 58
uagcugucuu cagacaucca                                               20

<210> SEQ ID NO 59
<211> LENGTH: 24
<212> TYPE: DNA
<213> ORGANISM: Artificial sequence
<220> FEATURE:
<223> OTHER INFORMATION: Synthetic primer

<400> SEQUENCE: 59
agggtctgct actgagatgc tctg                                    24

<210> SEQ ID NO 60
<211> LENGTH: 24
<212> TYPE: DNA
<213> ORGANISM: Artificial sequence
<220> FEATURE:
<223> OTHER INFORMATION: Synthetic primer

<400> SEQUENCE: 60
caaccactgg ttttctgcc accg                                     24

<210> SEQ ID NO 61
<211> LENGTH: 23
<212> TYPE: DNA
<213> ORGANISM: Artificial sequence
<220> FEATURE:
<223> OTHER INFORMATION: Synthetic primer

<400> SEQUENCE: 61
tagagataga ctccgggcga tga                                     23

<210> SEQ ID NO 62
<211> LENGTH: 23
<212> TYPE: DNA
<213> ORGANISM: Artificial sequence
<220> FEATURE:
<223> OTHER INFORMATION: Synthetic primer

<400> SEQUENCE: 62
ttgccttaaa caagaccacg aaa                                     23

<210> SEQ ID NO 63
<211> LENGTH: 20
<212> TYPE: DNA
<213> ORGANISM: Artificial sequence
<220> FEATURE:
<223> OTHER INFORMATION: Synthetic primer

<400> SEQUENCE: 63
ctgcccctgt cgcacatgtg                                         20

<210> SEQ ID NO 64
<211> LENGTH: 20
<212> TYPE: DNA
<213> ORGANISM: Artificial sequence
<220> FEATURE:
<223> OTHER INFORMATION: Synthetic primer

<400> SEQUENCE: 64
cttttatttt atcgtcgacc                                         20

<210> SEQ ID NO 65
<211> LENGTH: 23
<212> TYPE: DNA
<213> ORGANISM: Artificial sequence
<220> FEATURE:
<223> OTHER INFORMATION: Synthetic primer

<400> SEQUENCE: 65
tctttccacc aggccccccgg ctc                                    23

<210> SEQ ID NO 66
<211> LENGTH: 23

```
<212> TYPE: DNA
<213> ORGANISM: Artificial sequence
<220> FEATURE:
<223> OTHER INFORMATION: Synthetic primer

<400> SEQUENCE: 66
tgcgggcgga catggggaga tcc                                          23

<210> SEQ ID NO 67
<211> LENGTH: 20
<212> TYPE: DNA
<213> ORGANISM: Artificial sequence
<220> FEATURE:
<223> OTHER INFORMATION: Synthetic primer

<400> SEQUENCE: 67
tctcccatgc attcaaactg                                              20

<210> SEQ ID NO 68
<211> LENGTH: 19
<212> TYPE: DNA
<213> ORGANISM: Artificial sequence
<220> FEATURE:
<223> OTHER INFORMATION: Synthetic primer

<400> SEQUENCE: 68
cttttattta tcgtcgacc                                               19

<210> SEQ ID NO 69
<211> LENGTH: 24
<212> TYPE: DNA
<213> ORGANISM: Artificial sequence
<220> FEATURE:
<223> OTHER INFORMATION: Synthetic primer

<400> SEQUENCE: 69
ctgagggaac ggcaggagca cgag                                         24

<210> SEQ ID NO 70
<211> LENGTH: 24
<212> TYPE: DNA
<213> ORGANISM: Artificial sequence
<220> FEATURE:
<223> OTHER INFORMATION: Synthetic primer

<400> SEQUENCE: 70
ctgtagggag ggcttcgggc actt                                         24

<210> SEQ ID NO 71
<211> LENGTH: 20
<212> TYPE: DNA
<213> ORGANISM: Artificial sequence
<220> FEATURE:
<223> OTHER INFORMATION: Synthetic primer

<400> SEQUENCE: 71
taactcgagg aggagctgga                                              20

<210> SEQ ID NO 72
<211> LENGTH: 20
<212> TYPE: DNA
<213> ORGANISM: Artificial sequence
<220> FEATURE:
<223> OTHER INFORMATION: Synthetic primer

<400> SEQUENCE: 72
```
gccaaggttg tgaggttagg                                                 20

<210> SEQ ID NO 73
<211> LENGTH: 24
<212> TYPE: DNA
<213> ORGANISM: Artificial sequence
<220> FEATURE:
<223> OTHER INFORMATION: Synthetic primer

<400> SEQUENCE: 73
cagaggagga acgagctgaa gcgc                                            24

<210> SEQ ID NO 74
<211> LENGTH: 28
<212> TYPE: DNA
<213> ORGANISM: Artificial sequence
<220> FEATURE:
<223> OTHER INFORMATION: Synthetic primer

<400> SEQUENCE: 74
ttatgcacca gagtttcgaa gctgttcg                                        28

<210> SEQ ID NO 75
<211> LENGTH: 20
<212> TYPE: DNA
<213> ORGANISM: Artificial sequence
<220> FEATURE:
<223> OTHER INFORMATION: Synthetic primer

<400> SEQUENCE: 75
gaattgtgtt tcgatgatgc                                                 20

<210> SEQ ID NO 76
<211> LENGTH: 23
<212> TYPE: DNA
<213> ORGANISM: Artificial sequence
<220> FEATURE:
<223> OTHER INFORMATION: Synthetic primer

<400> SEQUENCE: 76
tcgcttcctc ttcctccgac aca                                             23

<210> SEQ ID NO 77
<211> LENGTH: 20
<212> TYPE: DNA
<213> ORGANISM: Artificial sequence
<220> FEATURE:
<223> OTHER INFORMATION: Synthetic primer

<400> SEQUENCE: 77
ccttacacat gaagaggcac                                                 20

<210> SEQ ID NO 78
<211> LENGTH: 20
<212> TYPE: DNA
<213> ORGANISM: Artificial sequence
<220> FEATURE:
<223> OTHER INFORMATION: Synthetic primer

<400> SEQUENCE: 78 cttttattttt atcgtcgacc                                                20

<210> SEQ ID NO 79
<211> LENGTH: 20
<212> TYPE: DNA
<213> ORGANISM: Artificial sequence

```
<220> FEATURE:
<223> OTHER INFORMATION: Synthetic primer

<400> SEQUENCE: 79
ctgtgccctc ttgcaaaagg                                                      20

<210> SEQ ID NO 80
<211> LENGTH: 22
<212> TYPE: DNA
<213> ORGANISM: Artificial sequence
<220> FEATURE:
<223> OTHER INFORMATION: Synthetic primer

<400> SEQUENCE: 80
ggacattcag gtgagggtct tg                                                   22

<210> SEQ ID NO 81
<211> LENGTH: 19
<212> TYPE: DNA
<213> ORGANISM: Artificial sequence
<220> FEATURE:
<223> OTHER INFORMATION: Synthetic primer

<400> SEQUENCE: 81
ggcaggaagg ctccagatg                                                       19

<210> SEQ ID NO 82
<211> LENGTH: 23
<212> TYPE: DNA
<213> ORGANISM: Artificial sequence
<220> FEATURE:
<223> OTHER INFORMATION: Synthetic primer

<400> SEQUENCE: 82
cctcactgtt catatgccca ttc                                                  23

<210> SEQ ID NO 83
<211> LENGTH: 20
<212> TYPE: DNA
<213> ORGANISM: Artificial sequence
<220> FEATURE:
<223> OTHER INFORMATION: Synthetic primer

<400> SEQUENCE: 83
acggtggaac tttgacttcg                                                      20

<210> SEQ ID NO 84
<211> LENGTH: 20
<212> TYPE: DNA
<213> ORGANISM: Artificial sequence
<220> FEATURE:
<223> OTHER INFORMATION: Synthetic primer

<400> SEQUENCE: 84
cagggcagag gaagtactgg                                                      20

<210> SEQ ID NO 85
<211> LENGTH: 20
<212> TYPE: DNA
<213> ORGANISM: Artificial sequence
<220> FEATURE:
<223> OTHER INFORMATION: Synthetic primer

<400> SEQUENCE: 85
gatctggcac cacaccttct                                                      20
```

```
<210> SEQ ID NO 86
<211> LENGTH: 20
<212> TYPE: DNA
<213> ORGANISM: Artificial sequence
<220> FEATURE:
<223> OTHER INFORMATION: Synthetic primer

<400> SEQUENCE: 86
ggggtgttga aggtctcaaa                                               20
```

COMPOSITIONS AND METHODS FOR GENERATING INDUCED PLURIPOTENT STEM CELLS

CROSS-REFERENCE

This application claims the benefit of U.S. Provisional Patent Application No. 61/441,367, filed Feb. 20, 2011, which application is incorporated herein by reference in its entirety.

BACKGROUND

Somatic cells can be induced to generate pluripotent stem cells that functionally resemble embryonic stem cells (ES cells). This reprogramming process, rooted in the remarkable cellular plasticity retained during differentiation, can be triggered by exogenous expression of a set of ES-cell specific gene regulators. However, reprogramming occurs with low efficiency and slow kinetics using the current technologies, reflecting our lack of in-depth mechanistic understanding of this process. At present, among the best-characterized reprogramming factors are a defined set of transcriptional regulators, Oct4 and Sox2, Klf4 and c-Myc. Most of these factors constitute integral components of the core gene regulatory circuits that coordinately control pluripotency and self-renewal in pluripotent stem cells.

miRNAs are a large family of small non-coding RNAs that primarily repress gene expression by pairing with partially complementary mRNA targets. The small size of miRNAs, combined with their imperfect target recognition, gives them enormous capacity and versatility to regulate global gene expression. miR-34 miRNAs belong to an evolutionarily conserved family. In mammals, there are three homologous members, miR-34a, b and c, which are localized to two distinct genomic loci, mir-34a, and mir-34b/c.

There is a need in the art for methods of generating induced pluripotent stem cells.

Literature

Takahashi and Yamanaka (2006) Cell 126:663-676; Yamanaka et al. (2007) Nature 448:313-7; Wernig et al. (2007) Nature 448:318-24; Maherali (2007) Cell Stem Cell 1:55-70; Maherali and Hochedlinger (2008) Cell Stem Cell 3:595-605; Park et al. (2008) Cell 134:1-10; Dimos et al. (2008) Science 321:1218-1221; Blelloch et al. (2007) Cell Stem Cell 1:245-247; Stadtfeld et al. (2008) Science 322:945-949; Stadtfeld et al. (2008) 2:230-240; Okita et al. (2008) Science 322:949-953; Choi et al. (2011) Nature Cell Biol. 13:1353.

SUMMARY OF THE INVENTION

The present disclosure provides a method of generating an induced pluripotent stem cell; as well as nucleic acids and genetically modified host cells useful in generating iPSCs. The present disclosure provides iPSCs, and methods of use of same.

BRIEF DESCRIPTION OF THE DRAWINGS

FIG. 5 is a Table showing contributions of miR-34a$^{-/-}$ iPSCs to chimeric animals.

FIGS. 8A-C depict repression of N-Myc expression by miR-34a. An N-myc 3'-UTR sequence (5'-ccacacggacagucacugcca-3'; SEQ ID NO:88) is shown in FIG. 8A. miR-34a (5'-UGGCAGUGUCUUAGCUGGUUGU-3'; SEQ ID NO:1) is shown above the N-Myc 3' UTR.

FIG. 11 is a Table that provides primer sequences for real-time polymerase chain reaction (PCR).

FIG. 12A provides an amino acid sequence of an Oct4 polypeptide; FIG. 12B provides a nucleotide sequence encoding the amino acid sequence provided in FIG. 12A.

FIG. 13A provides an amino acid sequence of an Sox2 polypeptide; FIG. 13B provides a nucleotide sequence encoding the amino acid sequence provided in FIG. 13A.

FIG. 14A provides an amino acid sequence of an Klf4 polypeptide; FIG. 14B provides a nucleotide sequence encoding the amino acid sequence provided in FIG. 14A.

FIG. 15A provides an amino acid sequence of an cMyc polypeptide; FIG. 15B provides a nucleotide sequence encoding the amino acid sequence provided in FIG. 15A.

FIGS. 16A and 16B provide miR-43a nucleotide sequences.

FIGS. 17A and 17B provide miR-43b nucleotide sequences.

FIGS. 18A and 18B provide miR-43c nucleotide sequences.

DEFINITIONS

Figure 1:
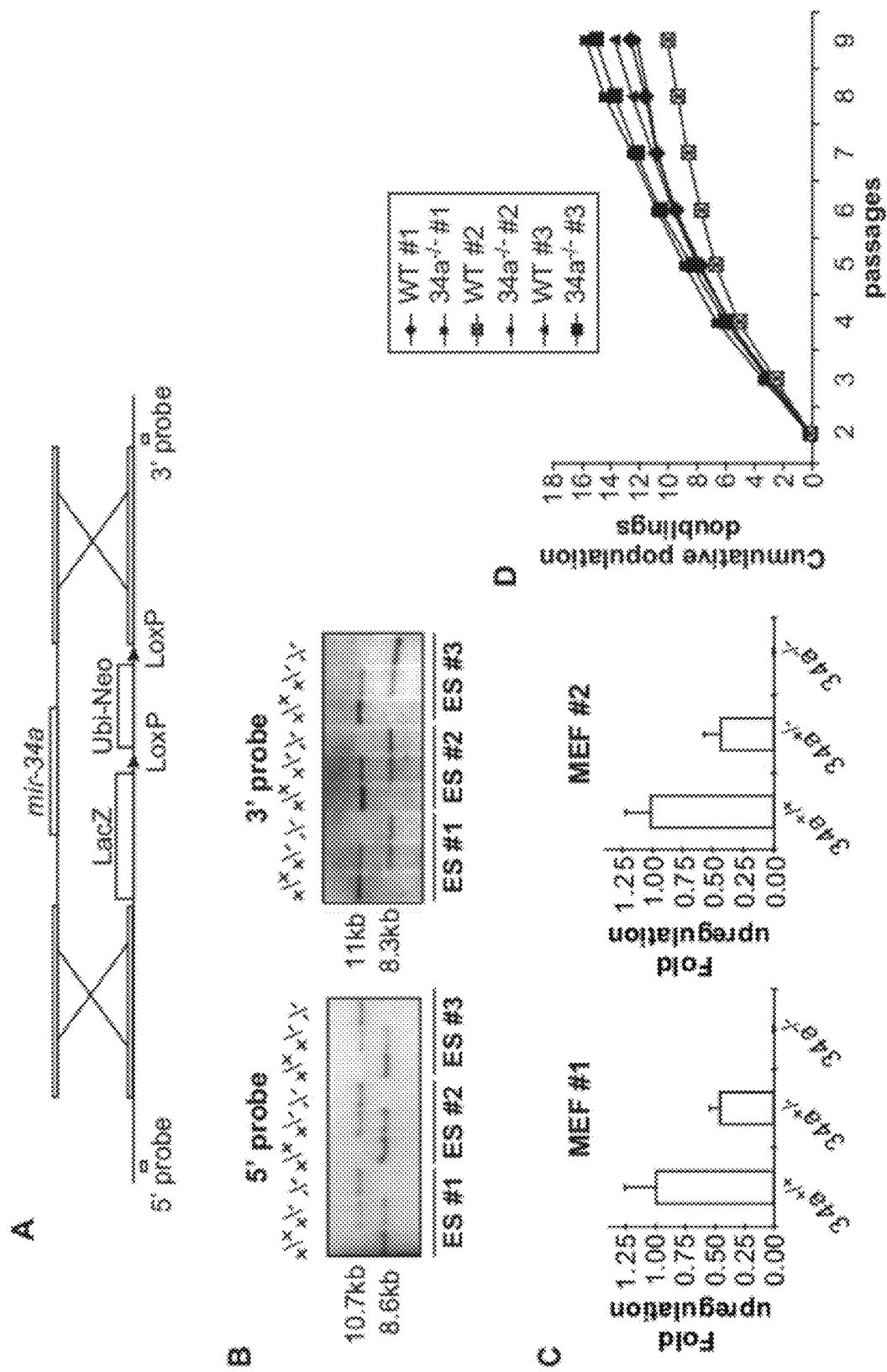
FIGS. 1A-D depict generation and characterization of miR-34a knockout mice.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

As used herein, the term "microRNA" refers to any type of interfering RNAs, including but not limited to, endogenous microRNAs and artificial microRNAs (e.g., synthetic miR- NAs). Endogenous microRNAs are small RNAs naturally encoded in the genome which are capable of modulating the productive utilization of mRNA. An artificial microRNA can be any type of RNA sequence, other than endogenous microRNA, which is capable of modulating the activity of an mRNA. A microRNA sequence can be an RNA molecule composed of any one or more of these sequences. MicroRNA (or "miRNA") sequences have been described in publications such as, Lim, et al., 2003, Genes & Development, 17, 991-1008, Lim et al., 2003, Science, 299, 1540, Lee and Ambrose, 2001, Science, 294, 862, Lau et al., 2001, Science 294, 858-861, Lagos-Quintana et al., 2002, Current Biology, 12, 735-739, Lagos-Quintana et al., 2001, Science, 294, 853-857, and Lagos-Quintana et al., 2003, RNA, 9, 175-179, which are incorporated herein by reference. Examples of microRNAs include any RNA that is a fragment of a larger RNA or is a miRNA, siRNA, stRNA, sncRNA, tncRNA, snoRNA, smRNA, snRNA, or other small non-coding RNA. See, e.g., US Patent Applications 20050272923, 20050266552, 20050142581, and 20050075492. A "microRNA precursor" (or "pre-miRNA") refers to a nucleic acid having a stem-loop structure with a microRNA sequence incorporated therein. A "mature microRNA" (or "mature miRNA") includes a microRNA that has been cleaved from a microRNA precursor (a "pre-miRNA"), or that has been synthesized (e.g., synthesized in a laboratory by cell-free synthesis), and has a length of from about 19 nucleotides to about 27 nucleotides, e.g., a mature microRNA can have a length of 19 nt, 20 nt, 21 nt, 22 nt, 23 nt, 24 nt, 25 nt, 26 nt, or 27 nt. A mature microRNA can bind to a target mRNA and inhibit translation of the target mRNA.

A "stem-loop structure" refers to a nucleic acid having a secondary structure that includes a region of nucleotides which are known or predicted to form a double strand (step portion) that is linked on one side by a region of predominantly single-stranded nucleotides (loop portion). The terms "hairpin" and "fold-back" structures are also used herein to refer to stem-loop structures. Such structures are well known in the art and these terms are used consistently with their known meanings in the art. The actual primary sequence of nucleotides within the stem-loop structure is not critical to the practice of the invention as long as the secondary structure is present. As is known in the art, the secondary structure does not require exact base-pairing. Thus, the stem may include one or more base mismatches. Alternatively, the base-pairing may be exact, i.e. not include any mismatches.

A "small interfering" or "short interfering RNA" or siRNA is a RNA duplex of nucleotides that is targeted to a gene of interest (a "target gene"). An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moeity. Preferred alkyl (e.g., alkyl, caboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. Other examples are well known to those of skill in the art.

A nucleobase may be comprised in a nucleoside or nucleotide, using any chemical or natural synthesis method described herein or known to one of ordinary skill in the art. Such nucleobase may be labeled or it may be part of a molecule that is labeled and contains the nucleobase.

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar.

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization. Hybridization conditions and post-hybridization washes are useful to obtain the desired determine stringency conditions of the hybridization. One set of illustrative post-hybridization washes is a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C. Stringent hybridization conditions and post-hybridization wash conditions are hybridization conditions and post-hybridization wash conditions that are at least as stringent as the above representative conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

"Complementary," as used herein, refers to the capacity for precise pairing between two nucleotides of a polynucleotide (e.g., an antisense polynucleotide) and its corresponding target polynucleotide. For example, if a nucleotide at a particular position of a polynucleotide is capable of hydrogen bonding with a nucleotide at a particular position of a target nucleic acid (e.g., a microRNA), then the position of hydrogen bonding between the polynucleotide and the target polynucleotide is considered to be a complementary position. The polynucleotide and the target polynucleotide are complementary to each other when a sufficient number of complementary positions in each molecule are occupied by nucleotides that can hydrogen bond with each other. Thus, "specifically hybridizable" and "complementary" are terms which are used to indicate a sufficient degree of precise pairing or complementarity over a sufficient number of nucleotides such that stable and specific binding occurs between the polynucleotide and a target polynucleotide.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A subject polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense polynucleotide which is 18 nucleotides in length having 4 (four) noncomplementary nucleotides which are flanked by two regions of complete complementarity with the target nucleic acid would have 77.8% overall complementarity with the target nucleic acid. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an antisense nucleic acid" includes a plurality of such nucleic acids and reference to "the induced pluripotent stem cell" includes reference to one or more induced pluripotent stem cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods of generating induced pluripotent stem cells (iPSCs). The present disclosure further provides genetically modified iPSCs, and therapeutic methods using such genetically modified iPSCs.

Methods of Generating Induced Pluripotent Stem Cells

The present disclosure provides methods of generating induced pluripotent stem cells (iPSCs). The methods generally involve forcing expression of a set of factors in a somatic cell in order to promote increased potency of the cell or de-differentiation of the cell; and reducing levels of miR-34 in the cell or antagonizing miR-34 activity in the cell. Forcing expression can include introducing expression vectors encoding polypeptides of interest into cells, introducing exogenous purified polypeptides of interest into cells, or contacting cells with a reagent that induces expression of an endogenous gene encoding a polypeptide of interest. Reducing levels of miR-34 (e.g., one, two, or three of miR-34a, miR-34b, miR-34c) in a somatic cell can involve introducing into the somatic cell a nucleic acid agent that reduces levels of miR-34. Antagonizing miR-34 activity in a somatic cell can involve introducing into the somatic cell a nucleic acid agent that reduces (e.g., blocks) binding of a miR-34 (e.g., one, two, or three of miR-34a, miR-34b, miR-34c) to a miR-34 target (where a miR-34 target is, e.g., a Nanog-encoding mRNA or a Sox2-encoding mRNA).

A subject method provides for increased efficiency of reprogramming a somatic cell, e.g., where the efficiency of generating pluripotent stem cells is at least 2-fold, at least 5-fold, at least 10-fold, at least 20-fold, or greater than 20-fold, higher than the reprogramming efficiency without introducing the nucleic acid that reduces the level or antagonizes the activity of miR-34.

Somatic Cells iPS cells are generated from mammalian cells (including mammalian somatic cells). Examples of suitable mammalian cells include, but are not limited to: fibroblasts, skin fibroblasts, dermal fibroblasts, bone marrow-derived mononuclear cells, skeletal muscle cells, adipose cells, peripheral blood mononuclear cells, macrophages, hepatocytes, keratinocytes, oral keratinocytes, hair follicle dermal cells, epithelial cells, gastric epithelial cells, lung epithelial cells, synovial cells, kidney cells, skin epithelial cells, pancreatic beta cells, and osteoblasts.

Mammalian cells used to generate iPS cells can originate from a variety of types of tissue including but not limited to: bone marrow, skin (e.g., dermis, epidermis), muscle, adipose tissue, peripheral blood, foreskin, skeletal muscle, and smooth muscle. The cells used to generate iPS cells can also be derived from neonatal tissue, including, but not limited to: umbilical cord tissues (e.g., the umbilical cord, cord blood, cord blood vessels), the amnion, the placenta, and various other neonatal tissues (e.g., bone marrow fluid, muscle, adipose tissue, peripheral blood, skin, skeletal muscle etc.).

Cells used to generate iPS cells can be derived from tissue of a non-embryonic subject, a neonatal infant, a child, or an adult. Cells used to generate iPS cells can be derived from neonatal or post-natal tissue collected from a subject within the period from birth, including cesarean birth, to death. For example, the tissue source of cells used to generate iPS cells can be from a subject who is greater than about 10 minutes old, greater than about 1 hour old, greater than about 1 day old, greater than about 1 month old, greater than about 2 months old, greater than about 6 months old, greater than about 1 year old, greater than about 2 years old, greater than about 5 years old, greater than about 10 years old, greater than about 15 years old, greater than about 18 years old, greater than about 25 years old, greater than about 35 years old, >45 years old, >55 years old, >65 years old, >80 years old, <80 years old, <70 years old, <60 years old, <50 years old, <40 years old, <30 years old, <20 years old or <10 years old.

iPS cells produce and express on their cell surface one or more of the following cell surface antigens: SSEA-3, SSEA-4, TRA-1-60, TRA-1-81, TRA-2-49/6E (alkaline phophatase), and Nanog. In some embodiments, iPS cells produce and express on their cell surface SSEA-3, SSEA-4, TRA-1-60, TRA-1-81, TRA-2-49/6E, and Nanog. iPS cells express one or more of the following genes: Oct-3/4, Sox2, Nanog, GDF3, REX1, FGF4, ESG1, DPPA2, DPPA4, and hTERT. In some embodiments, an iPS cell expresses Oct-3/4, Sox2, Nanog, GDF3, REX1, FGF4, ESG1, DPPA2, DPPA4, and hTERT. See, e.g., Takahashi and Yamanaka (2006) Cell 126:663-676; Yamanaka et al. (2007) Nature 448:313-7; Wernig et al. (2007) Nature 448:318-24; Maherali (2007) Cell Stem Cell 1:55-70; Maherali and Hochedlinger (2008) Cell Stem Cell 3:595-605; Park et al. (2008) Cell 134:1-10; Dimos et. al. (2008) Science 321:1218-1221; Blelloch et al. (2007) Cell Stem Cell 1:245-247; Stadtfeld et al. (2008) Science 322:945-949; Stadtfeld et al. (2008) 2:230-240; Okita et al. (2008) Science 322:949-953.

Reprogramming Factors

Examples of reprogramming factors include, but are not limited to:

(1) Oct3/4, Klf4, c-Myc;
(2) Oct3/4, Klf4, c-Myc, Sox2 (where Sox2 is replaceable with Sox1, Sox3, Sox15, Sox17 or Sox18; Klf4 is replaceable with Klf1, Klf2 or Klf5; c-Myc is replaceable with T58A (an active mutant), N-Myc or L-Myc);
(3) Oct3/4, Klf4, c-Myc, Sox2, Fbx15, Nanog, Eras, ECAT15-2, Tcll, β-catenin (active mutant S33Y);
(4) Oct3/4, Klf4, c-Myc, Sox2, TERT, SV40 Large T antigen (SV40LT);
(5) Oct3/4, Klf4, c-Myc, Sox2, TERT, HPV16 E6;
(6) Oct3/4, Klf4, c-Myc, Sox2, TERT, HPV16 E7;
(7) Oct3/4, Klf4, c-Myc, Sox2, TERT, HPV6 E6, HPV16 E7;
(8) Oct3/4, Klf4, c-Myc, Sox2, TERT, Bmil;
(9) Oct3/4, Klf4, Sox2 (see Nature Biotechnology, 26, 101-106 (2008));
(10) Oct3/4, Sox2, Nanog, Lin28 (see Science, 318, 1917-1920 (2007));
(11) Oct3/4, Sox2, Nanog, Lin28, hTERT, SV40LT (see Stem Cells, 26, 1998-2005 (2008));
(12) Oct3/4, Klf4, c-Myc, Sox2, Nanog, Lin28 (see Cell Research (2008) 600-603);
(13) Oct3/4, Klf4, c-Myc, Sox2, SV40LT (see also Stem Cells, 26, 1998-2005 (2008));
(14) Oct3/4, Klf4 (see Nature 454:646-650 (2008), Cell Stem Cell, 2:525-528 (2008));
(15) Oct3/4, c-Myc (see Nature 454:646-650 (2008));
(16) Oct3/4, Sox2 (see Nature, 451, 141-146 (2008), WO2008/118820);
(17) Oct3/4, Sox2, Nanog (see WO2008/118820);
(18) Oct3/4, Sox2, Lin28 (see WO2008/118820);
(19) Oct3/4, Sox2, c-Myc, Esrrb (where, Esrrb is replaceable with Esrrg; see Nat. Cell Biol., 11, 197-203 (2009));
(20) Oct3/4, Sox2, Esrrb (see Nat. Cell Biol., 11, 197-203 (2009));
(21) Oct3/4, Klf4, L-Myc;
(22) Oct3/4, Nanog;
(23) Oct3/4; and
(24) Oct3/4, Klf4, c-Myc, Sox2, Nanog, Lin28, SV40LT (see Science, 324: 797-801 (2009)).

In (1)-(24) above, in place of Oct3/4, other members of the Oct family, for example, Oct1A, Oct6 and the like, can also be used. In place of Sox2 (or Sox1, Sox3, Sox15, Sox17, Sox18), other members of the Sox family, for example, Sox7 and the like, can also be used. Furthermore, in place of Lin28, other members of the Lin family, for example, Lin28b and the like, can also be used.

See also, e.g., WO 2007/069666; Nature Biotechnology, 26, 101-106 (2008)); Cell, 126, 663-676 (2006); Cell, 131, 861-872 (2007); Nat. Cell Biol., 11, 197-203 (2009); and Nature, 451, 141-146 (2008), for combinations of reprogramming factors.

In some embodiments, iPS cells are generated from somatic cells by forcing expression of Oct-3/4 and Sox2 polypeptides; and by reducing the level of miR34 in the cell. In some embodiments, iPS cells are generated from somatic cells by forcing expression of Oct-3/4, Sox2, and Klf4 polypeptides; and by reducing the level of miR34 in the cell. In some embodiments, iPS cells are generated from somatic cells by forcing expression of Oct-3/4, Sox2, Klf4 and c-Myc polypeptides; and by reducing the level of miR34 in the cell. In some embodiments, iPS cells are generated from somatic cells by forcing expression of Oct-4, Sox2, Nanog, and LIN28 polypeptides; and by reducing the level of miR34 in the cell.

Oct-3/4 polypeptides, c-Myc polypeptides, and Klf4 polypeptides, are known in the art and are described in, e.g., U.S. Patent Publication No. 2009/0191159. Nanog polypeptides and Lin28 polypeptides are known in the art and are described in, e.g., U.S. Patent Publication No. 2009/0047263. See also the following GenBank Accession Nos.: 1) GenBank Accession Nos. NP_002692, NP_001108427; NP_001093427; NP_001009178; and NP_038661 for Oct-3/4; 2) GenBank Accession Nos. NP_004226, NP_001017280, NP_057354, AAP36222, NP_034767, and NP_446165 for Klf4 and Klf4 family members; 3) GenBank Accession Nos. NP_002458, NP_001005154, NP_036735, NP_034979, P0C0N9, and NP_001026123 for c-Myc; 4) GenBank Accession Nos. AAP49529 and BAC76999, for Nanog; and 5) GenBank Accession Nos. AAH28566 and NP_078950, for Lin28.

Sox2 (sex-determining region Y-box 2) polypeptides are known in the art, and any Sox2 polypeptide that retains Sox2 activity is suitable for use. A Sox2 polypeptide that retains Sox2 activity is also referred to as a "biologically active Sox2 polypeptide." A suitable Sox2 polypeptide that retains Sox2 activity is one that: (i) includes a DNA binding domain (DBD) that binds to the human nanog gene Sox element: 5'-TACAATG-3'; and (ii) is capable of transactivating a promoter comprising one or more nanog gene promoter Sox elements. See, e.g., Kuroda et al. (2005) *Mol. Cell. Biol.* 25(6):2475-2485. Sox2 amino acid sequences can be found in, e.g., GenBank Accession Nos: NP_003097, NP_001098933, NP_035573, ACA58281, BAA09168, NP_001032751, and NP_648694.

In some embodiments, a suitable Oct4 polypeptide retains Oct4 activity and comprises an amino acid sequence having at least 75%, at least 80%, at least 85%, at least 90%, at least 91%, at least 92%, at least 95%, 97%, or at least 99% amino acid sequence identity, or any other percent identity from at least 70% to 100%, to the Sox2 amino acid sequence depicted in FIG. 12A and as set forth in SEQ ID NO:7. In some embodiments, an Oct4 polypeptide comprises a protein transduction domain, as described below.

In some embodiments, a suitable nucleic acid encoding Oct4 comprises a nucleotide sequence having at least 75%, at least 80%, at least 85%, at least 90%, at least 91%, at least 92%, at least 95%, 97%, or at least 99% amino acid sequence identity, or any other percent identity from at least 70% to 100%, to the nucleotide sequence set forth in FIG. 12B and as set forth in SEQ ID NO:8.

In some embodiments, a suitable Sox2 polypeptide retains Sox2 activity and comprises an amino acid sequence having at least 75%, at least 80%, at least 85%, at least 90%, at least 91%, at least 92%, at least 95%, 97%, or at least 99% amino acid sequence identity, or any other percent identity from at least 70% to 100%, to the Sox2 amino acid sequence depicted in FIG. 13A, and as set forth in SEQ ID NO:9. In some embodiments, a Sox2 polypeptide comprises a protein transduction domain, as described below.

In some embodiments, a suitable nucleic acid encoding a Sox2 polypeptide comprises a nucleotide sequence having at least 75%, at least 80%, at least 85%, at least 90%, at least 91%, at least 92%, at least 95%, 97%, or at least 99% amino acid sequence identity, or any other percent identity from at least 70% to 100%, to the nucleotide sequence set forth in FIG. 13B and as set forth in SEQ ID NO:10.

In some embodiments, a suitable Klf4 polypeptide retains Klf4 activity and comprises an amino acid sequence having at least 75%, at least 80%, at least 85%, at least 90%, at least 91%, at least 92%, at least 95%, 97%, or at least 99% amino acid sequence identity, or any other percent identity from at least 70% to 100%, to the Klf4 amino acid sequence depicted in FIG. 14A and as set forth in SEQ ID NO:11. In some embodiments, a Klf4 polypeptide comprises a protein transduction domain, as described below.

In some embodiments, a suitable nucleic acid encoding Klf4 comprises a nucleotide sequence having at least 75%, at least 80%, at least 85%, at least 90%, at least 91%, at least 92%, at least 95%, 97%, or at least 99% amino acid sequence identity, or any other percent identity from at least 70% to 100%, to the nucleotide sequence set forth in FIG. 14B and as set forth in SEQ ID NO:12.

In some embodiments, a suitable c-Myc polypeptide retains c-Myc activity and comprises an amino acid sequence having at least 75%, at least 80%, at least 85%, at least 90%, at least 91%, at least 92%, at least 95%, 97%, or at least 99% amino acid sequence identity, or any other percent identity from at least 70% to 100%, to the c-Myc amino acid sequence depicted in FIG. 15A and as set forth in SEQ ID NO:13. In some embodiments, a c-Myc polypeptide comprises a protein transduction domain, as described below.

In some embodiments, a suitable nucleic acid encoding c-Myc comprises a nucleotide sequence having at least 75%, at least 80%, at least 85%, at least 90%, at least 91%, at least 92%, at least 95%, 97%, or at least 99% amino acid sequence identity, or any other percent identity from at least 70% to 100%, to the nucleotide sequence set forth in FIG. 15B and as set forth in SEQ ID NO:14.

In some embodiments, one or more nucleic acids comprising nucleotide sequences encoding one or more exogenous reprogramming factors is introduced into a somatic cell, where the one or more nucleic acids is a recombinant expression vector. Suitable expression vectors are described hereinbelow. In some embodiments, the expression vector is a viral expression vector; in other embodiments, the expression vector is a non-viral expression vector.

In some embodiments, introduction of an exogenous reprogramming factor polypeptide into a somatic cell is achieved by contacting the somatic cell with the exogenous reprogramming factor polypeptide, wherein the exogenous reprogramming factor polypeptide is taken up into the cell. Transfer of these proteins to somatic cells can be achieved using a method of protein transfer into cells known per se. Such methods include, for example, the method using a protein transfer reagent, the method using a protein transfer domain (PTD)-fusion protein, the microinjection method and the like. Protein transfer reagents are commercially available, including those based on a cationic lipid, such as BioPOTER Protein Delivery Reagent (Gene Therapy Systems), Pro-Ject™ Protein Transfection Reagent (PIERCE) and ProVectin (IMGENEX); those based on a lipid, such as Profect-1 (Targeting Systems); those based on a membrane-permeable peptide, such as Penetrain Peptide (Q biogene) and Chariot Kit (Active Motif), GenomONE (Ishihara Sangyo), which employs the HVJ envelop (inactivated Sendai virus), and the like. The transfer can be achieved per the protocols attached to these reagents, a common procedure being as described below. Nuclear reprogramming substance(s) is (are) diluted in an appropriate solvent (e.g., a buffer solution such as PBS or HEPES), a transfer reagent is added, the mixture is incubated at room temperature for about 5 to 15 minutes to form a complex, this complex is added to cells after exchanging the medium with a serum-free medium, and the cells are incubated at 37° C. for one to several hours. Thereafter, the medium is removed and replaced with a serum-containing medium In some embodiments, an exogenous reprogramming factor polypeptide comprises a protein transduction domain, e.g., an exogenous reprogramming factor polypeptide is linked, covalently or non-covalently, to a protein transduction domain.

"Protein Transduction Domain" or PTD refers to a polypeptide, polynucleotide, carbohydrate, or organic or inorganic compound that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of a Sox2 polypeptide. In some embodiments, a PTD is covalently linked to the carboxyl terminus of a Sox2 polypeptide.

Exemplary protein transduction domains include but are not limited to a minimal undecapeptide protein transduction domain (corresponding to residues 47-57 of HIV-1 TAT comprising YGRKKRRQRRR; SEQ ID NO:15); a polyarginine sequence comprising a number of arginines sufficient to direct entry into a cell (e.g., 3, 4, 5, 6, 7, 8, 9, 10, or 10-50 arginines); a VP22 domain (Zender et al., Cancer Gene Ther. 2002 June; 9(6):489-96); an Drosophila Antennapedia protein transduction domain (Noguchi et al., Diabetes 2003; 52(7):1732-1737); a truncated human calcitonin peptide (Trehin et al. Pharm. Research, 21:1248-1256, 2004); polylysine (Wender et al., PNAS, Vol. 97:13003-13008); RRQRRTSKLMKR (SEQ ID NO:16); Transportan GWTLNSAGYLLGKINLKALAALAKKIL (SEQ ID NO:17); KALAWEAKLAKALAKALAKHLAKALAKALKCEA (SEQ ID NO:18); and RQIKIWFQNRRMKWKK (SEQ ID NO:19). Exemplary PTDs include but are not limited to, YGRKKRRQRRR (SEQ ID NO:15), RKKRRQRRR (SEQ ID NO:20); an arginine homopolymer of from 3 arginine residues to 50 arginine residues; Exemplary PTD domain amino acid sequences include, but are not limited to, any of the following:

YGRKKRRQRRR;  (SEQ ID NO: 15)

RKKRRQRR;  (SEQ ID NO: 20)

YARAAARQARA;  (SEQ ID NO: 21)

THRLPRRRRRR;  (SEQ ID NO: 22)
and

GGRRARRRRRR.  (SEQ ID NO: 23)

In some embodiments, an exogenous reprogramming factor polypeptide comprises an arginine homopolymer of from 3 arginine residues to 50 arginine residues, e.g., from 3 to 6 arginine residues, from 6 to 10 arginine residues, from 10 to 20 arginine residues, from 20 to 30 arginine residues, from 30 to 40 arginine residues, or from 40 to 50 arginine residues. In some embodiments, an exogenous reprogramming factor polypeptide comprises six Arg residues covalently linked (e.g., by a peptide bond) at the amino terminus of the reprogramming factor polypeptide. In some embodiments, an exogenous reprogramming factor polypeptide comprises six Arg residues covalently linked (e.g., by a peptide bond) at the carboxyl terminus of the reprogramming factor polypeptide.

The exogenous reprogramming factor polypeptide introduced into a host somatic cell can be purified, e.g., at least about 75% pure, at least about 80% pure, at least about 85% pure, at least about 90% pure, at least about 95% pure, at least about 98% pure, at least about 99% pure, or more than 99% pure, e.g., free of proteins other than the reprogramming factor polypeptide and free of macromolecules other than the reprogramming factor polypeptide.

Nucleic Acid Agents that Reduce miR-34 Levels and/or that Antagonize miR-34 Activity As discussed above, a subject method of generating iPSCs generally involves forcing expression of a set of reprogramming factors in a somatic cell in order to promote increased potency of the cell or de-differentiation of the cell; and reducing levels of miR-34 (e.g., one, two, or three of miR-34a, miR-34b, miR-34c) in the cell, or reducing miR-34 (e.g., one, two, or three of miR-34a, miR-34b, miR-34c) activity levels in the cell (e.g., reducing binding of miR-34 to a miR-34 target). For example, in some embodiments, a subject method of generating a pluripotent stem cell from a somatic cell involves introducing into the somatic cell: a) one or more exogenous reprogramming factor polypeptides or one or more nucleic acids comprising nucleotide sequences encoding one or more reprogramming factor polypeptides; and b) a nucleic acid agent that reduces the level or activity of miR-34 in the cell, where said introducing results in reprogramming of the somatic cell into a pluripotent stem cell.

The present disclosure provides antisense nucleic acids, nucleic acids encoding the antisense nucleic acids, and composition comprising the antisense nucleic acids, where the nucleic acids reduce the level of miR-34 in a somatic cell and increase the efficiency of reprogramming of a somatic cell into a pluripotent stem cell. A subject antisense nucleic acid is in some embodiments a DNA. A subject antisense nucleic acid is in some embodiments an RNA. A subject antisense nucleic acid is in some embodiments a peptide nucleic acid (PNA), a morpholino nucleic acid (MO), a locked nucleic acid (LNA), or some other form of nucleic acid, as described in more detail below.

A nucleic acid agent that reduces the level of miR-34 in a somatic cell reduces the level by at least about 10%, at least about 15%, at least about 20%, at least about 25%, at least about 30%, at least about 40%, at least about 50%, at least about 60%, at least about 70%, at least about 80%, or more than 80%, compared to the level of miR-34 in the somatic cell in the absence of the nucleic acid agent. In some cases, the nucleic acid reduces the level of miR-34 in an iPSC generated from the somatic cell.

Reduction of miR-34 levels can be transient or permanent. For example, in some embodiments, a nucleic acid agent remains extrachromosomal, and induces a transient reduction of miR-34 levels in the cell. In other embodiments, a nucleic acid agent integrates into the genome of the cell.

A nucleic acid agent that reduces binding of a miR-34 in a somatic cell to a miR-34 target nucleic acid reduces the binding by at least about 10%, at least about 15%, at least about 20%, at least about 25%, at least about 30%, at least about 40%, at least about 50%, at least about 60%, at least about 70%, at least about 80%, or more than 80%, compared to the binding of the miR-34 in the somatic cell to the miR-34 target in the absence of the nucleic acid agent. In some cases, the nucleic acid reduces binding of miR-34 to a miR-34 target in an iPSC generated from the somatic cell.

Suitable nucleic acid agents include an antisense oligonucleotide, a locked nucleic acid, etc., that selectively reduces miR-34 levels or antagonizes miR-34 function; and a nucleic acid (e.g., a recombinant expression vector) that encodes an antisense nucleic acid that selectively reduces miR-34 levels. "Selective" reduction of miR-34 levels means that a nucleic acid agent does not substantially reduce the level of a microRNA other than a miR-34.

A miR-34 precursor nucleic acid comprises a nucleotide sequence having at least about 75%, at least about 80%, at least about 85%, at least about 90%, at least about 95%, at least about 98%, at least about 99%, or 100%, nucleotide sequence identity to the nucleotide sequence depicted in FIG. 16A (SEQ ID NO:2), FIG. 16B (SEQ ID NO:1), FIG. 17A (SEQ ID NO:4), FIG. 17B (SEQ ID NO:3), FIG. 18A (SEQ ID NO:6), or FIG. 18B (SEQ ID NO:5).

A suitable antisense nucleic acid comprises a nucleotide sequence that is complementary to, and can form a duplex with, nucleotides 15 through 40, nucleotides 40 through 75, nucleotides 50 through 75, nucleotides 60 through 80, nucleotides 65 through 75, or nucleotides 75 through 110, or other similar portion, of the nucleotide sequence depicted in one of FIGS. 16A, 17A, and 18A. A suitable antisense nucleic acid comprises a nucleotide sequence having fewer than five mismatches in complementarity with nucleotides 15 through 40, nucleotides 40 through 75, nucleotides 50 through 75, nucleotides 60 through 80, nucleotides 65 through 75, or nucleotides 75 through 110, or other similar portion, of the nucleotide sequence depicted in one of FIGS. 16A, 17A, and 18B.

The portion of a subject antisense nucleic acid that forms a duplex with a miR-34a precursor nucleic acid (e.g., the portion of a subject antisense nucleic acid that forms a duplex with nucleotides 15 through 40, nucleotides 40 through 75, nucleotides 50 through 75, nucleotides 60 through 80, nucleotides 65 through 75, or nucleotides 75 through 110, or other similar portion, of the nucleotide sequence depicted in one of FIG. 16A, FIG. 17A, and FIG. 18A) has a length of from about 12 nucleotides to about 50 nucleotides. For example, a subject antisense nucleic acid can have a length of from about 12 nt to about 50 nt. One having ordinary skill in the art will appreciate that this embodies antisense nucleic acids having a length of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

The total length of a subject antisense nucleic acid can be greater than the duplex-forming portion, e.g., the total length of a subject antisense nucleic acid can be from about 12 nucleotides (nt) to about 20 nt, from about 20 nt to about 30 nt, from about 30 nt to about 40 nt, from about 40 nt to about 50 nt, from about 50 nt to about 75 nt, from about 75 nt to about 100 nt, from about 100 nt to about 125 nt, from about 125 nt to about 150 nt, from about 150 nt to about 175 nt, or from about 175 nt to about 200 nt, or greater than 200 nt, in length.

A suitable antisense nucleic acid comprises a nucleotide sequence that is complementary to, and can form a duplex with, nucleotides 1-22, 2-22, 3-22, 1-20, 2-20, 3-20, or other similar portion, of the nucleotide sequence depicted in FIG. 16B. In some embodiments, a suitable antisense nucleic acid comprises a nucleotide sequence having fewer than five mismatches in complementarity with nucleotides 1-22, 2-22, 3-22, 1-21, 1-20, or 1-19, or other similar portion, of the nucleotide sequence depicted in FIG. 16B.

A suitable antisense nucleic acid comprises a nucleotide sequence that is complementary to, and can form a duplex with, nucleotides 1-22, 2-22, 3-22, 1-20, 2-20, 3-20, or other similar portion, of the nucleotide sequence depicted in FIG. 16B. In some embodiments, a suitable antisense nucleic acid comprises a nucleotide sequence having fewer than five mismatches in complementarity with nucleotides 1-22, 2-22, 3-22, 1-21, 1-20, or 1-19, or other similar portion, of the nucleotide sequence depicted in FIG. 17B.

A suitable antisense nucleic acid comprises a nucleotide sequence that is complementary to, and can form a duplex with, nucleotides 1-23, 2-23, 3-23, 1-22, 1-21, or 1-20, or other similar portion, of the nucleotide sequence depicted in FIG. 16B. In some embodiments, a suitable antisense nucleic acid comprises a nucleotide sequence having fewer than five mismatches in complementarity with nucleotides 1-22, 2-22, 3-22, 1-20, 2-20, 3-20, or other similar portion, of the nucleotide sequence depicted in FIG. 18B.

A nucleotide sequence of the stem-loop (precursor) form of miR-34a is:

(SEQ ID NO: 2)
5'-
GGCCAGCUGUGAGUGUUUCUUUGGCAGUGUCUUAGCUGGUUGUUGUGAGC
AAUAGUAAGGAAGCAAUCAGCAAGUAUACUGCCCUAGAAGUGCUGCACGU
UGUGGGGCCC-3'

The nucleotide sequence of mature miR-34a is: 5'-UGCAGUGUCUUAGCUGGUUGU-3' (SEQ ID NO: 1).

Exemplary, non-limiting nucleotide sequences that can be included in a subject antisense nucleic acid include nucleotide sequences complementary to a mature miR-34a, e.g.:

(SEQ ID NO: 24)
1) 5'-ACAACCAGCTAAGACACTGCCA-3';

(SEQ ID NO: 25)
2) 5'-CAACCAGCTAAGACACTGCCA-3';

(SEQ ID NO: 26)
3) 5'- ACAACCAGCTAAGACACTGCC-3';

(SEQ ID NO: 27)
4) 5'-AACCAGCTAAGACACTGCCA-3';
and (SEQ ID NO: 28)
5) 5'- ACAACCAGCTAAGACACTGC-3'.

A nucleotide sequence of the stem-loop (precursor) form of miR-34b is:

(SEQ ID NO: 4)
5'-
GUGCUCGGUUUGUAGGCAGUGUCAUUAGCUGAUUGUACUGUGGUGGUUA
CAAUCACUAACUCCACUGCCAUCAAAACAAGGCAC-3'.

The nucleotide sequence of mature miR-34b is:

(SEQ ID NO: 3)
5'-CAAUCACUAACUCCACUGCCAU-3'.

Exemplary, non-limiting nucleotide sequences that can be included in a subject antisense nucleic acid include nucleotide sequences complementary to a mature miR-34b, e.g.:

(SEQ ID NO: 29)
1) 5'-ATGGCAGTGGAGTTAGTGATTG-3';

(SEQ ID NO: 30)
2) 5'-TGGCAGTGGAGTTAGTGATTG-3';

(SEQ ID NO: 31)
3) 5'-ATGGCAGTGGAGTTAGTGATT-3';

(SEQ ID NO: 32)
4) 5'-GGCAGTGGAGTTAGTGATTG-3';
and (SEQ ID NO: 33)
5) 5'-ATGGCAGTGGAGTTAGTGAT-3'.

A nucleotide sequence of the stem-loop (precursor) form of miR-34c is:

(SEQ ID NO: 6)
5'-
AGUCUAGUUACUAGGCAGUGUAGUUAGCUGAUUGCUAAUAGUACCAAUC
ACUAACCACACGGCCAGGUAAAAAGAUU-3'.

The nucleotide sequence of mature miR-34c is:

(SEQ ID NO: 5)
5'-AGGCAGUGUAGUUAGCUGAUUGC-3'.

Exemplary, non-limiting nucleotide sequences that can be included in a subject antisense nucleic acid include nucleotide sequences complementary to a mature miR-34c, e.g.:

(SEQ ID NO: 34)
1) 5'-GCAATCAGCTAACTACACTGCCT-3';

(SEQ ID NO: 35)
2) 5'-CAATCAGCTAACTACACTGCCT-3';

(SEQ ID NO: 36)
3) 5'-GCAATCAGCTAACTACACTGCC-3';

-continued 4) 5'-AATCAGCTAACTACACTGCCT-3'; (SEQ ID NO: 37)
and 5) 5'-GCAATCAGCTAACTACACTGC-3'; (SEQ ID NO: 38)

In some embodiments, a subject antisense nucleic acid is referred to as an antagomir. Krützfeldt et al. (2005) *Nature* 438:685. A subject antisense nucleic acid can include one or more 2'-O-methyl (2'-OMe) sugar modifications. A subject antisense can include one or more phosphate backbone modifications, e.g., phosphorothioate, phosphoroamidate, etc. A subject antisense nucleic acid can include a cholesterol moiety conjugated to the nucleic acid, e.g., at the 3' end of the nucleic acid. Cholesterol can be linked to a 2'-O-methyl-oligoribonucleotide (2'-OMe-RNA) via a disulfide bond by reacting the 3'-(pyridyldithio)-modified 2'-OMe-RNA with thiocholesterol in dichloromethane-methanol solution. See, e.g., Oberhauser and Wagner (1992) *Nucl. Acids Res.* 20:533. Cholesterol can be linked to the 3' end of a nucleic acid via a hydroxyprolinol linkage. See, e.g., Krützfeldt et al. (2005) *Nature* 438:685.

In some embodiments, a subject antisense nucleic acid has a length of from about 20 nt to about 25 nt, where one or more (in some cases all) of the nucleotides includes a 2'-OMe modification, where one or more (in some cases all) of the phosphate backbone linkages includes phosphorothioate linkages, and where the 3' end of the nucleic acid comprises a cholesterol moiety covalently linked (e.g., via a hydroxyprolinol linkage). A subject antisense nucleic acid can also be a PNA, a LNA, or some other form of nucleic acid.

Recombinant Vectors

The present disclosure provides a nucleic acid comprising a nucleotide sequence encoding a subject antisense nucleic acid; and a nucleic acid comprising a nucleotide sequence encoding a subject target protector nucleic acid. In some embodiments, a nucleic acid comprising a nucleotide sequence encoding a subject antisense nucleic acid, or a subject target protector nucleic acid, is a recombinant expression vector that provides for production of the encoded antisense nucleic acid, or the encoded target protector nucleic acid, in a somatic cell (e.g., a mammalian somatic cell, a human somatic cell, a rodent somatic cell, etc.).

Suitable expression vectors include, but are not limited to, viral vectors (e.g. viral vectors based on vaccinia virus; poliovirus; adenovirus (see, e.g., Li et al., Invest Opthalmol V is Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:8186, 1998, Flannery et al., PNAS 94:6916 6921, 1997; Bennett et al., Invest Opthalmol V is Sci 38:2857 2863, 1997; Jomary et al., Gene Ther 4:683 690, 1997, Rolling et al., Hum Gene Ther 10:641648, 1999; Ali et al., Hum Mol Genet. 5:591594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; a lentivirus; a human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Suitable eukaryotic vectors include, for example, bovine papilloma virus-based vectors, Epstein-Barr virus-based vectors, vaccinia virus-based vectors, SV40, 2-micron circle, pcDNA3.1, pcDNA3.1/GS, pYES2/GS, pMT, p IND, pIND (Sp1), pVgRXR (Invitrogen), and the like, or their derivatives. Such vectors are well known in the art (Botstein et al., Miami Wntr. SyTnp. 19:265-274, 1982; Broach, In: "The Molecular Biology of the Yeast Saccharomyces: Life Cycle and Inheritance", Cold Spring Harbor Laboratory, Cold Spring Harbor, N.Y., p. 445-470, 1981; Broach, Cell 28:203-204, 1982; Dilon et al., J. Clin. Hematol. Oncol. 10:39-48, 1980; Maniatis, In: Cell Biology: A Comprehensive Treatise, Vol. 3, Gene Sequence Expression, Academic Press, NY, pp. 563-608, 1980.

The recombinant vector can include one or more coding regions that encode a polypeptide (a "selectable marker") that allow for selection of the recombinant vector in a genetically modified host cell comprising the recombinant vector. Suitable selectable markers include those providing antibiotic resistance; e.g., blasticidin resistance, neomycin resistance. Several selectable marker genes that are useful include the hygromycin B resistance gene (encoding aminoglycoside phosphotranferase (APH)) that allows selection in mammalian cells by conferring resistance to hygromycin; the neomycin phosphotranferase gene (encoding neomycin phosphotransferase) that allows selection in mammalian cells by conferring resistance to G418; and the like.

In some embodiments, the recombinant vector integrates into the genome of the host cell (e.g., a somatic cell); in other embodiments, the recombinant vector is maintained extrachromosomally in the host cell comprising the recombinant vector. A host cell (e.g., a somatic cell) comprising a subject recombinant vector is a "genetically modified" host cell.

A nucleotide sequence encoding a subject antisense nucleic acid can be operably linked to one or more transcriptional control elements, e.g., a promoter. Non-limiting examples of suitable eukaryotic promoters (promoters functional in a eukaryotic cell) include cytomegalovirus (CMV) immediate early, herpes simplex virus (HSV) thymidine kinase, early and late SV40, long terminal repeats (LTRs) from retrovirus, and mouse metallothionein-I. In some embodiments, the promoter is a constitutive promoter. Non-limiting examples of constitutive promoters include: ubiquitin promoter, CMV promoter, JeT promoter (U.S. Pat. No. 6,555,674), SV40 promoter, Elongation Factor 1 alpha promoter (EF1-alpha), RSV, and Mo-MLV-LTR. In some embodiments, the promoter is an inducible promoter. Non-limiting examples of inducible/repressible promoters include: Tet-On, Tet-Off, Rapamycin-inducible promoter, and Mx1. Selection of the appropriate vector and promoter is well within the level of ordinary skill in the art.

Modifications

In some embodiments, a subject nucleic acid (e.g., an antisense oligonucleotide; a target protector nucleic acid) comprises one or more modifications, including phosphate backbone modifications, base modifications, sugar modifications, and other types of modifications. As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Backbones and Modified Internucleoside Linkages

Examples of suitable nucleic acids (e.g., a subject antisense nucleic acid; a subject synthetic target protector nucleic acid) containing modifications include nucleic acids containing modified backbones and/or non-natural internucleoside linkages. Nucleic acids (e.g., a subject antisense nucleic acid; a subject synthetic target protector nucleic acid) having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts (such as, for example, potassium or sodium), mixed salts and free acid forms are also included.

In some embodiments, a subject nucleic acid (e.g., a subject antisense nucleic acid; a subject synthetic target protector nucleic acid) comprises one or more phosphorothioate and/or heteroatom internucleoside linkages, in particular —CH$_2$—NH—O—CH$_2$—, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). MMI type internucleoside linkages are disclosed in the above referenced U.S. Pat. No. 5,489,677. Suitable amide internucleoside linkages are disclosed in U.S. Pat. No. 5,602,240.

In some embodiments, a subject nucleic acid (e.g., a subject antisense nucleic acid; a subject synthetic target protector nucleic acid) comprises one or more morpholino backbone structures as described in, e.g., U.S. Pat. No. 5,034,506. For example, in some embodiments, a subject nucleic acid (e.g., a subject antisense nucleic acid; a subject synthetic target protector nucleic acid) comprises a 6-membered morpholino ring in place of a ribose ring. In some of these embodiments, a phosphorodiamidate or other non-phosphodiester internucleoside linkage replaces a phosphodiester linkage. Morpholino nucleic acids ("morpholinos") include bases bound to morpholine rings instead of deoxyribose rings; in addition, the phosphate backbone can include a non-phosphate group, e.g., a phosphorodiamidate group instead of phosphates. Summerton (1999) *Biochim. Biophys. Acta* 1489:141; Heasman (2002) *Dev. Biol.* 243:209; Summerton and Weller (1997) *Antisense & Nucl. Acid Drug Dev.* 7:187; Hudziak et al. (1996) *Antisense & Nucl. Acid Drug Dev.* 6:267; Partridge et al. (1996) *Antisense & Nucl. Acid Drug Dev.* 6:169; Amantana et al. (2007) *Bioconj. Chem.* 18:1325; Morcos et al. (2008) *BioTechniques* 45:616.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Modifications that Facilitate Entry into a Mammalian Cell

In some embodiments, a subject nucleic acid comprises a moiety that facilitates entry into a mammalian cell. For example, in some embodiments, a subject nucleic acid comprises a cholesterol moiety covalently linked to the 3' end of the nucleic acid. As another example, in some embodiments, a subject nucleic acid comprises a covalently linked peptide that facilitates entry into a mammalian cell. For example, a suitable peptide is an arginine-rich peptide. Amantana et al. (2007) *Bioconj. Chem.* 18:1325. As another example, in some embodiments, a subject nucleic acid comprises an octaguanidinium dendrimer attached to the end of the nucleic acid. Morcos et al. (2008) *BioTechniques* 45:616.

Mimetics

A subject nucleic acid (e.g., a subject antisense nucleic acid; a subject synthetic target protector nucleic acid) can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in an DNA/RNA molecule is replaced with a cyclophenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—$CH_2$—), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 C), stability towards 3'-exonucleolytic degradation and good solubility properties. Potent and nontoxic antisense oligonucleotides containing LNAs have been described (Wahlestedt et al., Proc. Natl. Acad. Sci. U.S.A., 2000, 97, 5633-5638).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Modified Sugar Moieties

A subject nucleic acid (e.g., a subject antisense nucleic acid; a subject synthetic target protector nucleic acid) can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C.sub.1 to $C_{10}$ alkyl or $C_2$ to $C_{10}$ alkenyl and alkynyl. Particularly suitable are O(($CH_2$)$_n$O)$_m$$CH_3$, O($CH_2$)$_n$$OCH_3$, O($CH_2$)$_n$$NH_2$, O($CH_2$)$_n$$CH_3$, O($CH_2$)$_n$$ONH_2$, and O($CH_2$)$_n$ON(($CH_2$)$_n$ $CH_3$)$_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy(2'-O—$CH_2$ $CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further suitable modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$.

Other suitable sugar substituent groups include methoxy (—O—$CH_3$), aminopropoxy (—$OCH_2CH_2CH_2NH_2$), allyl (—$CH_2$—CH=$CH_2$), —O-allyl (—O—$CH_2$—CH=$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid (e.g., a subject antisense nucleic acid; a subject synthetic target protector nucleic acid) may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido (5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), carbazole cytidine (2H-pyrimido(4,5-b)indol-2-one), pyridoindole cytidine (H-pyrido(3',':4,5)pyrrolo[2,3-d]pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound (e.g., an antisense nucleic acid; a target protector nucleic acid). These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278) and are suitable base substitutions, e.g., when combined with 2'-O-methoxyethyl sugar modifications.

Conjugates

Another possible modification of a subject nucleic acid (e.g., a subject antisense nucleic acid; a subject synthetic target protector nucleic acid), involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject antisense nucleic acid or target protector nucleic acid.

Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In some embodiments, a subject nucleic acid is linked, covalently or non-covalently, to a cell penetrating peptide. Suitable cell penetrating peptides include those discussed in U.S. Patent Publication No. 2007/0129305. The cell penetrating peptides can be based on known peptides, including, but not limited to, penetratins; transportans; membrane signal peptides; viral proteins (e.g., Tat protein, VP22 protein, etc.); and translocating cationic peptides. Tat peptides comprising the sequence YGRKKRRQRRR (SEQ ID NO:34) are sufficient for protein translocating activity. Additionally, branched structures containing multiples copies of Tat sequence RKKRRQRRR (SEQ ID NO:35; Tung, C. H. et al., Bioorg. Med. Chem 10:3609-3614 (2002)) can translocate efficiently across a cell membrane. Variants of Tat peptides capable of acting as a cell penetrating agent are described in Schwarze, S. R. et al., Science 285:1569-1572 (1999). A composition containing the C-terminal amino acids 159-301 of HSV VP22 protein is capable of translocating different types of cargoes into cells. Translocating activity is observed with a minimal sequence of DAATATRGRSAASRPTERPRAPARSASRPRRPVE (SEQ ID NO:39). Active peptides with arginine rich sequences are present in the Grb2 binding protein, having the sequence RRWRRWWRRWWRRWRR (SEQ ID NO:40; Williams, E. J. et al., J. Biol. Chem. 272: 22349-22354 (1997)) and polyarginine heptapeptide RRRRRRR (SEQ ID NO:41; Chen, L. et al., Chem. Biol. 8:1123-1129 (2001); Futaki, S. et al., J. Biol. Chem. 276: 5836-5840 (2001); and Rothbard, J. B. et al., Nat. Med. 6(11):1253-7 (2000)). An exemplary cell penetrating peptide has the sequence RPKKRKVRRR (SEQ ID NO:42), which is found to penetrate the membranes of a variety of cell types. Also useful are branched cationic peptides capable of translocation across membranes, e.g., $(KKKK)_2GGC$, $(KWKK)_2GCC$, and $(RWRR)_2GGC$ (Plank, C. et al., Human Gene Ther. 10:319-332 (1999)). A cell penetrating peptide can comprise chimeric sequences of cell penetrating peptides that are capable of translocating across cell membrane. An exemplary molecule of this type is transportan GALFLGFLGGAAGSTMGAWSQPKSKRKV (SEQ ID NO:43), a chimeric peptide derived from the first twelve amino acids of galanin and a 14 amino acid sequence from mastoporan (Pooga, M et al., Nature Biotechnol. 16:857-861 (1998). Other types of cell penetrating peptides are the VT5 sequences DPKGDPKGVTVTVTVTVTGKGDPKPD (SEQ ID NO:44), which is an amphipathic, beta-sheet forming peptide (Oehlke, J., FEBS Lett. 415(2):196-9 (1997); unstructured peptides described in Oehlke J., Biochim Biophys Acta. 1330(1):50-60 (1997); alpha helical amphipathic peptide with the sequence KLALKLALKALKAALKLA (SEQ ID NO:45; Oehlke, J. et al., Biochim Biophys Acta. 1414(1-2):127-39 (1998); sequences based on murine cell adhesion molecule vascular endothelial cadherin, amino acids 615-632 LLIILRRRIRKQAHAHSK (SEQ ID NO:46; Elmquist, A. et al., Exp Cell Res. 269(2):237-44 (2001); sequences based on third helix of the islet 1 gene enhancer protein RVIRVWFQNKRCKDKK (SEQ ID NO:47; Kilk, K. et al., Bioconjug. Chem. 12(6):911-6 (2001)); amphipathic peptide carrier Pep-1 KETWWETWWTEWSQPKKKRKV (SEQ ID NO:48; Morris, M. C. et al., Nat. Biotechnol. 19(12):1173-6 (2001)); and the amino terminal sequence of mouse prion protein MANLGYWLLALFVTMWTDVGLCKKRPKP (SEQ ID NO:49; Lundberg, P. et al., Biochem. Biophys. Res. Commun. 299(1):85-90 (2002).

Genetically Modified Cells

The present disclosure provides an isolated genetically modified somatic cell; and compositions comprising the genetically modified somatic cell. The present disclosure provides an isolated genetically modified iPSC; and compositions comprising the genetically modified.

Genetically Modified Somatic Cells

The present disclosure provides an isolated genetically modified somatic cell; and compositions comprising the genetically modified somatic cell. A subject genetically modified somatic cell comprises a homozygous disruption of a gene encoding miR-34a. Homozygous disruption of a genomic sequence encoding miR-34a can be achieved using, e.g., a cre-lox system, or any other system for disrupting a genomic sequence. Homozygous disruption of a genomic sequence encoding miR-34a results in a somatic cell that does not synthesize any miR-34a.

A subject genetically modified (miR-34a$^{-/-}$) somatic cell can be further genetically modified with one or more nucleic acids comprising nucleotide sequence encoding one or more exogenous reprogramming factors.

The present disclosure provides a composition comprising a subject genetically modified somatic cell. A subject composition comprises a subject genetically modified somatic cell; and will in some embodiments comprise one or more further components, which components are selected based in part on the intended use of the genetically modified somatic cell. Suitable components include, but are not limited to, salts; buffers; stabilizers; protease-inhibiting agents; cell membrane- and/or cell wall-preserving compounds, e.g., glycerol, dimethylsulfoxide, etc.; nutritional media appropriate to the cell; and the like.

Genetically Modified iPSCs

The present disclosure provides a genetically modified iPSC; and compositions comprising the genetically modified. A subject isolated iPSC: 1) has a homozygous disruption of a gene encoding miR-34a; and 2) is genetically modified with one or more nucleic acids comprising one or more exogenous reprogramming factors.

The present disclosure provides a composition comprising a subject genetically modified iPSC. A subject composition comprises a subject genetically modified iPSC; and will in some embodiments comprise one or more further components, which components are selected based in part on the intended use of the genetically modified iPSC. Suitable components include, but are not limited to, salts; buffers; stabilizers; protease-inhibiting agents; cell membrane- and/or cell wall-preserving compounds, e.g., glycerol, dimethylsulfoxide, etc.; nutritional media appropriate to the cell; and the like.

In some embodiments, a subject composition comprises a subject genetically modified iPSC and a matrix (a "subject genetically modified iPSC/matrix composition"), where a subject genetically modified iPSC is associated with the matrix. The term "matrix" refers to any suitable carrier material to which the genetically modified cells are able to attach themselves or adhere in order to form a cell composite. In some embodiments, the matrix or carrier material is present already in a three-dimensional form desired for later application. For example, bovine pericardial tissue is used as matrix which is crosslinked with collagen, decellularized and photofixed.

For example, a matrix (also referred to as a "biocompatible substrate") is a material that is suitable for implantation into a subject. A biocompatible substrate does not cause toxic or injurious effects once implanted in the subject. In one embodiment, the biocompatible substrate is a polymer with a surface that can be shaped into the desired structure that requires repairing or replacing. The polymer can also be shaped into a part of a structure that requires repairing or replacing. The biocompatible substrate can provide the supportive framework that allows cells to attach to it and grow on it.

Suitable matrix components include, e.g., collagen; gelatin; fibrin; fibrinogen; laminin; a glycosaminoglycan; elastin; hyaluronic acid; a proteoglycan; a glycan; poly(lactic acid); poly(vinyl alcohol); poly(vinyl pyrrolidone); poly(ethylene oxide); cellulose; a cellulose derivative; starch; a starch derivative; poly(caprolactone); poly(hydroxy butyric acid); mucin; and the like. In some embodiments, the matrix comprises one or more of collagen, gelatin, fibrin, fibrinogen, laminin, and elastin; and can further comprise a non-proteinaceous polymer, e.g., can further comprise one or more of poly(lactic acid), poly(vinyl alcohol), poly(vinyl pyrrolidone), poly(ethylene oxide), poly(caprolactone), poly(hydroxy butyric acid), cellulose, a cellulose derivative, starch, and a starch derivative. In some embodiments, the matrix comprises one or more of collagen, gelatin, fibrin, fibrinogen, laminin, and elastin; and can further comprise hyaluronic acid, a proteoglycan, a glycosaminoglycan, or a glycan. Where the matrix comprises collagen, the collagen can comprise type I collagen, type II collagen, type III collagen, type V collagen, type XI collagen, and combinations thereof.

The matrix can be a hydrogel. A suitable hydrogel is a polymer of two or more monomers, e.g., a homopolymer or a heteropolymer comprising multiple monomers. Suitable hydrogel monomers include the following: lactic acid, glycolic acid, acrylic acid, 1-hydroxyethyl methacrylate (HEMA), ethyl methacrylate (EMA), propylene glycol methacrylate (PEMA), acrylamide (AAM), N-vinylpyrrolidone, methyl methacrylate (MMA), glycidyl methacrylate (GDMA), glycol methacrylate (GMA), ethylene glycol, fumaric acid, and the like. Common cross linking agents include tetraethylene glycol dimethacrylate (TEGDMA) and N,N'-methylenebisacrylamide. The hydrogel can be homopolymeric, or can comprise co-polymers of two or more of the aforementioned polymers. Exemplary hydrogels include, but are not limited to, a copolymer of poly(ethylene oxide) (PEO) and poly(propylene oxide) (PPO); Pluronic™ F-127 (a difunctional block copolymer of PEO and PPO of the nominal formula $EO_{100}$-$PO_{65}$-$EO_{100}$, where EO is ethylene oxide and PO is propylene oxide); poloxamer 407 (a tri-block copolymer consisting of a central block of poly (propylene glycol) flanked by two hydrophilic blocks of poly (ethylene glycol)); a poly(ethylene oxide)-poly(propylene oxide)-poly(ethylene oxide) co-polymer with a nominal molecular weight of 12,500 Daltons and a PEO:PPO ratio of 2:1); a poly(N-isopropylacrylamide)-base hydrogel (a PNIPAAm-based hydrogel); a PNIPAAm-acrylic acid co-polymer (PNIPAAm-co-AAc); poly(2-hydroxyethyl methacrylate); poly(vinyl pyrrolidone); and the like.

A subject genetically modified iPSC/matrix composition can further comprise one or more additional components, where suitable additional components include, e.g., a growth factor; an antioxidant; a nutritional transporter (e.g., transferrin); a polyamine (e.g., glutathione, spermidine, etc.); and the like.

The cell density in a subject genetically modified iPSC/matrix composition can range from about $10^2$ cells/mm$^3$ to about $10^9$ cells/mm$^3$, e.g., from about $10^2$ cells/mm$^3$ to about $10^4$ cells/mm$^3$, from about $10^4$ cells/mm$^3$ to about $10^6$ cells/mm$^3$, from about $10^6$ cells/mm$^3$ to about $10^7$ cells/mm$^3$, from about $10^7$ cells/mm$^3$ to about $10^8$ cells/mm$^3$, or from about $10^8$ cells/mm$^3$ to about $10^9$ cells/mm$^3$.

The matrix can take any of a variety of forms, or can be relatively amorphous. For example, the matrix can be in the form of a sheet, a cylinder, a sphere, etc.

Methods of Use

The present disclosure provides a method for performing cell transplantation in a recipient individual in need thereof. The method generally involves transplanting an iPSC, generated from a somatic cell of a donor individual using a subject method, into a recipient individual.

In some embodiments, the donor individual and the recipient individual are the same individual. In other embodiments, the donor individual and the recipient individual are not the same, i.e., are not genetically identical.

Transplanting an iPSC into a recipient individual in need thereof can be carried out where the recipient individual is in need of replacement cells or tissues. Where a subject method involves introducing (implanting) an iPSC into an individual, allogeneic or autologous transplantation can be carried out.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example

Reduction of miR-34a miRNA Increases Efficiency of Somatic Cell Reprogramming

Materials and Methods
Animals

Using recombineering, we engineered a miR-34a knockout construct with a ~6 kb homologous arm on both the 5' and 3' end, which flanked a Kozak sequence, LacZ cDNA, and FRT-Neo-FRT cassette (Neo (aminoglycoside phosphotransferase) gene flanked by two frt sites for Flp-mediated excision). The knockout construct was electroporated into Bruce4 ES cells on the C57BL/6 genetic background. To screen for homologous recombination, ~300 Neo-resistant embryonic stem (ES) cell colonies were picked and cultured in 96 well plates. Correctly targeted ES cells were validated with Southern analysis using probes both 5' and 3' to the homologous arms. Three ES cell clones were injected into albino-057BL/6/cBrd/cBrd/cr blastocysts, and each gave rise to chimeric animals able to produce germ line transmission. Subsequently, we established three independent mouse lines for miR-34a knockout animals, all of which were phenotypically identical.

Oct4-Gfp mice were acquired from Jackson Laboratory (Jackson Laboratory, Cat #008214), and maintained on a mixed C57BL/6 and 129S4Sv/Jae genetic background. The ACT-FLP mice were purchased from the Jackson Laboratory (Jackson Laboratory, Cat #005703), and maintained on the C57BL/6 background. The miR-34a, p53 and p21 knockout mice were bred and maintained on the congenic C57BL/6 background to generate littermate-controlled MEFs with identical genetic background for iPSC reprogramming experiments. NCr-nu/nu female athymic mice were purchased from Taconic (Taconic, Cat No: NCRNU).

Cell Culture and Transfection

Primary mouse embryonic fibroblasts (MEFs) were isolated from littermate-controlled E13.5 wild-type and miR-34a$^{-/-}$ embryos, or wildtype and p53$^{-/-}$ embryos, respectively. MEFs and ecotropic Phoenix cells were cultured in DMEM (Invitrogen, Cat #11995-073) with 10% Fetal Bovine Serum (Hyclone, Cat #SH30396.03) and 1% 100× penicillin and streptomycin (Invitrogen, Cat No: 15140-163). For retroviral production, the ecotropic Phoenix cells were transfected with the pMX retroviral vectors that encode mouse Oct4, Sox2, c-Myc, and Klf4 (Addgene, Cat #13366, 13367, 13375, and 13370), respectively, by a calcium phosphate transfection method. Retrovirus-containing medium from the transfected phoenix cells was collected between 48-96 hours after transfection, and filtered through a 0.45 um filter (Millipore, Cat No: SLHV033RB) before transduction. iPSCs were cultured onto irradiated MEFs feeder layers in ES medium, which contained Knockout DMEM (Invitrogen, Cat No: 10829-018) supplemented with 15% ES-grade FBS (Invitrogen, Cat #16141079), 2 mM L-glutamine (Invitrogen, Cat No: 25030-164), 1×10$^{-4}$M MEM non-essential amino acids (Invitrogen, Cat No: 11140-076), 1×10$^{-4}$M 2-mercaptoethanol (Sigma, Cat No: M3148) and 1% 100× penicillin and streptomycin. Feeder-less ES cells, kindly provided by I. Lemischka, were cultured in the same ES medium on gelatin-treated plates, and annealed miR-34a, miR-34b and miR-34c oligos and control siRNA oligos were each transfected at a final concentration of 50 nM using Lipofectamine 2000 (Invitrogen, Cat #11668027) according to the manufacturer's protocol. Dicer$^{-/-}$ Hct116 cells (kindly provided by Dr. Bert Vogelstein) were cultured in DMEM with 10% FBS and 1% 100× penicillin and streptomycin[50]. The co-transfection of luciferase reporter and miRNA mimics were carried out using LT1 (Minis, Cat 190 MIR 2300) and TKO (Minis, Cat 190 MIR 2150) lipid-based transfection reagents.

iPSC Induction and Reprogramming Efficiency

Ecotropic phoenix cells were transfected with each pMX retroviral vectors that encode mouse Oct4, Sox2, c-Myc, and Klf4 using calcium phosphate transfection protocol. One day before infection, MEFs were seeded at 1.3×10$^5$ cell/well in a 6 well plate on 0.1% gelatin coated plate. MEFs were infected twice, and cultured for another 48 hours before we collected 1000 four-factor infected MEFs or 2500 three-factor infected MEFs into a well of a 12 well plate with irradiated MEF feeders and ES cell media. Once the colonies started to appear, alkaline phosphatase staining was performed to evaluate the reprogramming efficiency. Additionally, single iPSC-like colonies were each picked into one well of a 96 well plate, and then expanded on irradiated MEF feeders to establish stable iPSC lines. To determine reprogramming efficiency using Oct-Gfp transgenic MEFs, we collected 1000 four-factor infected MEFs and plated them into one well of a two-well chamber slide with irradiated MEF feeders and ES cell media. The reprogrammed iPSC colonies were scored by the expression of green fluorescent protein (GFP) marker.

Alkaline Phosphatase Staining and Immunofluorescence Staining

Alkaline phosphatase staining was performed using the Alkaline Phosphatase Detection Kit (Millipore, Cat #SCR004) according to the manufacturer's protocol. For immunocytochemical staining, iPSCs were fixed with 4% paraformaldehyde for 5 minutes at room temperature, followed by three phosphate buffered saline (PBS) washes. The fixed cells were then incubated at room temperature in blocking solution (0.1% Triton X-100 and 5% normal goat serum in PBS) for 30 minutes. Primary antibody against Oct-3/4 (1:100) (Santa Cruz Biotechnology, Cat No: sc-5279) or SSEA1 (1:200) (Santa Cruz Biotechnology, Cat No: sc-21702) was incubated overnight at 4° C., and secondary Cy3 goat anti-mouse IgG(H+L) antibody (Invitrogen, Cat No: A10521) was incubated at room temperature for 30 minutes. Immunofluorescence images were captured using a Zeiss 510 Meta uv/vis confocal microscope. To measure DNA damage response, wildtype, miR-34a$^{-/-}$ and p53$^{-/-}$ MEFs were infected with retrovirus containing the four reprogramming factors, and transduced cells were harvested day 6 post-infection. After being fixed with 4% parafomaldehyde, cells were stained with anti-phospho-Histone H2A.X (Ser139) ($\gamma$-H2AX) antibody (Millipore 05-636, clone JBW301, 1:200 dilution). At least 200 cells from different fields were counted to score for the number of $\gamma$-H2AX foci to determine the percentage of DNA damaged cells.

Teratoma Formation and Chimera Generation $1 \times 10^6$ of WT or miR-34a$^{-/-}$ iPSCs were injected into the dorsal flanks of 6-7 week old immune-deficient nu/nu mice (Taconic, Cat No: NCRNU, 6-7 weeks). After 4-5 wks, teratomas were fixed in 10% formalin, embedded in paraffin, sectioned in 6 μm, and stained with haematoxylin and eosin.

To determine the ability of miR-34a$^{-/-}$ iPSCs to contribute to adult chimeras, we generated Oct4-Gfp/+, miR-34a$^{-/-}$, A$^w$/a iPSCs on a mixed C57BL/6 and 129S4Sv/Jae genetic background. Three stable miR-34a$^{-/-}$ iPSC lines were established and injected into albino-057BL/6/cBrd/cBrd/cr blastocysts at passage seven. Chimeric blastocysts were subsequently transferred to day 2.5 pseudopregnant recipient CD-1 females, and the percentage of chimera contribution was determined by scoring level of coat color pigmentation on an otherwise albino mouse.

Real-Time PCR Analyses

TaqMan miRNA assays (Applied Biosystems) were used to measure the level of mature miR-34 miRNAs. The mRNA levels of total, exogenous, and endogenous Oct4, Sox2, Klf4 and c-Myc were determined by real-time polymerase chain reaction (PCR) with SYBR (Kapa Biosystems, Cat ##KK4604) using the primers listed in FIG. 11. The mRNA levels of Nanog, N-Myc, pri-miRNA-34a, pri-miRNA-34b/c, p21 were determined similarly. In all real-time PCR experiments, Actin was used as a normalization control.

Western Analyses 72 hours post-transfection, mock-transfected feederless ES cells, or ES cells transfected with 50 nM miR-34a, miR-34b, miR-34a and siGFP, were harvested into RIPA buffer (20 mM Tris pH7.5, 150 mM NaCl, 1% Nonidet P-40, 0.5% Sodium Deoxycholate, 1 mM EDTA, and 0.1% SDS with protease inhibitor cocktail (Roche, Cat #11836153001). After normalization of protein concentration using Bradford assays (BioRad, Cat #500-0111), cell lysates were subjected to Western analyses. For iPSC collection, trypsinized iPSCs and feeder MEFs were both plated on a gelatin-coated plate. After one hour of culture, feeder MEFs were largely attached to the plates, while most iPSCs remained in the supernatant or lightly attached to the MEF feeders. iPSCs were separated from the MEF feeders by thorough washing, and subsequently subjected to Western analyses. Antibodies against mouse Nanog (Abcam, ab80892), Sox2 (Millipore, ab5603), Oct3/4 (Santa Cruz, sc-5279), N-Myc (Abcam, ab18698), Klf4 (Abcam, ab26648), p21 (Santa Cruz, sc-6246), and p53 (Vector Laboratories, CM5), were used at 1:1000 dilution. α-Tubulin (Sigma, clone B-5-1-2) was used at a 1:4000 dilution as a loading control.

Luciferase Assays

The mouse Sox2 3'UTR containing one miR-34a binding site was amplified from cDNAs (forward primer, 5'-CACCG-GAGAAGGGGAGAGATTTTCAAAG-3' (SEQ ID NO:50); reverse primer, 5'-TACATGGATTCTCGGCAGCCTGAT-3' (SEQ ID NO:51)), and ligated to PENTR/TOPO-D vector (Invitrogen, Cat #K2400-20). Similarly, a fragment containing the mouse Nanog 3'UTR and a small portion of its open reading frame was cloned into the same PENTR/TOPO-D (forward primer, 5'-CACCAACCAAAGGATGAAGTG-CAAGCGG-3' (SEQ ID NO:52), reverse primer, 5'-TCAG-GAGGCAAAGATAAGTGGGCA-3' (SEQ ID NO:53)). Mutagenesis of these miR-34a binding sites was carried out by the following primers: Nanog forward 5'-ACTGTAGCT-GTCTTCGAAGAGGGCGTCAGATCTTGTTACG-3' (SEQ ID NO:54), Nanog reverse 5'-TCTGACGCCCTCT-TCGAAGACAGCTACAGTGTACTTACAT-3' (SEQ ID NO:55); Sox2 forward, 5'-ATGTCCATTGTTTATG-GCGCGCCAATATATTTTTCGAGGAAAGGGTTCTTG-3' (SEQ ID NO:56), Sox2 reverse: 5'-TTCCTC-GAAAAATATATTGGCGCGCCATAAACAATGGAC ATTTGATTGCCA-3' (SEQ ID NO:57). Wildtype and mutated Nanog and Sox2 constructs were each cloned downstream of a firefly luciferase reporter. The resulted firefly luciferase constructs (100 ng) were each transfected into Dicer-deficient HCT116 cells together with a Renilla luciferase construct (10 ng) as a normalization control, and either 50 nM control siRNA (siGFP) or miR-34a mimics, respectively. These miRNA mimics were generated by annealing two complementary RNA oligos[9]. The Firefly and Renilla luciferase activity of each transfection was determined by dual luciferase assay (Promega, Cat #E1960) 72 h post-transfection.

Results

To investigate the role of miR-34 miRNAs in iPSC induction, we generated miR-34a knockout mice as a source of miR-34a$^{-/-}$ somatic cells for reprogramming. The miR-34a knockout construct replaced the miR-34a pre-miRNA sequence with a LacZ cDNA containing the Kozak sequence, followed by a FRT-Neo-FRT cassette (FIG. 1A). Homologous recombination was carried out in C57BL/6 ES cells, and subsequent germ line transmission of the targeted allele was confirmed by Southern analyses in animals derived from each of the three correctly targeted ES cell lines (FIG. 1B). We generated multiple pairs of littermate-controlled wildtype, miR-34a$^{+/-}$ and miR-34a$^{-/-}$ MEFs, and verified that the genetic ablation of miR-34a abolished miR-34a induction by culture stress (FIG. 1C).

miR-34a$^{-/-}$ mice were born at the expected Mendelian ratio, without obvious developmental or pathological abnormalities up to 12 months of age. The miR-34a$^{-/-}$ mice in which the Neo cassette was deleted by crossing to an Actin-FLP deleter stain were phenotypically identical. MEFs isolated from miR-34a$^{-/-}$ embryos, when compared to their isogenic wildtype littermate controls, had a comparable, but slightly enhanced, proliferation rate up to passage 9 (FIG. 1D).

FIGS. 1A-D. Generation of miR-34a knockout mice. A. Diagram of endogenous miR-34a gene structure and the knockout construct. Using recombineering, we engineered the miR-34a targeting vector construct with a ~6 kb homologous arm on both 5' and 3' ends orange), flanking a Kozak sequence, LacZ cDNA (blue) and FRT-Neo-FRT cassette (blue). To facilitate homologous recombination, the knockout construct was electroporated into the Bruce4 C57B6 ES cells on the C57BL/6 background. B. Validating the germline transmission of the miR-34a targeted allele using Southern analysis. Putative wildtype, miR-34a$^{+/-}$ and miR-34a$^{-/-}$ animals derived from each ES line, as determined by PCR genotyping, were analyzed by Southern blot using probes (red) either 5' or 3' to the homologous arms. Animals derived from three correctly targeted ES cells were validated. C. Confirming loss of miR-34a expression in knockout MEFs. Wildtype, miR-34a$^{+/-}$ and miR-34a$^{-/-}$ MEFs were prepared from E13.5 embryos, and subsequently analyzed by real time PCR to quantify the expression of miR-34a. While wildtype MEFs showed robust miR-34a induction upon culture stress, no miR-34a expression was detected in miR-34a$^{-/-}$ MEFs. The miR-34a level in miR-34a+/− MEFs was half that of wildtype MEFs. miR-34a$^{-/-}$ MEFs derived from two different targeted ES cell lines yielded the same result. D. miR-34a$^{-/-}$ MEFs exhibit similar, yet slightly enhanced, cell proliferation compared to wildtype MEFs. Three pairs of littermate-controlled wildtype and miR-34a$^{-/-}$ MEFs were cultured for nine consecutive passages in vitro, and the cumulative population doubling was recorded for each passage.

Figure 2:
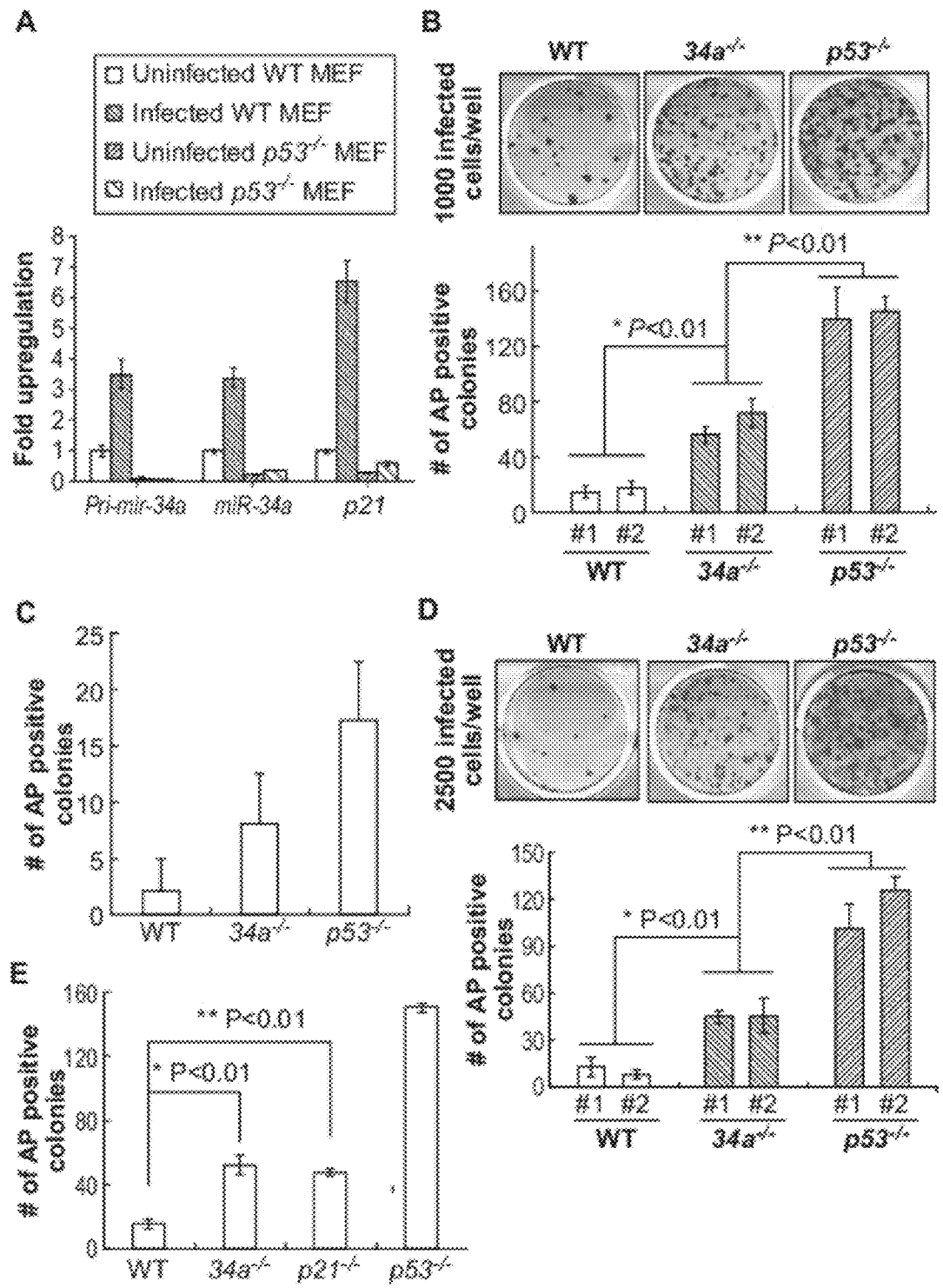
FIGS. 2A-E depict the effect of miR-34a deficiency on reprogramming efficiency.
Figure 3:
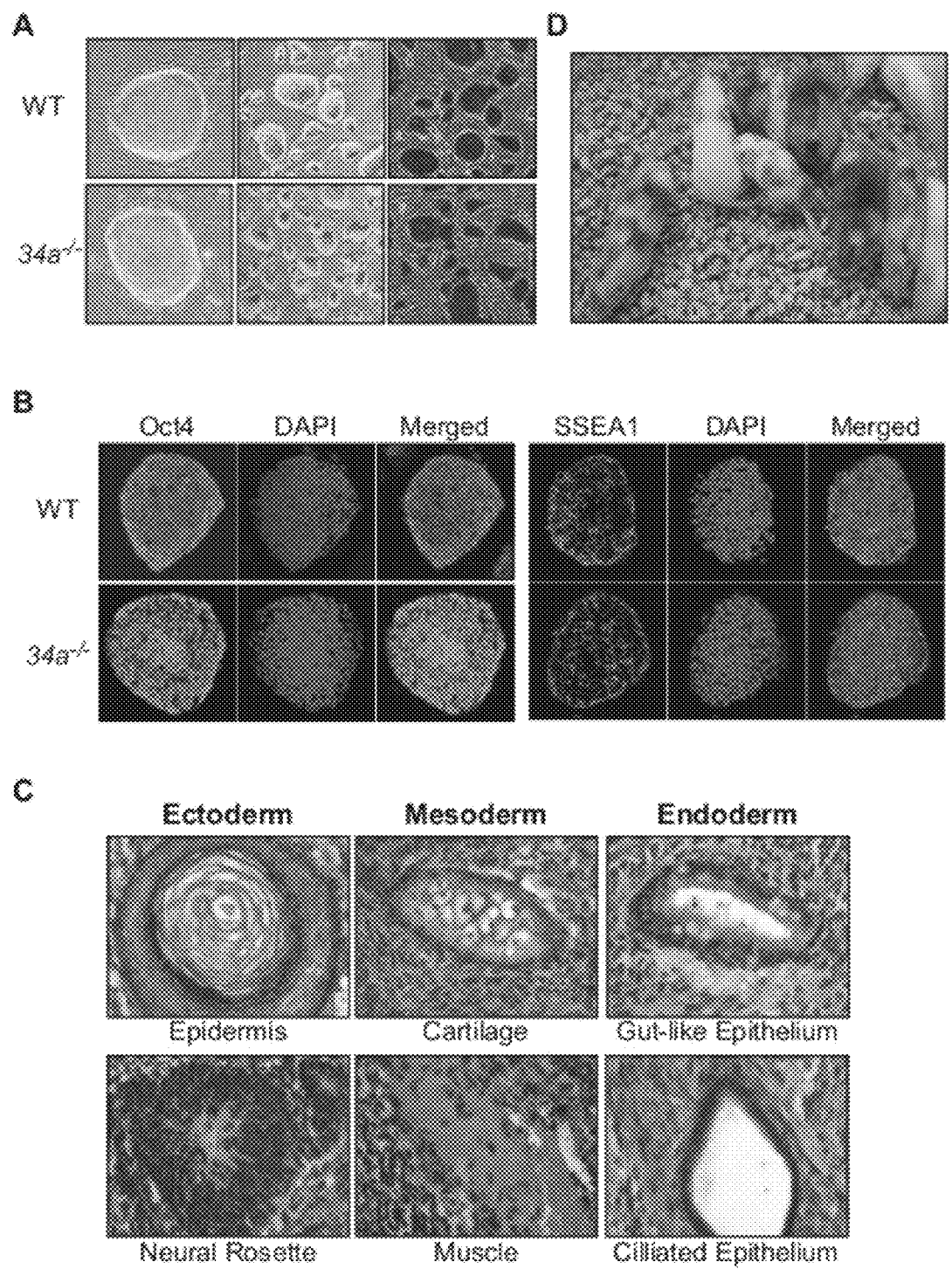
FIGS. 3A-D depict functional comparison of miR-34a$^{-/-}$ iPSCs and wildtype iPSCs.

Despite the similar cell proliferation rate between wildtype and miR-34a$^{-/-}$ MEFs, we observed a significant increase in the reprogramming efficiency of miR-34a$^{-/-}$ MEFs when the four-factors (Oct4, Sox2, Klf4 and c-Myc) were introduced by retroviral transduction (FIG. 2B). miR-34a$^{-/-}$ MEFs yielded nearly a four-fold increase in the number of alkaline phosphatase positive colonies with characteristic iPSC morphology when compared to wildtype MEFs (FIG. 2B). Furthermore, when we plated infected miR-34a$^{+/+}$ or miR-34a$^{-/-}$ MEFs into 96 well plates at a density of one cell per well, we observed a similar increase in alkaline phosphatase positive colonies derived from cells lacking miR-34a (FIG. 2C). We confirmed the increased reprogramming efficiency in miR-34a$^{-/-}$ MEFs by comparing wildtype and miR-34a$^{-/-}$ MEFs that carry an Oct4-Gfp transgene, scoring the reprogrammed iPSCs based on GFP fluorescence. The stable reprogrammed iPSCs derived from miR-34a$^{+/+}$ or miR-34a$^{-/-}$ MEFs expressed molecular markers characteristic of pluripotent stem cells, including Oct4 and SSEA1 (FIG. 3A, 3B). Notably, miR-34a-deficiency not only enhanced the overall efficiency of iPSC generation, but also led to more rapid reprogramming kinetics. While small visible colonies first started to appear 7 days post-infection in four-factor-transduced wildtype MEFs, we could identify such colonies as early as 5 days post-infection in miR-34a$^{-/-}$ MEFs.

Since c-Myc transcriptionally represses miR-34a expression[10], miR-34 deficiency may partially mimic the effect of exogenous c-Myc expression to promote reprogramming. Consistent with this hypothesis, when reprogramming was induced by three factors (Oct4, Sox2, and Klf4) without exogenous c-Myc, the efficiency of iPSC generation in miR-34a deficient MEFs was significantly enhanced, reaching ~4.5 fold of that of the wildtype MEFs (FIG. 2D). We also observed more rapid reprogramming kinetics in miR-34a$^{-/-}$ MEFs under this condition. Notably, the miR-34a$^{-/-}$ MEFs were less efficient than p53$^{-/-}$ MEFs in generating iPSC colonies when induced by either three factors or four-factors (FIG. 2B, 2C, 2D). This difference could be partially attributed to the functional redundancy from miR-34b and miR-34c. Perhaps more importantly, p53's suppression of reprogramming may be mediated by several distinct mechanisms, including pathways both dependent on miR-34 and independent of miR-34. Previous studies have identified the cell cycle regulator p21 as an important mediator of p53 to suppress reprogramming efficiency. Interestingly, miR-34a and p21 are similarly induced during reprogramming (FIG. 2A), and similarly regulated at the transcriptional level by both p53 and c-Myc[9, 10, 24, 25]. miR-34a$^{-/-}$ MEFs and p21$^{-/-}$ MEFs both exhibited comparable increases in reprogramming efficiency, but not to the extent of p53$^{-/-}$ MEFs (FIG. 2E). These findings suggest that, like p21, miR-34 miRNAs constitute important downstream effectors of p53 to suppress iPSC generation.

Figure 4:
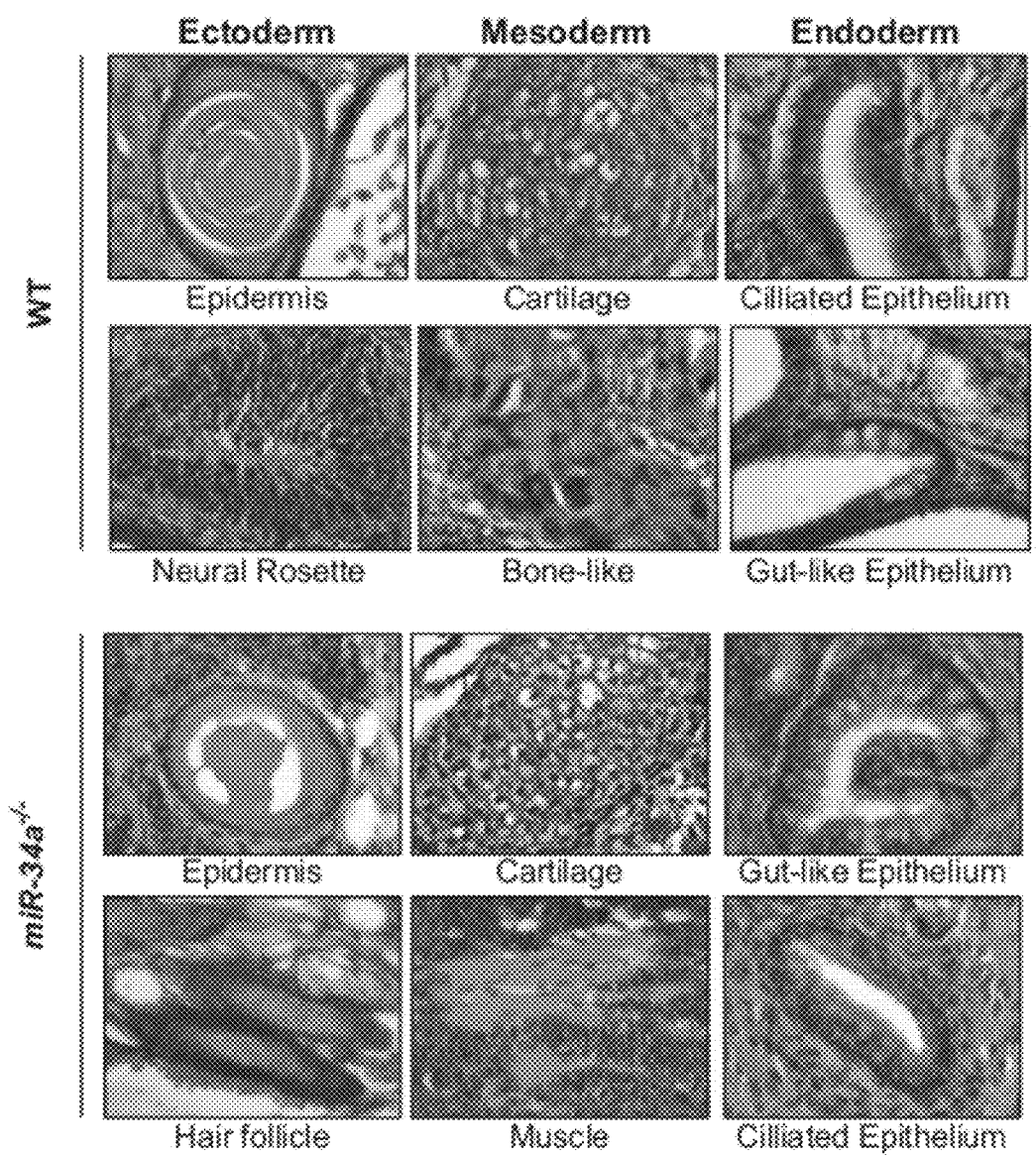
FIG. 4 depicts differentiated teratomas generated from four-factor induced wildtype and miR-34$^{a/a}$ iPSCs.

FIGS. 2A-E. Deficiency of miR-34a increases reprogramming efficiency. A. Transduction of four reprogramming factors triggered p53-dependent induction of miR-34 miRNAs. Three days after retroviral transduction, pri-mir-34a, mature miR-34a and p21 levels were assayed in uninfected and four-factor induced wildtype and p53$^{-/-}$ MEFs. Induction of mir-34a by four-factor transduction was comparable to that of p21, and was dependent on the functional p53. B. miR-34a deficiency significantly enhanced four-factor induced reprogramming in MEFs. 1000 infected wildtype, miR-34a$^{-/-}$ and p53$^{-/-}$ MEFs were collected by flow cytometry and plated in each well of a 12 well plate with feeder MEFs, and alkaline phosphatase-positive colonies were counted 2 weeks post-infection. A representative image and quantitative analysis is shown out of five independent experiments comparing littermate-controlled wildtype, miR-34a$^{-/-}$ and p53$^{-/-}$ MEFs for reprogramming efficiency. *P<0.01 for comparison between wildtype and miR-34a$^{-/-}$ (n=4). **P<0.01 for comparison between miR-34a$^{-/-}$ and p53$^{-/-}$ (n=4). C. Single-sorted, four-factor infected MEFs were cultured in 96-well plates. Four weeks after plating, alkaline phosphatase-positive colonies were scored for wildtype, miR-34a$^{-/-}$ and p53$^{-/-}$ iPSCs. * P<0.05 for comparison between wildtype and miR-34a$^{-/-}$ (n=3). A representative image and quantitative analysis is shown out of three independent experiments comparing littermate-controlled wildtype, miR-34a$^{-/-}$ and p53$^{-/-}$ MEFs for reprogramming efficiency. D. miR-34a deficiency significantly enhanced MEF reprogramming by the three factors without c-Myc. 2500 infected wildtype, miR-34a$^{-/-}$ and p53$^{-/-}$ MEFs were collected by flow cytometry and plated in 12 well plates; and alkaline phosphatase-positive colonies were counted 3 weeks post-plating. A representative image and quantitative analysis is shown. *P<0.01 for comparison between wildtype and miR-34a$^{-/-}$ (n=4). **P<0.01 for comparison between miR-34a$^{-/-}$ and p53$^{-/-}$ (n=4). E. Deficiency in either miR-34a or p21 enhances reprogramming efficiency to a comparable degree. 1000 four-factor-infected wildtype, miR-34a$^{-/-}$, p21$^{-/-}$ and p53$^{-/-}$ MEFs were collected by flow cytometry and plated, and alkaline phosphatase positive colonies were counted 2 weeks post-plating. *P<0.01 for comparison between wildtype and miR-34a$^{-/-}$ (n=3). **P<0.01 for comparison between wildtype and p21$^{-/-}$ (n=3).

iPSCs derived from miR-34a$^{-/-}$ MEFs, by either three or four-factor transduction, were morphologically and functionally indistinguishable from wildtype iPSCs and ES cells (FIG. 3A). They expressed alkaline phosphatase as an early marker for reprogrammed pluripotent cells (FIG. 3A). In addition, these iPSCs exhibited other characteristic molecular markers for pluripotent stem cells, including the nuclear expression of Oct4 and the membrane expression of SSEA1 (FIG. 3B). Injection of three or four-factor induced miR-34a$^{-/-}$ iPSCs into immuno-compromised nude mice gave rise to well differentiated teratomas, containing terminally differentiated cell types derived from all three germ layers (FIG. 3C, FIG. 4). We did not observe any difference between the wildtype and miR-34a$^{-/-}$ iPSCs in their differentiation capacity in the teratoma formation assay (FIG. 3C, FIG. 4). In addition, when three independent lines of four-factor induced miR-34a$^{-/-}$ iPSCs were introduced into blastocysts, all yielded healthy, adult chimeric mice with a high percentage of iPSC contribution (FIG. 3D, FIG. 5). These data suggest that miR-34a deficiency enhances the efficiency of iPSC generation without compromising iPSC self-renewal and pluripotency.

FIGS. 3A-D. miR-34a$^{-/-}$ iPSCs are functionally indistinguishable from wildtype iPSCs. A. Morphology of four-factor induced wildtype and miR-34a$^{-/-}$ iPSC lines. iPSCs derived from both wildtype and miR-34a$^{-/-}$ MEFs, on a mixed C57BL/6 and 129S4Sv/Jae genetic background, exhibited ES-like morphology in culture, with robust alkaline phosphatase expression. B. Molecular characterization of four-factor induced wildtype and miR-34a$^{-/-}$ iPSCs. Both wildtype and miR-34a$^{-/-}$ iPSCs express pluripotency markers, including nuclear expression of Oct4 and membrane expression of SSEA1. C. Three-factor-induced miR-34a$^{-/-}$ iPSCs generated differentiated teratomas. Teratomas derived from miR-34a$^{-/-}$ iPSCs were harvested from nude mice 6 weeks after subcutaneous injection, and H&E staining revealed terminally differentiated cell types from all three germ layers. D. Four-factor-induced miR-34a$^{-/-}$ iPSCs contribute to adult chimeric mice. We injected passage seven Oct4-Gfp/+, miR-34a$^{-/-}$ iPSCs into albino-C57BL/6/cBrd/cBrd/cr blastocysts to determine their ability to contribute to adult chimeric mice. Since these iPSCs are on a mixed C57BL/6 and 129S4Sv/Jae genetic background, iPSC contribution to the chimeric animals was scored by coat color pigmentation in an otherwise albino coat.

FIG. 4. Four-factor induced wildtype and miR-34a$^{-/-}$ iPSCs generated differentiated teratomas. Teratomas derived from four-factor induced wildtype (top) and miR-34a$^{-/-}$ iPSCs (bottom) were harvested from nude mice 4-5 weeks after subcutaneous injection. H&E staining revealed terminally differentiated cell types and tissue types from all three germ layers, including epidermis, hair follicles and neural rosette from ectoderm, cartilage, bone and muscle from mesoderm, and gut-like epithelia and ciliated epithelia from endoderm.

Figure 6:
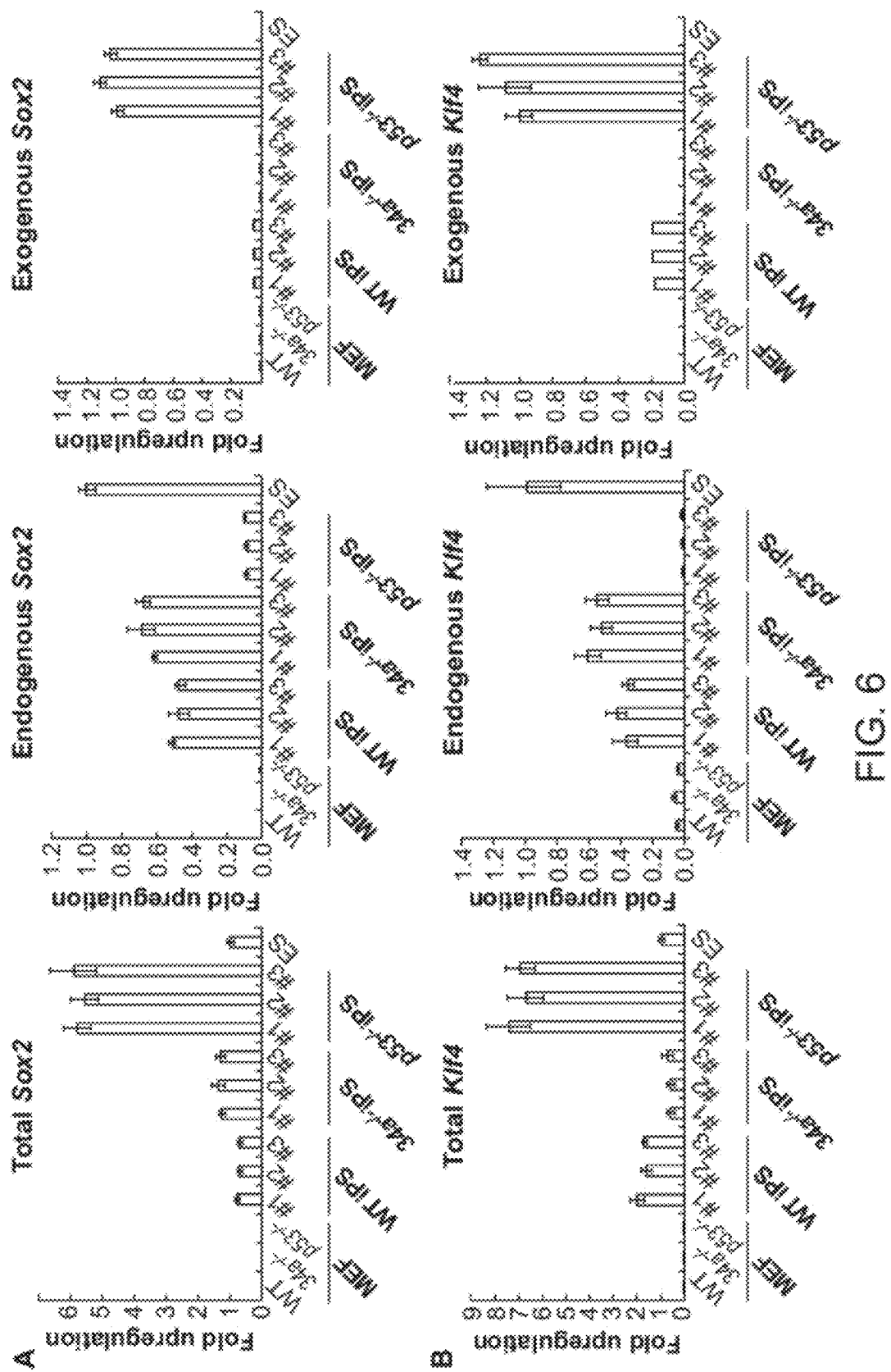
FIGS. 6A-E depict endogenous, exogenous, and total levels of reprogramming factors in four-factor-induced iPSCs.
Figure 6:
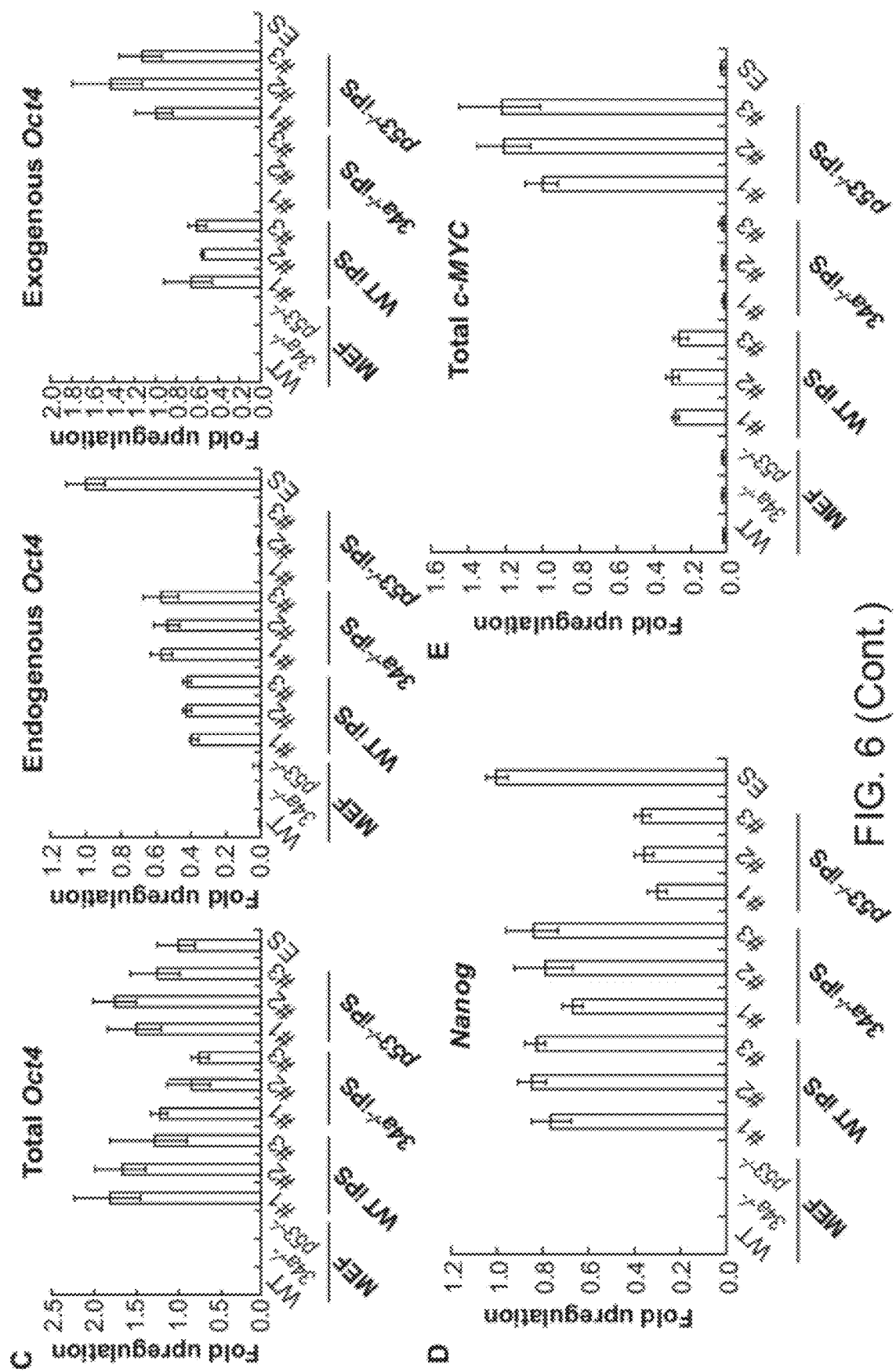
Figure 7:
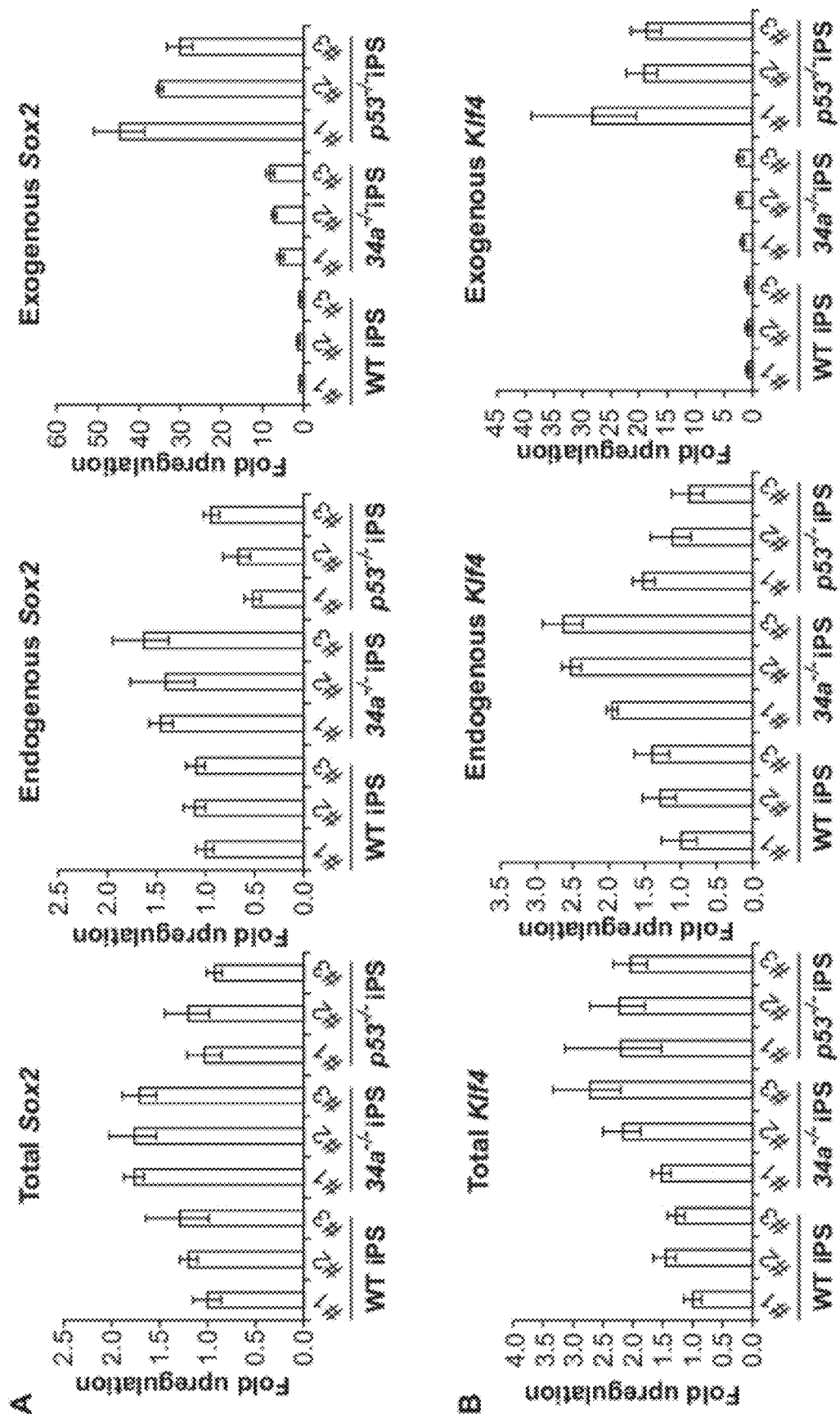
FIGS. 7A-E depict endogenous, exogenous, and total levels of reprogramming factors in three-factor-induced iPSCs.
Figure 7:
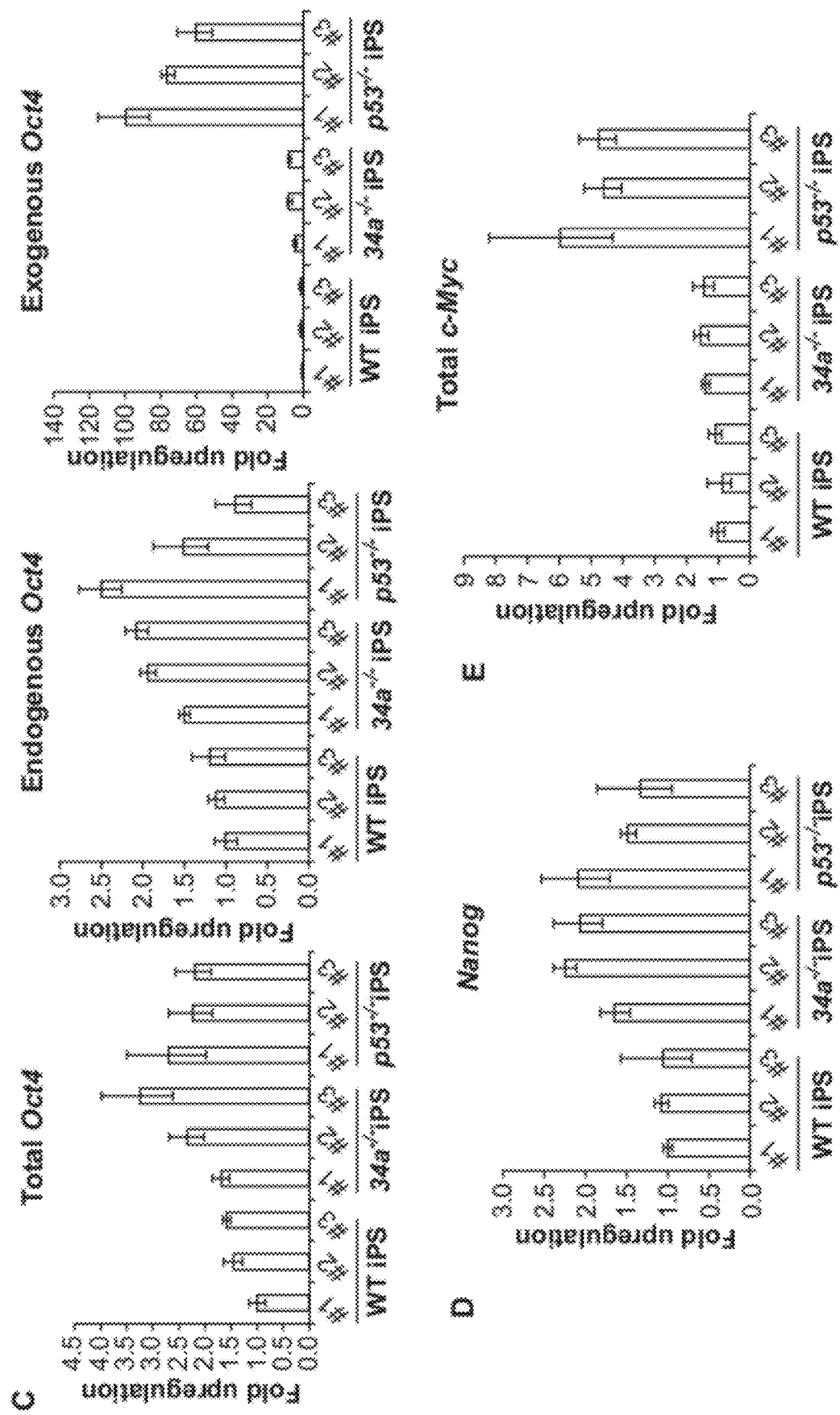

Although loss of p53 induced reprogramming more efficiently than miR-34 deficiency, the p53$^{-/-}$ iPSCs generated exhibited compromised self-renewal and differentiation[4]. Four-factor-induced p53 null iPSCs on the C57BL/6 background were not stable in culture. They lost ES-cell-like morphology after 4-5 passages in vitro, underwent differentiation easily upon passaging or under suboptimal cell confluence, and failed to generate differentiated teratomas when injected into nude mice. In comparison, four-factor induced C57BL/6 miR-34a$^{-/-}$ iPSCs beyond passage 5 remained stable. It is worth noting that, on a mixed C57BL/6 and 129S4Sv/Jae genetic background, miR-34a$^{-/-}$ iPSCs could be cultured for more than 20 passages without losing the morphology and molecular markers characteristic of iPSCs. In addition, multiple groups have reported difficulties in generating healthy adult chimeras from four-factor induced p53$^{-/-}$ iPSCs[4]. In studies that did generate adult chimeric mice, the majority of these mice die before 7 weeks of age[4]. These findings contrast with the functional pluripotency of the miR-34a$^{-/-}$ iPSCs, which could be maintained stably in culture and generate well-differentiated teratomas. More importantly, all three miR-34a$^{-/-}$ iPSC lines we tested gave rise to a high percentage of healthy adult chimeric mice (FIG. 3D, FIG. 5). As of the time that some miR-34a$^{-/-}$ chimeras had reached 3 months of age, they remained healthy and tumor-free. These functional differences are consistent with our observation that four-factor induced p53$^{-/-}$ iPSCs, but not miR-34a$^{-/-}$ or wildtype iPSCs, failed to silence the retroviral transgenes (FIGS. 6A, 6B, 6C). The exogenous expression of reprogramming factors, particularly that of c-Myc, may impair the self-renewal and differentiation of the resulting p53$^{-/-}$ iPSCs, and cause tumorigenesis in chimeric mice (FIG. 6E). In contrast, the miR-34a$^{-/-}$ iPSCs, either induced by three or four factors, exhibited effective silencing of the exogenous retroviral transgenes, comparable to that of wildtype iPSCs (FIG. 6; FIG. 7). Consistent with the complete transgene silencing, the endogenous expression of key pluripotency genes in miR-34a$^{-/-}$ iPSCs were comparable to the wildtype iPSCs, and much greater than that of the p53$^{-/-}$ iPSCs (FIG. 6). This suggests a more complete reprogramming process resulting from miR-34a deficiency, where pluripotency could be more rapidly established by the endogenous transcription factor circuitry, making the exogenous transgenes dispensable for the maintenance pluripotency state.

FIGS. 6A-E. Endogenous, exogenous and total levels of reprogramming factors in four-factor induced iPSCs. RNAs were prepared from wildtype, miR-34a$^{-/-}$ and p53$^{-/-}$ MEFs, four-factor induced iPSCs, as well as V6.5 ES cells. The levels of endogenous, exogenous and total Sox2(A), Klf4(B) and Oct4(C), the total c-Myc (E), and the expression of Nanog(D), were each determined by real-time PCR analyses (n=3).

FIGS. 7A-E. Endogenous, exogenous and total levels of reprogramming factors in three-factor-induced iPSCs. RNAs were prepared from three-factor induced wildtype, miR-34a$^{-/-}$ and p53$^{-/-}$ iPSCs. The levels of endogenous, exogenous and total Oct4, Sox2, Klf4, and total c-Myc, as well as Nanog expression, were each determined by real-time PCR analyses (n=3).

Enhanced reprogramming efficiency resulting from p53 loss has been attributed to enhanced cell proliferation and cell immortalization, as well as decreased apoptosis and DNA damage response during reprogramming[3-7, 26, 27]. Unlike p53 null MEFs, miR-34a-deficient MEFs exhibit a similar, but slightly enhanced, proliferation rate compared with the wildtype MEFs, at least within the time frame of our reprogramming experiments (FIG. 1D). The slight increase in cell proliferation observed in miR-34a deficient MEFs could contribute to the increased reprogramming efficiency, yet was unlikely to serve as the predominant mechanism. In addition, miR-34a deficiency differs from p53 loss, and failed to protect cells from apoptosis and DNA damage response during reprogramming. On day 3 post transduction of four reprogramming factors, p53$^{-/-}$ MEFs exhibited significant protection against apoptosis, while miR-34a$^{-/-}$ MEFs showed a similar level of apoptosis to wildtype MEFs, as measured by annexin V staining. Consequently, increased DNA damage, as measured by the percentage of γ-H2AX positive cells, was observed only in four-factor transduced p53$^{-/-}$ MEFs 6 days post infection, but not in miR-34a$^{-/-}$ or wildtype counterparts. Taken together, these findings could partially explain the functional differences between the miR-34a$^{-/-}$ and p53$^{-/-}$ iPSCs, and also suggest that miR-34a represses somatic reprogramming through a mechanism that is largely independent of proliferation, apoptosis and DNA damage response.

Figure 9:
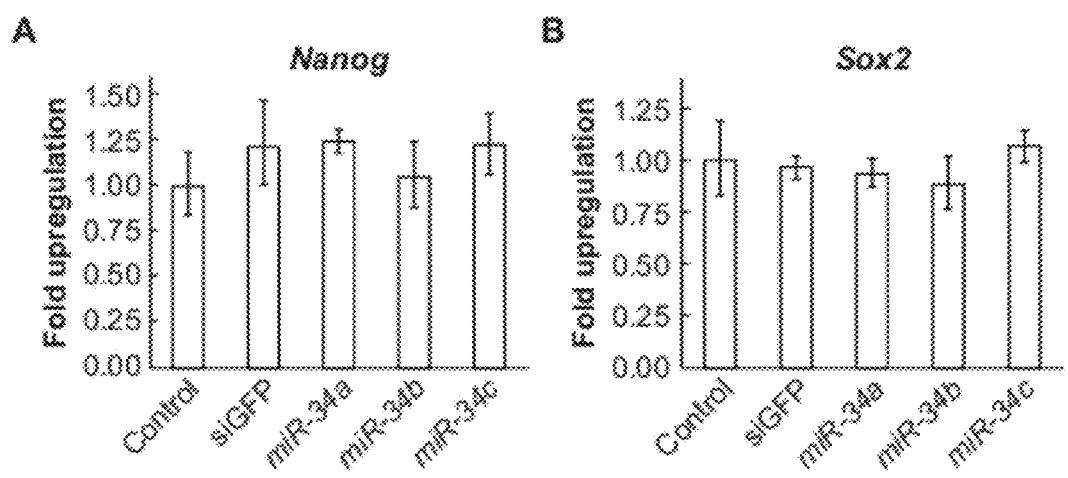
FIGS. 9A and 9B depict the effect of enforced expression of miR-34 miRNAs in ES cells on mRNA levels of Nanog and Sox2.
Figure 10:
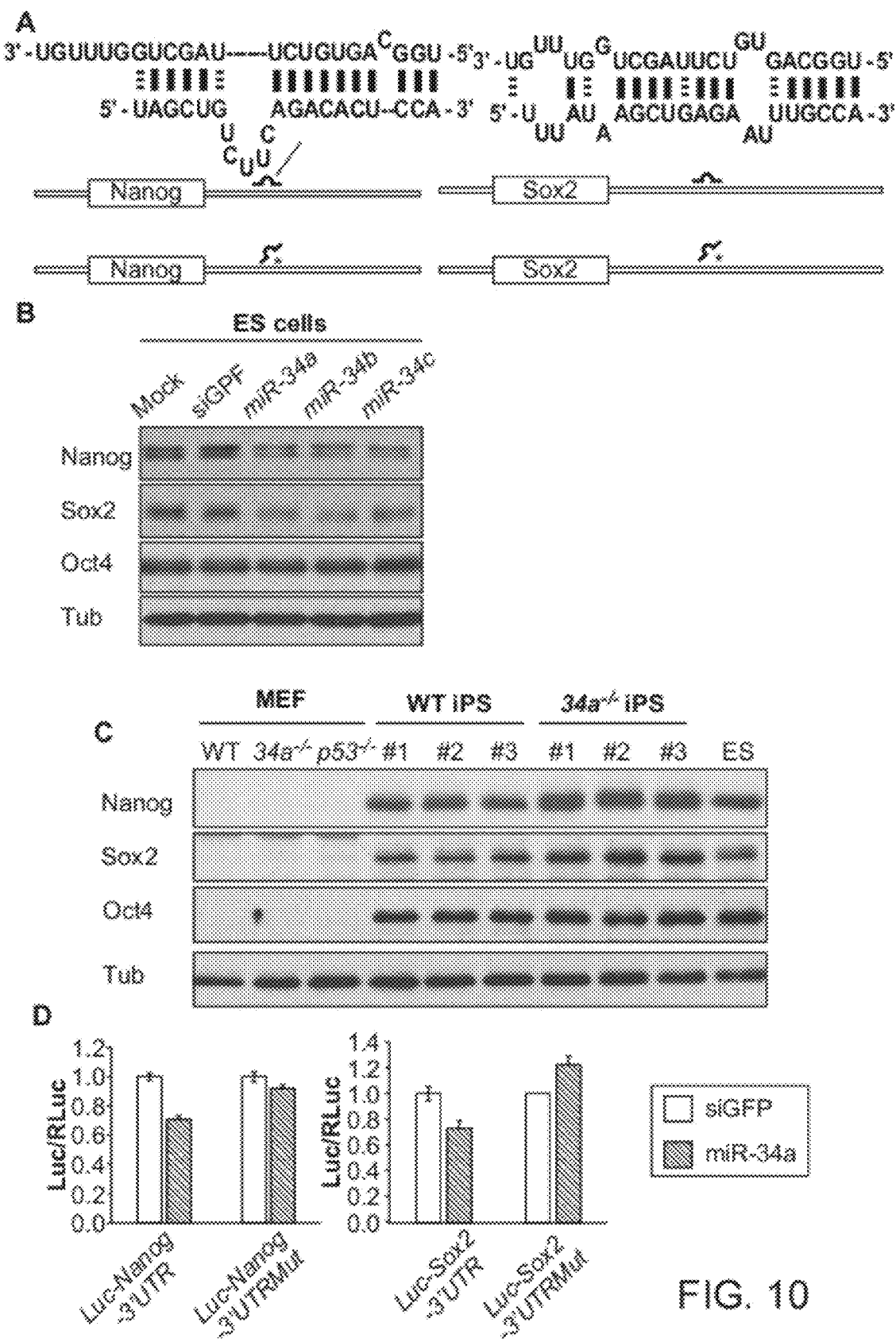
FIGS. 10A-D depict repression of Nanog and Sox2 expression postranscriptionally by miR-34a. A Nanog 3' UTR sequence (5'-uagcugucuucagacaucca-3'; SEQ ID NO:58) is shown in FIG. 10A, left-hand side. A Sox2 3' UTR sequence (5'-uuuauaagcugagaauuugcca-3'; SEQ ID NO:87) is shown in FIG. 10A, right-hand side. miR-34a (5'-UGGCAGUGUCUUAGCUGGUUGU-3'; SEQ ID NO:1) is shown above the Nanog 3' UTR and above the Sox2 3' UTR in FIG. 10A.

Since miR-34a deficiency increases the efficiency of somatic cell reprogramming, we examined all genes that have been reported to promote iPSC generation for possible miR-34a binding sites. RNA22 identified a number of such genes that contained predicted miR-34 sites[28]. Nanog, Sox2, and N-Myc were selected as top candidates, due to their potent effects in promoting reprogramming[1, 29, 30], as well as the presence of putative miR-34a binding sites within their 3'UTRs (FIG. 10A, FIG. 8). ES cells over-expressing miR-34a, miR-34b or miR-34c had decreased Nanog, Sox2 and N-Myc protein levels, although their mRNA abundance was unaffected, suggesting that miR-34-mediated translational repression is the dominant mechanism for this post-transcriptional gene regulation (FIG. 10B, FIG. 8, FIG. 9). The reduction in Nanog, Sox2 and N-Myc expression by miR-34 miRNAs was not due to iPSC differentiation, because the expression of Oct4, a marker for undifferentiated iPSCs, remained unaltered (FIG. 10B). Consistent with this finding, elevated levels of Sox2, Nanog and N-Myc proteins were also observed in miR-34a$^{-/-}$ iPSCs, compared to those of the wildtype iPSCs (FIG. 10C, FIG. 8). Since our real time PCR analysis suggested effective silencing of the Sox2 transgene in miR-34a$^{-/-}$ iPSCs (FIG. 6A), the difference of Sox2 protein level we observed must be due to the difference in endogenous Sox2 expression. Similarly, Oct4 protein levels were unchanged between wildtype and miR-34a$^{-/-}$ iPSCs, suggesting the increase in Sox2, Nanog and N-Myc we observed was specific for miR-34 deficiency, and not due to alterations in iPSC pluripotency state (FIG. 10C, FIG. 8C). Taken together, the post-transcriptional derepression of multiple pluripotency genes resulting from miR-34a deficiency is likely to facilitate the establishment of the regulatory circuitry for pluripotency, efficiently decouple the induced pluripotency state from reliance on the exogenous reprogramming factors, and consequently promote and accelerate establishment of a pluripotent state during reprogramming.

N-Myc is a previously identified miR-34a target in neuroblastoma cell lines, whose downregulation by miR-34 is mediated through the two binding sites within its 3'UTR[31]. To determine whether miR-34a directly targets Sox2 and Nanog, we constructed luciferase reporters that contained the wildtype Sox2 3'UTR or the wildtype Nanog 3'UTR. Both Sox2 and Nanog 3'UTRs were repressed by exogenous expression of miR-34a in Dicer-deficient Hct116 cells (FIG. 10D). In addition, mutations in the miR-34a binding site of each luciferase reporter abolished miR-34a-dependent regulation of these 3'UTRs (FIG. 10D). Taken together, miR-34a directly targets Nanog, Sox2 and N-Myc expression, providing a barrier for the kinetics and efficiency of iPSC generation. Interestingly, Nanog was previously identified as a direct target of p53-mediated transcriptional repression in a number of stem cell systems, including ES cells and spermatogonial stem cells[32, 33]. The data support post-transcriptional regulation of Nanog by miR-34a.

FIGS. 8A-C. miR-34a represses N-Myc expression. A. Schematic representation of the N-Myc 3'UTR, and their miR-34 binding sites. The mouse N-Myc contains one putative miR-34a binding site in its 3'UTR, which is conserved in human. B. Enforced expression of miR-34 miRNAs reduced the protein levels of N-Myc. Feeder-less ES cells were transfected with miRNA mimics for miR-34a, miR-34b and miR-34c, in addition to a negative control, siGFP. Using Western analysis, reduction in the protein levels of N-Myc was observed 48 hours after transfection in all miR-34 transfected cells. α-Tubulin (Tub) was used as a loading control in this analysis. C. Derepression of N-Myc in miR-34a$^{-/-}$ iPSCs. Lysates prepared from wildtype and miR-34a$^{-/-}$ MEFs and four-factor induced iPSCs were subjected to Western analysis. An increase of the N-Myc protein level was observed in miR-34a$^{-/-}$ iPSCs. For all Western analyses, α-Tubulin (Tub) was used as a normalization control.

FIGS. 9A and 9B. Enforced expression of miR-34 miRNAs in ES cells did not alter the mRNA level of Nanog and Sox2. RNAs were prepared from mock transfected ES cells, as well as those transfected with siGFP, miR-34a, miR-34b and miR-34c. The levels of Nanog and Sox2 in each sample were determined by real-time PCR analyses 72 hours post transfection.

FIGS. 10A-D. miR-34a represses Nanog, and Sox2 expression post-transcriptionally. A. Schematic representation of the Nanog and Sox2 3'UTR, and their miR-34 binding sites. The mouse Nanog 3'UTR and Sox2 3'UTR each contains one putative miR-34a binding site in their 3'UTRs (red). The predicted miR-34a binding site in mouse Sox2 was conserved in human as well. The Nanog and Sox2 3' fragments that carry mutations in the corresponding miR-34a binding sites (designated with asterisks), as well as their wildtype counterparts, were each cloned downstream of a luciferase reporter (Luc). B. Enforced expression of miR-34 miRNAs reduced the protein levels of Nanog and Sox2. Feeder-less ES cells were transfected with miRNA mimics for miR-34a, miR-34b and miR-34c, in addition to a negative control, siGFP. Using Western analysis, significant reduction in the protein levels of Nanog and Sox2, but not Oct4, was observed 72 hours after transfection in all miR-34 transfected cells. α-Tubulin (Tub) was used as a loading control in this analysis. C. Derepression of Nanog and Sox2 in miR-34a$^{-/-}$ iPSCs. Lysates prepared from wildtype and miR-34a$^{-/-}$ MEFs and four-factor induced iPSCs were subjected to Western analysis. A significant increase of the Nanog and Sox2 protein levels was observed in miR-34a$^{-/-}$ iPSCs. For all Western analyses, α-Tubulin (Tub) was used as a normalization control. D. Specific repression of Luc-Nanog-3'UTR and Luc-Sox2-3'UTR reporter by miR-34a. Luc-Nanog-3'UTR (left) or Luc-Sox2-3'UTR (right) was co-transfected with mimics of miR-34a and a control siRNA, respectively. Only miR-34a significantly repressed the reporter expression. miR-34a co-transfection with the mutated Luc-Nanog-3'UTR or Luc-Sox2-3'UTR reporters carrying the deletion miR-34a site significantly derepressed the Luc reporter expression.

LNA Effects

Figure 19A:
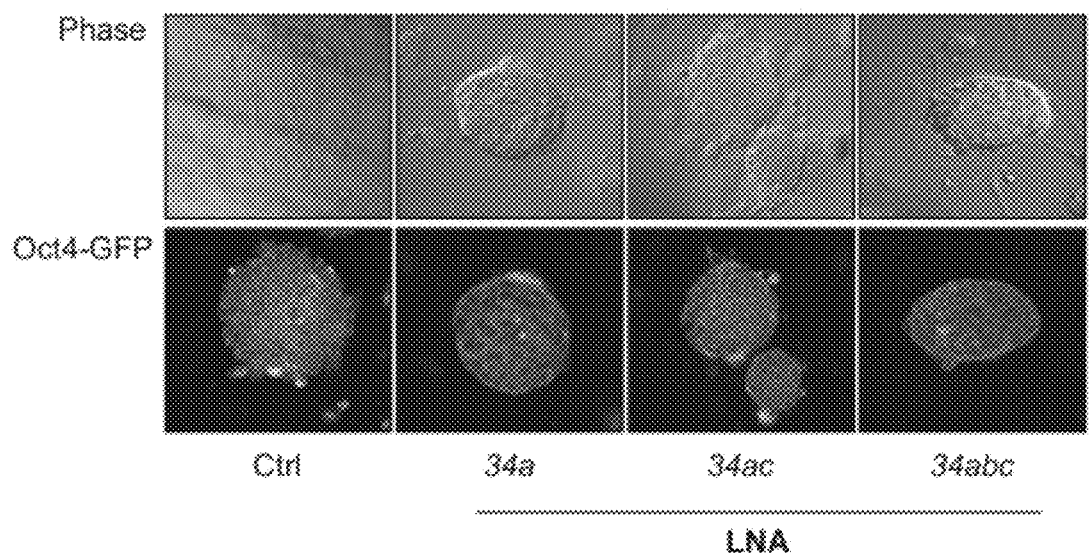
FIGS. 19A-C depict the effect of locked nucleic acid (LNA) on reprogramming.
Figure 19B:
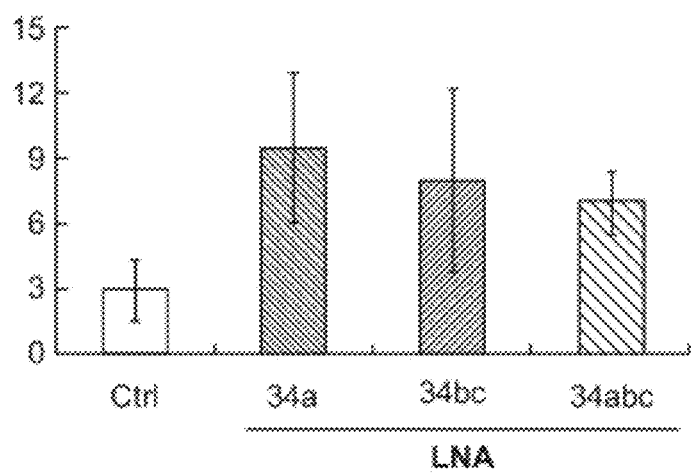
Figure 19C:
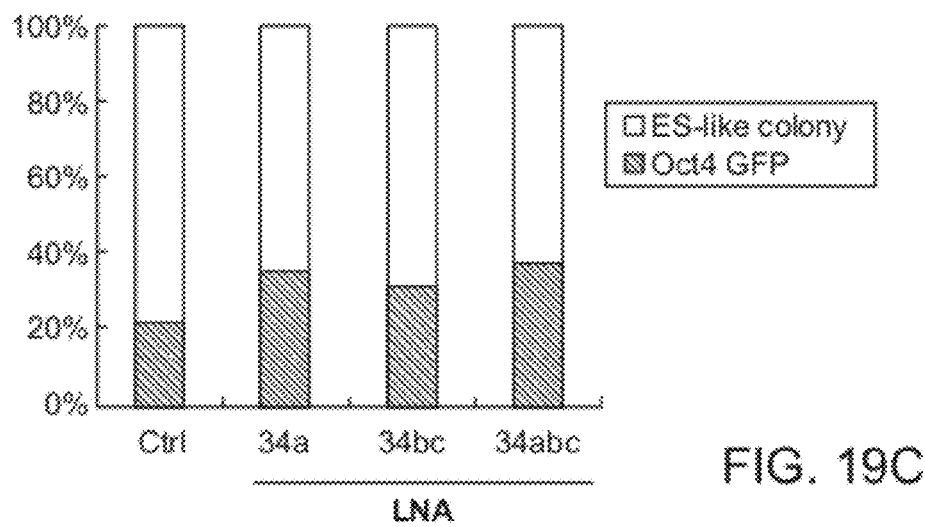

Oct4-GFP transgenic MEFs were used to quantify reprogramming efficiency by mir-34 LNA transfection. MEF were infected with retroviral vectors expressing Oct4, Sox2, c-Myc or Klf4 and then transfected with locked nucleic acid (LNA) for mir-34 a and/or bc. The resulted reprogramming efficiency is quantified by the number of GFP positive clones. The data are shown in FIGS. 19A-C.

REFERENCES

1. Yamanaka, S. & Blau, H. M. Nuclear reprogramming to a pluripotent state by three approaches. *Nature* 465, 704-712.
2. Takahashi, K. & Yamanaka, S. Induction of pluripotent stem cells from mouse embryonic and adult fibroblast cultures by defined factors. *Cell* 126, 663-676 (2006).
3. Kawamura, T. et al. Linking the p53 tumour suppressor pathway to somatic cell reprogramming. *Nature* 460, 1140-1144 (2009).
4. Hong, H. et al. Suppression of induced pluripotent stem cell generation by the p53-p21 pathway. *Nature* 460, 1132-1135 (2009).
5. Utikal, J. et al. Immortalization eliminates a roadblock during cellular reprogramming into iPS cells. *Nature* 460, 1145-1148 (2009).
6. Marion, R. M. et al. A p53-mediated DNA damage response limits reprogramming to ensure iPS cell genomic integrity. *Nature* 460, 1149-1153 (2009).
7. Li, H. et al. The Ink4/Arf locus is a barrier for iPS cell reprogramming. *Nature* 460, 1136-1139 (2009).
8. Raver-Shapira, N. et al. Transcriptional activation of miR-34a contributes to p53-mediated apoptosis. *Mol Cell* 26, 731-743 (2007).

9. He, L. et al. A microRNA component of the p53 tumour suppressor network. *Nature* 447, 1130-1134 (2007).
10. Chang, T. C. et al. Widespread microRNA repression by Myc contributes to tumorigenesis. *Nat Genet.* 40, 43-50 (2008).
11. Chang, T. C. et al. Transactivation of miR-34a by p53 broadly influences gene expression and promotes apoptosis. *Mol Cell* 26, 745-752 (2007).
12. Takahashi, K. et al. Induction of pluripotent stem cells from adult human fibroblasts by defined factors. *Cell* 131, 861-872 (2007).
13. Yu, J. et al. Induced pluripotent stem cell lines derived from human somatic cells. *Science* 318, 1917-1920 (2007).
14. Park, I. H. et al. Reprogramming of human somatic cells to pluripotency with defined factors. *Nature* 451, 141-146 (2008).
15. Meissner, A., Wernig, M. & Jaenisch, R. Direct reprogramming of genetically unmodified fibroblasts into pluripotent stem cells. *Nat Biotechnol* 25, 1177-1181 (2007).
16. Huangfu, D. et al. Induction of pluripotent stem cells from primary human fibroblasts with only Oct4 and Sox2. *Nat Biotechnol* 26, 1269-1275 (2008).
17. Krizhanovsky, V. & Lowe, S. W. Stem cells: The promises and perils of p53. *Nature* 460, 1085-1086 (2009).
18. He, L., He, X., Lowe, S. W. & Hannon, G. J. microRNAs join the p53 network—another piece in the tumour-suppression puzzle. *Nat Rev Cancer* 7, 819-822 (2007).
19. Ambros, V. The functions of animal microRNAs. *Nature* 431, 350-355 (2004).
20. Bartel, D. P. MicroRNAs: genomics, biogenesis, mechanism, and function. *Cell* 116, 281-297 (2004).
21. He, L. & Hannon, G. J. MicroRNAs: small RNAs with a big role in gene regulation. *Nat Rev Genet.* 5, 522-531 (2004).
22. Zamore, P. D. & Haley, B. Ribo-gnome: the big world of small RNAs. *Science* 309, 1519-1524 (2005).
23. Filipowicz, W., Bhattacharyya, S. N. & Sonenberg, N. Mechanisms of post-transcriptional regulation by microRNAs: are the answers in sight? *Nat Rev Genet.* 9, 102-114 (2008).
24. Riley, T., Sontag, E., Chen, P. & Levine, A. Transcriptional control of human p53-regulated genes. *Nat Rev Mol Cell Biol* 9, 402-412 (2008).
25. Seoane, J., Le, H. V. & Massague, J. Myc suppression of the p21(Cip1) Cdk inhibitor influences the outcome of the p53 response to DNA damage. *Nature* 419, 729-734 (2002).
26. Banito, A. et al. Senescence impairs successful reprogramming to pluripotent stem cells. *Genes Dev* 23, 2134-2139 (2009).
27. Hanna, J. et al. Direct cell reprogramming is a stochastic process amenable to acceleration. *Nature* 462, 595-601 (2009).
28. Miranda, K. C. et al. A pattern-based method for the identification of MicroRNA binding sites and their corresponding heteroduplexes. *Cell* 126, 1203-1217 (2006).
29. Nakagawa, M., Takizawa, N., Narita, M., Ichisaka, T. & Yamanaka, S. Promotion of direct reprogramming by transformation-deficient Myc. *Proc Natl Acad Sci USA* 107, 14152-14157.
30. Varlakhanova, N. V. et al. myc maintains embryonic stem cell pluripotency and self-renewal. *Differentiation* 80, 9-19.
31. Wei, J. S. et al. The MYCN oncogene is a direct target of miR-34a. *Oncogene* 27, 5204-5213 (2008).
32. Kuijk, E. W. et al. PTEN and TRP53 independently suppress Nanog expression in spermatogonial stem cells. *Stem Cells Dev* 19, 979-988.
33. Lin, T. et al. p53 induces differentiation of mouse embryonic stem cells by suppressing Nanog expression. *Nat Cell Biol* 7, 165-171 (2005).
34. Melton, C., Judson, R. L. & Blelloch, R. Opposing microRNA families regulate self-renewal in mouse embryonic stem cells. *Nature* 463, 621-626.
35. Wang, Y. et al. Embryonic stem cell-specific microRNAs regulate the G1-S transition and promote rapid proliferation. *Nat Genet.* 40, 1478-1483 (2008).
36. Judson, R. L., Babiarz, J. E., Venere, M. & Blelloch, R. Embryonic stem cell-specific microRNAs promote induced pluripotency. *Nat Biotechnol* 27, 459-461 (2009).
37. Wang, Y., Medvid, R., Melton, C., Jaenisch, R. & Blelloch, R. DGCR8 is essential for microRNA biogenesis and silencing of embryonic stem cell self-renewal. *Nat Genet.* 39, 380-385 (2007).
38. Heo, I. et al. Lin28 mediates the terminal uridylation of let-7 precursor MicroRNA. *Mol Cell* 32, 276-284 (2008).
39. Newman, M. A., Thomson, J. M. & Hammond, S. M. Lin-28 interaction with the Let-7 precursor loop mediates regulated microRNA processing. *RNA* 14, 1539-1549 (2008).
40. Viswanathan, S. R. & Daley, G. Q. Lin28: A microRNA regulator with a macro role. *Cell* 140, 445-449.
41. Viswanathan, S. R., Daley, G. Q. & Gregory, R. I. Selective blockade of microRNA processing by Lin28. *Science* 320, 97-100 (2008).
42. Krutzfeldt, J. et al. Silencing of microRNAs in vivo with 'antagomirs'. *Nature* 438, 685-689 (2005).
43. Elmen, J. et al. LNA-mediated microRNA silencing in non-human primates. *Nature* 452, 896-899 (2008).
44. Warren, L. et al. Highly efficient reprogramming to pluripotency and directed differentiation of human cells with synthetic modified mRNA. *Cell Stem Cell* 7, 618-630.
45. Zhou, H. et al. Generation of induced pluripotent stem cells using recombinant proteins. *Cell Stem Cell* 4, 381-384 (2009).
46. Ichida, J. K. et al. A small-molecule inhibitor of tgf-Beta signaling replaces sox2 in reprogramming by inducing nanog. *Cell Stem Cell* 5, 491-503 (2009).
47. Lyssiotis, C. A. et al. Reprogramming of murine fibroblasts to induced pluripotent stem cells with chemical complementation of Klf4. *Proc Natl Acad Sci USA* 106, 8912-8917 (2009).
48. Maherali, N. & Hochedlinger, K. Guidelines and techniques for the generation of induced pluripotent stem cells. *Cell Stem Cell* 3, 595-605 (2008).
49. Ben-Porath, I. et al. An embryonic stem cell-like gene expression signature in poorly differentiated aggressive human tumors. *Nat Genet.* 40, 499-507 (2008).
50. Cummins, J. M. et al. The colorectal microRNAome. *Proc Natl Acad Sci USA* 103, 3687-3692 (2006).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of generating a pluripotent stem cell from a somatic cell, the method comprising introducing into the somatic cell:
   a) one or more exogenous reprogramming factor polypeptides or one or more nucleic acids comprising nucleotide sequences encoding one or more reprogramming factor polypeptides; and
   b) a nucleic acid agent that is selective for miR-34 and selectively reduces the level or antagonizes the function of a miR-34 in the cell, and increases the efficiency of generating the pluripotent stem cell compared to the efficiency obtained by introducing (a) in the absence of said nucleic acid agent,
   wherein said introducing results in reprogramming of the somatic cell into a pluripotent stem cell.

2. The method of claim 1, wherein the miR-34 is one or more of miR-34a, miR-34b, and miR-34c.

3. The method of claim 1, wherein the nucleic acid agent is a modified oligonucleotide having a length of from about 12 to about 30 linked nucleosides.

4. The method of claim 3, wherein each nucleoside of the modified oligonucleotide comprises the same sugar modification.

5. The method of claim 1, wherein the nucleic acid agent comprises a sugar modification selected from 2'-O-methoxyethyl, 2'-fluoro, locked nucleic acid, and ethylene bridged nucleic acid.

6. The method of claim 5, wherein the sugar modification is 2'-O-methoxyethyl.

7. The method of claim 1, wherein the nucleic acid comprises at least one non-phosphodiester internucleosidic linkage.

8. The method of claim 7, wherein the internucleosidic linkage is selected from phosphorothioate, phosphorodithioate, phosphoramidate, phosphorodiamidate, methylphosphonate, P-chiral linkage, chiral phosphorothioate, phosphoroselenoate, phosphorodiselenoate, phosphoroanilothioate, phosphoranilidates, phosphotriester, aminoalkylphosphotriester, alkylphosphotriester, carbonate, carbamate, morpholino carbamate, 3'-thioformacetal, morpholino, and silyl.

9. The method of claim 1, wherein the nucleic acid comprises at least one modified nucleotide.

10. The method of claim 9, wherein the modified nucleotide is a 2'-deoxy-2'-fluoro modified nucleotide, a 2'-deoxy-modified nucleotide, a locked nucleotide, an abasic nucleotide, a 2'-ammo-modified nucleotide, a 2'-alkyl-modified nucleotide, a morpholino nucleotide, a phosphoramidate, or a non-natural base comprising nucleotide.

11. The method of claim 1, wherein at least one deoxyribose ring in the nucleic acid is substituted.

12. The method of claim 11, wherein at least one deoxyribose ring in the antisense nucleic acid is substituted with a 6-membered morpholine ring.

13. The method of claim 1, wherein the nucleic acid comprises at least one substituted sugar moiety.

14. The method of claim 1, wherein the one or more reprogramming factor polypeptides are selected from Oct3/4, Sox2, Klf4, c-Myc, Nanog and LIN28.

15. The method of claim 1, wherein the one or more reprogramming factor polypeptides are Oct4, Sox2, and Klf4.

16. The method of claim 1, wherein said introducing is carried out in vitro.

17. The method of claim 1, wherein the one or more exogenous reprogramming factor polypeptides comprises a heterologous protein transduction domain.

18. The method of claim 1, wherein the cell to be reprogrammed is a somatic tissue stem cell.

19. The method of claim 1, wherein the somatic cell is an adult somatic tissue stem cell.

20. The method of claim 1, wherein the somatic cell is a human cell.

21. The method of claim 1, wherein the nucleic acid encoding the one or more reprogramming factors is a non-viral expression vector or a viral expression vector.

22. The method of claim 21, wherein the expression vector is autonomously replicable extrachromosomally.

23. The method of claim 1, wherein the nucleic acid that reduces the level of miR-34 is an antisense oligonucleotide, or a nucleic acid encoding an antisense oligonucleotide.

24. The method of claim 23, wherein the antisense nucleic acid forms a stable duplex with a miR-34 nucleic acid in the somatic cell.

25. The method of claim 23, wherein the antisense-encoding nucleotide sequence is operably linked to an inducible promoter.

26. The method of claim 1, wherein said nucleic acid agent increases by at least two-fold the efficiency of generating the pluripotent stem cell compared to the efficiency obtained by introducing (a) in the absence of said nucleic acid agent.

27. The method of claim 1, wherein the miR-34 is miR-34a.

28. The method of claim 1, wherein the miR-34 is selected from: (i) miR-34a; (ii) miR-34b and miR-34c; and (iii) miR-34a, miR-34b, and miR-34c.

* * * * *